United States Patent
Reinhard et al.

(10) Patent No.: US 7,355,053 B2
(45) Date of Patent: Apr. 8, 2008

(54) 1-PHENYLPYRROLIDINE-2-ONE-3-CARBOXAMIDES

(75) Inventors: Robert Reinhard, Ludwigshafen (DE); Gerhard Hamprecht, Weinheim (DE); Michael Puhl, Lampertheim (DE); Werner Seitz, Plankstadt (DE); Liliana Parra Rapado, Mannheim (DE); Annegret Scannell-Lansky, Pfungstadt (DE); Klaus Groβmann, Neuhofen (DE); Helmut Schiffer, Groβfischlingen (DE); Matthias Witschel, Bad Dürkheim (DE); Cyrill Zagar, Mannheim (DE); Andreas Landes, Römerberg-Heiligenstein (DE); Michael Rack, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 140 days.

(21) Appl. No.: 10/531,573

(22) PCT Filed: Oct. 17, 2003

(86) PCT No.: PCT/EP03/11557

§ 371 (c)(1),
(2), (4) Date: Apr. 18, 2005

(87) PCT Pub. No.: WO2004/037787

PCT Pub. Date: May 6, 2004

(65) Prior Publication Data

US 2006/0019831 A1    Jan. 26, 2006

(30) Foreign Application Priority Data

Oct. 18, 2002  (DE) ................. 102 48 700

(51) Int. Cl.
*A61K 31/402* (2006.01)
*C07D 207/08* (2006.01)

(52) U.S. Cl. ...................... 548/400; 514/408
(58) Field of Classification Search ............... 548/248, 548/517, 546, 400; 514/378, 423, 408; 564/12; 546/21

See application file for complete search history.

(56) References Cited

U.S. PATENT DOCUMENTS 4,874,422 A * 10/1989 Woolard ................ 504/287

FOREIGN PATENT DOCUMENTS

| WO | WO 90/07500 | 7/1990 |
| WO | WO9007500 A1 * | 7/1990 |
| WO | WO 95/33718 | 12/1995 |
| WO | WO 95/33719 | 12/1995 |
| WO | WO 02/48114 A1 | 6/2002 |

* cited by examiner

*Primary Examiner*—Joseph K. McKane
*Assistant Examiner*—Janet L. Coppins
(74) *Attorney, Agent, or Firm*—Rothwell, Figg, Ernst & Manbeck, P.C.

(57) ABSTRACT

The invention relates to 1-phenylpyrrolidin-2-one-3-carboxamides of the formula I

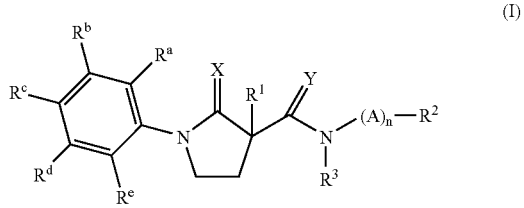

where the variables $R^1$, $R^2$, $R^3$, X, Y, A, n, $R^a$, $R^b$, $R^c$, $R^d$ and $R^e$ are as defined in claim 1 and to their agriculturally useful salts.

Moreover, the invention relates to
the use of compounds I and/or their salts as herbicides;
crop protection compositions comprising at least one 1-phenylpyrrolidin-2-one-3-carboxamide of the formula I and/or at least one agriculturally useful salt of I as active substances; and also
a method for controlling unwanted vegetation, which comprises allowing a herbicidally effective amount of at least one 1-phenylpyrrolidin-2-one-3-carboxamide of the formula I or an agriculturally useful salt of I to act on plants, their habitat or on seed.

24 Claims, No Drawings

1-PHENYLPYRROLIDINE-2-ONE-3-CARBOXAMIDES

CROSS REFERENCE TO RELATED APPLICATION

This application is a 35 USC § 371 National Phase Entry Application from PCT/EP2003/011557, filed Oct. 17, 2003, and designating the United States.

The present invention relates to 1-phenylpyrrolidin-2-one-3-carboxamides and their agriculturally useful salts, to compositions comprising such compounds and to the use of the 1-phenylpyrrolidin-2-one-3-carboxamides, of their salts or of compositions comprising them as herbicides.

WO 95/33719 describes 1-arylthiazolidinones, 1-aryloxazolidinones and 1-arylpyrrolidinones of the formula:

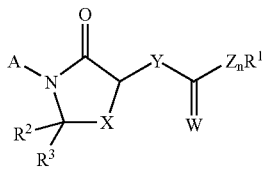

where A is an aromatic or heteroaromatic radical, n is 0 or 1, x is in particular S, O or $CH_2$, Y is in particular S, O, $CH_2$ or $CH(CH_3)$ or a group $NR^6$, Z is in particular NH or O, $R^1$ is preferably selected from unsubstituted or substituted alkyl, alkenyl, alkynyl, unsubstituted or substituted cycloalkyl, unsubstituted or substituted phenyl, benzyl or hetaryl, acyl, alkoxycarbonylalkyl and silyl, $R^2$ and $R^3$ are in particular hydrogen and $R^6$ is inter alia hydrogen, formyl, unsubstituted or substituted alkyl, alkenyl, alkynyl, cycloalkyl or unsubstituted or substituted aryl.

WO 95/33718 describes 1-phenylpyrrolidinethiones having herbicidal activity which, in the 3-position of the pyrrolidinethione ring, contain a group O—C(O)—$NR^1R^2$ where $R^1R^2$ are, for example, hydrogen, an unsubstituted or substituted hydrocarbon radical or hetaryl, or together with the nitrogen atom to which they are attached form a heterocycle.

Furthermore, U.S. Pat. No. 4,874,422 discloses herbicidally active 1-phenylpyrrolidin-2-one-3-carboxamides of the formula A

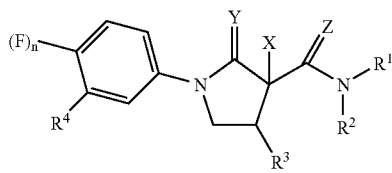

where X is hydrogen or halogen, Y and Z independently of one another are O or S, n is 0 or 1, $R^1$ is hydrogen, alkyl, alkenyl, alkynyl, cycloalkyl, alkoxy, phenyl, halophenyl, benzyl, halobenzyl, or alkyl which is substituted by alkoxy, alkylthio, phenyl, hydroxyl or cyano, $R^2$ is hydrogen or alkyl, $R^3$ is alkyl or alkenyl and $R^4$ is selected from the group consisting of hydrogen, halogen, methyl, trifluoromethyl, 1,1,2,2-tetrafluoroethyl, 1,1,2,2-tetrafluoroethyloxy, difluoromethoxy, trifluoromethoxy, methylsulfanyl, methylsulfinyl, methylsulfonyl, methoxyiminomethyl, methoxyimino-1-ethyl, benzyloxyiminomethyl and benzyloxyimino-1-ethyl.

The herbicidal activity of the 1-arylpyrrolidinones described in the prior art is not always satisfactory. Their selectivity for harmful plants is unsatisfactory, too. In particular, even at low application rates, such herbicides tend to interfere with the generation of chlorophyll even in crop plants, which is undesirable in principle and may lead to yield losses.

It is an object of the present invention to provide novel herbicidally active compounds which allow a better targeted control of unwanted plants than the known herbicides. Advantageously, the novel herbicides should be highly active against harmful plants. Moreover, high compatibility with crop plants is desirable. Moreover, the compounds should have no adverse effect on the chlorophyll synthesis in crop plants.

We have found that this object is achieved by 1-phenylpyrrolidin-2-one-3-carboxamides of the formula I defined below and their agriculturally useful salts:

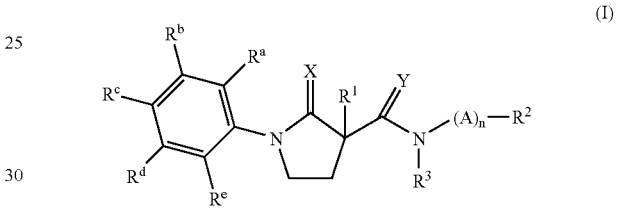

(I)

where the variables $R^1$, $R^2$, $R^3$, X, Y, A, n, $R^a$, $R^b$, $R^c$, $R^d$ and $R^e$ are as defined below:

$R^1$ is hydrogen, OH, Cl, Br, $C_1$-$C_6$-alkyl, $C_3$-$C_6$-cycloalkyl, $C_3$-$C_6$-alkenyl, $C_3$-$C_6$-alkynyl, $C(O)R^4$ or $OC(O)R^4$;

$R^2$ and $R^3$ independently of one another are hydrogen, $C_1$-$C_{10}$-alkyl, $C_3$-$C_{10}$-cycloalkyl, $C_7$-$C_{10}$-polycycloalkyl, $C_3$-$C_8$-alkenyl, $C_3$-$C_{10}$-alkynyl, $C_5$-$C_{10}$-cycloalkenyl, $C_3$-$C_8$-cycloalkyl-$C_1$-$C_4$-alkyl, phenyl or 3- to 7-membered heterocyclyl, where the 9 last-mentioned groups may be unsubstituted, partially or fully halogenated and/or contain 1, 2 or 3 radicals selected from the group consisting of OH, CN, $NO_2$, COOH, $C_1$-$C_6$-alkyl, $C_1$-$C_6$-haloalkyl, $C_1$-$C_6$-alkoxy, $C_1$-$C_4$-haloalkoxy, $C_2$-$C_6$-alkenyl, $C_2$-$C_6$-alkynyl, $C_1$-$C_6$-alkylthio, $C_1$-$C_4$-haloalkylthio, unsubstituted or substituted phenyl, $COOR^5$, $NR^6R^7$, $C(O)NR^8SO_2R^{13}$, $C(O)NR^8R^9$ and 3- to 7-membered heterocyclyl, and each heterocyclyl may contain 1, 2 or 3 heteroatoms selected from the group consisting of oxygen, nitrogen, sulfur, a group $NR^{10}$ and a group $SO_2$, and, if appropriate, 1, 2 or 3 carbonyl groups and/or thiocarbonyl groups as ring members; and/or may contain a ring-fused phenyl ring which is unsubstituted or substituted; or $R^2$ and $R^3$ with the group N-$(A)_n$ to which they are attached form a saturated 3- to 7-membered heterocycle which, in addition to the nitrogen atom, may contain 1, 2 or a further 3 heteroatoms selected from the group consisting of oxygen, nitrogen, sulfur and a group $NR^{10}$ and, if appropriate, 1, 2 or 3 carbonyl groups and/or thiocarbonyl groups as ring members;

$R^a$, $R^b$, $R^c$, $R^d$ and $R^e$ independently of one another are hydrogen, OH, CN, $NO_2$, halogen, $C_1$-$C_{10}$-alkyl, $C_3$-$C_6$-cycloalkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-alkoxy, $C_1$-$C_4$-haloalkoxy, $C_1$-$C_6$-alkylthio, $C_1$-$C_4$-haloalkylthio, C(O)R$^4$, COOR$^5$, NR$^6$R$^7$, C(O)NR$^8$R$^9$, S(O)$_2$NR$^8$R$^9$, S(O)R$^{11}$, S(O)$_2$R$^{11}$ or $C_1$-$C_4$-alkoxy-$C_1$-$C_6$-alkyl; or two adjacent radicals R$^a$ to R$^e$ together with the atoms to which they are attached form a 5-, 6- or 7-membered saturated or unsaturated ring which may contain one or two heteroatoms selected from the group consisting of nitrogen, oxygen, sulfur and a group NR$^{10}$ as ring-forming atom and/or may carry one, two, three or four radicals selected from the group consisting of halogen and $C_1$-$C_4$-alkyl;

X, Y independently of one another are oxygen or sulfur;
n is 0 or 1;
A is O, S(O)$_k$ or NR$^{12}$, where k is 0, 1 or 2;
R$^4$, R$^8$, R$^9$ independently of one another are hydrogen or $C_1$-$C_4$-alkyl;
R$^5$, R$^{11}$ are $C_1$-$C_4$-alkyl;
R$^6$, R$^7$ independently of one another are hydrogen, $C_1$-$C_6$-alkyl, $C_3$-$C_6$-alkenyl, $C_3$-$C_6$-alkynyl, C(O)R$^4$, COOR$^5$ or S(O)$_2$R$^{11}$;
R$^{10}$, R$^{12}$ independently of one another are hydrogen, $C_1$-$C_6$-alkyl, $C_3$-$C_6$-alkenyl or $C_3$-$C_6$-alkynyl; and
R$^{13}$ is phenyl which is unsubstituted or carries 1, 2, 3 or 4 substituents, where the substituents are selected from the group consisting of halogen, nitro, cyano, OH, alkyl, alkoxy, haloalkyl, haloalkoxy, COOR$^5$, NR$^6$R$^7$ and C(O)NR$^8$R$^9$.

Accordingly, the present invention relates to 1-phenylpyrrolidin-2-one-3-carboxamides of the formula I and their agriculturally useful salts.

Moreover, the present invention relates to
the use of compounds I and/or their salts as herbicides;
crop protection compositions comprising at least one 1-phenylpyrrolidin-2-one-3-carboxamide of the formula I and/or at least one agriculturally useful salt of I as active substances; and
methods for controlling unwanted vegetation, which comprises allowing a herbicidally effective amount of at least one 1-phenylpyrrolidin-2-one-3-carboxamide of the formula I or an agriculturally useful salt of I to act on plants, their habitat or on seed.

Depending on the substitution pattern, the compounds of the formula I may contain one or more centers of chirality, in which case they are present as mixtures of enantiomers or diastereomers. The invention provides both the pure enantiomers or diastereomers and their mixtures. The invention also provides tautomers of compounds of the formula I.

If R$^1$ represents hydrogen, the 1-phenylpyrrolidin-2-one-3-carboxamides of the formula I according to the invention can be present in the form of their agriculturally useful salts. In general, agriculturally useful salts are the salts of those bases or cations which have no adverse effect on the herbicidal action of the compounds I. Thus, suitable basic salts are in particular the salts of the alkali metals, preferably of sodium and potassium, of the alkaline earth metals, preferably of calcium, magnesium and barium, and of the transition metals, preferably of manganese, copper, zinc and iron, and also ammonium salts where the ammonium ion may, if desired, carry one to four $C_1$-$C_4$-alkyl substituents, $C_1$-$C_4$-hydroxyalkyl substituents, $C_1$-$C_4$-alkoxy-$C_1$-$C_4$-alkyl substituents and/or one phenyl or benzyl substituent, preferably diisopropylammonium, tetramethylammonium, tetrabutylammonium, trimethylbenzylammonium, trimethyl-2-hydroxyethylammonium, bis(2-hydroxyethyl)methylammonium, tris(2-hydroxyethyl)ammonium, bis(2-hydroxyethyl)-dimethylammonium, tris(2-hydroxyethyl)methylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

The organic moieties mentioned in the definition of the substituents R$^1$ to R$^{12}$ or as radicals on heterocyclic rings are—like the term halo—collective terms for individual listings of the individual group members. All carbon chains, i.e. all alkyl, haloalkyl, cyanoalkyl, aminoalkyl, aminocarbonylalkyl, alkoxy, haloalkoxy, alkylthio, haloalkylthio, alkylsulfinyl, alkylsulfonyl, alkynyl and alkenyl moieties, may be straight-chain or branched. Halogenated substituents preferably carry one to five identical or different halogen atoms. The term halo denotes in each case fluorine, chlorine, bromine or iodine.

Examples of other meanings are:

$C_1$-$C_4$-alkyl: for example methyl, ethyl, propyl, 1-methylethyl, butyl, 1-methylpropyl, 2-methylpropyl or 1,1-dimethylethyl;

$C_1$-$C_6$-alkyl: $C_1$-$C_4$-alkyl as mentioned above and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$-$C_{10}$-alkyl: $C_1$-$C_6$-alkyl as mentioned above and also, for example, n-heptyl, 2-heptyl, 2-methylhexyl, n-octyl, 1-methylheptyl, 2-ethylhexyl, n-nonyl, 2-nonyl, n-decyl, 2-decyl, 2-propylheptyl and the like;

$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl; in particular difluoromethyl, trifluoromethyl;

$C_1$-$C_6$-haloalkyl: $C_1$-$C_4$-haloalkyl as mentioned above and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$-$C_2$-fluoroalkyl: $C_1$-$C_2$-alkyl which carries 1, 2, 3, 4 or 5 fluorine atoms, for example difluoromethyl, trifluoromethyl, 2-fluoroethyl, 2,2-difluoroethyl, 2,2,2-trifluoroethyl, 1,1,2,2-tetrafluoroethyl and pentafluoroethyl;

$C_1$-$C_2$-fluoroalkoxy: $C_1$-$C_2$-alkoxy which carries 1, 2, 3, 4 or 5 fluorine atoms, for example difluoromethoxy, trifluoromethoxy, 2-fluoroethoxy, 2,2-difluoroethoxy, 2,2,2-trifluoroethoxy, 1,1,2,2-tetrafluoroethoxy and pentafluoroethoxy;

$C_1$-$C_4$-alkoxy: for example methoxy, ethoxy, n-propoxy, 1-methylethoxy, butoxy, 1-methylpropoxy, 2-methylpropoxy or 1,1-dimethylethoxy;

$C_1$-$C_6$-alkoxy: $C_1$-$C_4$-alkoxy as mentioned above and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$ or $OCHF_3$;

$C_1$-$C_4$-alkoxy-$C_1$-$C_6$-alkyl: $C_1$-$C_6$-alkyl which is substituted by $C_1$-$C_6$-alkoxy—as mentioned above—, i.e., for example, $CH_2$—$OCH_3$, $CH_2$—$OC_2H_5$, n-propoxymethyl, $CH_2$—$OCH(CH_3)$ 2, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, 2-(1-methylethoxy)pentyl, 2-(n-butoxy)pentyl, 2-(1-methylpropoxy)pentyl, 2-(2-methylpropoxy)pentyl, 2-(1,1-dimethylethoxy)pentyl, 3-(methoxy)pentyl, 3-(ethoxy)pentyl, 3-(n-propoxy)pentyl, 3-(1-methylethoxy)pentyl, 3-(n-butoxy)pentyl, 3-(1-methylpropoxy)pentyl, 3-(2-methylpropoxy)pentyl, 3-(1,1-dimethylethoxy)pentyl, 4-(methoxy)pentyl, 4-(ethoxy)pentyl, 4-(n-propoxy)pentyl, 4-(1-methylethoxy)pentyl, 4-(n-butoxy)pentyl, 4-(1-methylpropoxy)pentyl, 4-(2-methylpropoxy)pentyl, 4-(1,1-dimethylethoxy)pentyl, 4-(methoxy)pentyl, 5-(ethoxy)pentyl, 5-(n-propoxy)pentyl, 5-(1-methylethoxy)pentyl, 5-(n-butoxy)pentyl, 5-(1-methylpropoxy)pentyl, 5-(2-methylpropoxy)pentyl, 5-(1,1-dimethylethoxy)pentyl, 2-(1-methylethoxy)hexyl, 2-(n-butoxy)hexyl, 2-(1-methylpropoxy)hexyl, 2-(2-methylpropoxy)hexyl, 2-(1,1-dimethylethoxy)hexyl, 3-(methoxy)hexyl, 3-(ethoxy)hexyl, 3-(n-propoxy)hexyl, 3-(1-methylethoxy)hexyl, 3-(n-butoxy)hexyl, 3-(1-methylpropoxy)hexyl, 3-(2-methylpropoxy)hexyl 3-(1,1-dimethylethoxy)hexyl, 4-(methoxy)hexyl, 4-(ethoxy)hexyl, 4-(n-propoxy)hexyl, 4-(1-methylethoxy)hexyl, 4-(n-butoxy)hexyl, 4-(1-methylpropoxy)hexyl, 4-(2-methylpropoxy)hexyl, 4-(1,1-dimethylethoxy)hexyl, 4-(methoxy)hexyl, 5-(ethoxy)hexyl, 5-(n-propoxy)hexyl, 5-(1-methylethoxy)hexyl, 5-(n-butoxy)hexyl, 5-(1-methylpropoxy)hexyl, 5-(2-methylpropoxy)hexyl, 5-(1,1-dimethylethoxy)hexyl, 6-(ethoxy)hexyl, 6-(n-propoxy)hexyl, 6-(1-methylethoxy)hexyl, 6-(n-butoxy)hexyl, 6-(1-methylpropoxy)hexyl, 6-(2-methylpropoxy)hexyl, 6-(1,1-dimethylethoxy)hexyl;

$C_1$-$C_4$-alkylthio: an alkylsulfanyl radical having 1 to 4 carbon atoms, for example $SCH_3$, $SC_2H_5$, $SCH_2$—$C_2H_5$, $SCH(CH_3)_2$, n-butylthio, $SCH(CH_3)$—$C_2H_5$, $SCH_2$—$CH(CH_3)$ 2 or $SC(CH_3)$ 3;

$C_1$-$C_6$-alkylthio: $C_1$-$C_4$-alkylthio as mentioned above and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$-$C_4$-haloalkylthio: a $C_1$-$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

phenyl-$C_1$-$C_4$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)eth-1-yl, 1-(benzyl)-1-(methyl)eth-1-yl or 1-(benzyl)prop-1-yl;

$C_2$-$C_6$-alkenyl: a monounsaturated aliphatic hydrocarbon radical having 2 to 6 and in particular 2 to 4 carbon atoms, for example ethenyl, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_3$-$C_8$-alkenyl: an aliphatic hydrocarbon radical which contains a C=C double bond and has 3 to 8, preferably 3 to 6 and in particular 3 or 4 carbon atoms as mentioned above, which is preferably not attached via a carbon atom of the double bond, for example one of the radicals mentioned under $C_2$-$C_6$-alkenyl and also 1-hepten-3-yl, 1-hepten-4-yl, 1-hepten-5-yl, 1-hepten-6-yl, 1-hepten-7-yl, 3-hepten-1-yl, 2-hepten-4-yl, 3-hepten-5-yl, 3-hepten-6-yl, 3-hepten-7-yl, 1-octen-3-yl, 1-octen-4-yl, 1-octen-5-yl, 1-octen-6-yl, 1-octen-7-yl, 1-octen-8-yl, 3-octen-1-yl, 2-octen-1-yl, 2-octen-4-yl, 3-octen-5-yl, 3-octen-6-yl, 3-octen-7-yl, 3-octen-8-yl and the like;

$C_2$-$C_6$-haloalkenyl: $C_2$-$C_6$-alkenyl as mentioned above which is partially or fully substituted by fluorine, chlorine, and/or bromine, i.e., for example, 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl;

$C_2$-$C_6$-alkynyl: an aliphatic hydrocarbon radical which contains a C≡C triple bond and has 2 to 6 and in particular 2 to 4 carbon atoms: for example ethynyl, propargyl (2-propynyl), 1-propynyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_3$-$C_{10}$-alkynyl: an aliphatic hydrocarbon radical which contains a triple bond and has 3 to 10, preferably 3 to 6 and in particular 3 or 4 carbon atoms as mentioned above, which is preferably not attached via a carbon atom of the triple bond, for example one of the radicals mentioned under $C_2$-$C_6$-alkynyl and also 1-heptyn-3-yl, 1-heptyn-4-yl, 1-heptyn-5-yl, 1-heptyn-6-yl, 1-heptyn-7-yl, 3-heptyn-1-yl, 2-heptyn-4-yl, 3-heptyn-5-yl, 3-heptyn-6-yl, 3-heptyn-7-yl, 1-octyn-3-yl, 1-octyn-4-yl, 1-octyn-5-yl, 1-octyn-6-yl, 1-octyn-7-yl, 1-octyn-8-yl, 3-octyn-1-yl, 2-octyn-1-yl, 2-octyn-4-yl, 3-octyn-5-yl, 3-octyn-6-yl, 3-octyn-7-yl, 3-octyn-8-yl and the like;

$C_3$-$C_{10}$-cycloalkyl: a monocyclic hydrocarbon radical having 3 to 10 carbon atoms, in particular 3 to 8 carbon atoms and especially 3 to 6 carbon atoms, for example cyclopropyl, cyclobutyl, cyclopentyl, cyclohexyl, cycloheptyl or cyclooctyl;

$C_7$-$C_{10}$-polycycloalkyl: a bicyclic, tricyclic or tetracyclic hydrocarbon radical having 7 to 10 carbon atoms, for example bicyclo[2.2.1]-hept-1-yl, bicyclo[2.2.1]hept-2-yl, bicyclo[2.2.1]hept-7-yl, bicyclo[2.2.2]oct-1-yl, bicyclo[2.2.2]oct-2-yl or adamantan-1-yl;

$C_3$-$C_8$-cycloalkyl-$C_1$-$C_4$-alkyl: $C_1$-$C_4$-alkyl which carries a $C_3$-$C_8$-cycloalkyl radical as defined above, for example cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl, 1-cyclopropylbut-2-yl, 2-cyclopropylbut-2-yl, 3-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-(methyl)eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 4-cyclohexylbut-2-yl, 1-(cyclohexylmethyl)eth-1-yl, 1-(cyclohexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 4-cycloheptylbut-2-yl, 1-(cycloheptylmethyl)eth-1-yl, 1-(cycloheptylmethyl)-1-(methyl)eth-1-yl, 1-(cycloheptylmethyl)prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-(methyl)eth-1-yl or 1-(cyclooctylmethyl)prop-1-yl, preferably cyclopropylmethyl, cyclobutylmethyl, cyclopentylmethyl or cyclohexylmethyl.

$C_5$-$C_{10}$-cycloalkenyl: a mono- or bicyclic hydrocarbon radical having 5 to 10 carbon atoms, in particular 5 to 8 carbon atoms and especially 5 to 6 carbon atoms and which contains a C=C double bond, for example cyclopenten-1-yl, cyclopenten-3-yl, cyclohexen-1-yl, cyclohexen-3-yl, cyclohexen-4-yl, cyclohepten-1-yl, cyclohepten-3-yl, cyclohepten-4-yl, cycloocten-1-yl, cycloocten-3-yl, cycloocten-4-yl, cycloocten-5-yl, bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl;

unsubstituted or substituted phenyl: a phenyl group which is unsubstituted or carries 1, 2, 3 or 4 substituents, where the substituents are selected from the group consisting of halogen, nitro, cyano, OH, alkyl, alkoxy, haloalkyl, haloalkoxy, COOR$^5$, NR$^6$R$^7$, C(O)NR$^8$R$^9$;

3- to 7-membered heterocyclyl: a heterocyclic radical which has 3, 4, 5, 6 or 7 ring members, where 1, 2 or 3 of the ring members are heteroatoms selected from the group consisting of oxygen, nitrogen, sulfur, a group SO$_2$ and a group NR$^{10}$. Moreover, the heterocycle may optionally contain 1, 2 or 3 carbonyl groups and/or thiocarbonyl groups as ring members. The heterocycle may furthermore contain a ring-fused unsubstituted or substituted phenyl ring. The heterocycle may be aromatic (heteroaryl) or partially or fully saturated.

Examples of saturated heterocycles are: oxiran-1-yl, aziridin-1-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-6-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles are:
dihydrofuran-2-yl, 1,2-oxazolin-3-yl, 1,2-oxazolin-5-yl, 1,3-oxazolin-2-yl;

Examples of aromatic heterocyclyl are the 5- and 6-membered aromatic, heterocyclic radicals, for example furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

If the radicals R$^2$ and R$^3$ together with the nitrogen atom to which they are attached form a saturated heterocycle, n is preferably 0. In this case, the saturated heterocycle is selected, for example, from the group consisting of 1,3-oxazolidin-3-yl, 1,2-oxazolidin-2-yl, pyrrolidin-1-yl, pyrrolidin-2-on-1-yl, tetrahydropyrazol-1-yl, 2-methyltetrahydropyrazol-1-yl, piperidin-1-yl, piperidin-2-on-1-yl, morpholin-4-yl, hexahydropyrimidin-1-yl, piperazin-1-yl, 4-methylpiperazin-1-yl, hexahydro-1,3,5-triazin-1-yl, 3,5-dimethyltriazin-1-yl, hexahydroazepin-1-yl, hexahydroazepin-2-on-1-yl, hexahydro-1,3-diazepin-1-yl, hexahydro-1,4-diazepin-1-yl, in particular from the group consisting of pyrrolidin-1-yl, piperidin-1-yl and morpholin-4-yl.

If two adjacent radicals R$^a$ to R$^e$ together with the atoms to which they are attached form a 5-, 6- or 7-membered saturated or unsaturated ring which may contain one or two heteroatoms selected from the group consisting of nitrogen, oxygen, sulfur and a group NR$^{10}$ as ring-forming atom(s) and/or may carry one, two, three or four radicals selected from the group consisting of halogen and $C_1$-$C_4$-alkyl, two adjacent radicals R$^a$ to R$^e$, for example R$^b$ and R$^c$ or R$^c$ and R$^d$, together are a 3-, 4- or 5-membered saturated or unsaturated carbon chain in which one or two non-adjacent carbon atoms of the chain may be replaced by heteroatoms selected from the group consisting of O, N, a group NR$^{10}$ and S and in which the carbon atoms of the chain may carry one, two, three or four substituents selected from the group consisting of halogen and $C_1$-$C_4$-alkyl. For example, two adjacent radicals R$^a$ to R$^e$ may be a chain of the formula —O—CH$_2$—O—, —O—(CH$_2$)$_2$—O—, —O—(CH$_2$)$_2$—, —O—(CH$_2$)$_3$—, —(CH$_2$)$_3$—, —(CH$_2$)$_4$— or —(CH$_2$)$_5$—

With a view to the use of the compounds of the formula I according to the invention as herbicides, the variables $R^1$, $R^2$, $R^3$, X, Y, A, n, $R^a$, $R^b$, $R^c$, $R^d$ and $R^e$ are preferably as defined below, independently of one another and in particular in combination:

$R^1$ is hydrogen, OH, Cl, Br, $C_1$-$C_6$-alkyl or $OC(O)R^4$, particularly preferably hydrogen;

$R^2$ is $C_1$-$C_{10}$-alkyl, $C_3$-$C_8$-cycloalkyl, $C_3$-$C_8$-alkenyl, $C_3$-$C_8$-alkynyl, $C_3$-$C_8$-cycloalkyl, $C_5$-$C_8$-cycloalkenyl or $C_3$-$C_8$-cycloalkyl-$C_1$-$C_4$-alkyl, where $C_1$-$C_{10}$-alkyl and $C_3$-$C_8$-cycloalkyl may be partially or fully halogenated and/or may carry one or two radicals selected from the group consisting of $C_1$-$C_6$-alkoxy, $C_1$-$C_4$-haloalkoxy, $C_1$-$C_6$-alkylthio, $C_1$-$C_4$-haloalkylthio, unsubstituted or substituted phenyl, $COOR^5$, $NR^6R^7$, $C(O)NR^8R^9$, phenyl which may be unsubstituted or substituted by 1, 2 or 3 substituents selected from the group consisting of halogen, nitro, OH, CN, $C_1$-$C_6$-alkyl, $C_1$-$C_6$-alkoxy, $C_1$-$C_4$-haloalkoxy, $C_1$-$C_6$-alkylthio, $C_1$-$C_4$-haloalkylthio, unsubstituted or substituted phenyl, $COOR^5$, $NR^6R^7$, $C(O)NR^8R^9$. In particular, $R^2$ is $C_1$-$C_6$-alkyl, $C_3$-$C_6$-cycloalkyl, $C_3$-$C_6$-alkenyl, $C_3$-$C_6$-alkynyl, $C_5$-$C_6$-cycloalkenyl, $C_3$-$C_6$-cycloalkyl-$C_1$-$C_4$-alkyl or unsubstituted or substituted phenyl, where $C_1$-$C_6$-alkyl and $C_3$-$C_6$-cycloalkyl may be partially or fully halogenated and/or may carry one or two, in particular one, radical selected from the group consisting of $C_1$-$C_6$-alkoxy, $C_1$-$C_4$-haloalkoxy, $C_1$-$C_6$-alkylthio, $C_1$-$C_4$-haloalkylthio, unsubstituted or substituted phenyl, $COOR^5$, $NR^6R^7$, $C(O)NR^8R^9$. Particularly preferably, $R^2$ is $C_1$-$C_6$-alkyl, $C_3$-$C_8$-cycloalkyl, unsubstituted or substituted phenyl, phenylalkyl or $C_3$-$C_8$-cycloalkyl-$C_1$-$C_4$-alkyl;

$R^3$ is hydrogen or $C_1$-$C_6$-alkyl;

X is oxygen;

Y is oxygen; and

A if present, is oxygen, a group N—$R^{12}$, where $R^{12}$=hydrogen or alkyl, or a group $SO_2$;

n is 0;

$R^a$, $R^b$, $R^c$, $R^d$, $R^e$ are hydrogen, halogen, CN, $C_1$-$C_4$-alkyl, $C_1$-$C_4$-haloalkyl, $C_1$-$C_4$-alkoxy, $C_1$-$C_4$-haloalkoxy, in particular halogen, CN, $C_1$-$C_4$-alkyl, $C_1$-$C_2$-fluoroalkyl and $C_1$-$C_2$-fluoroalkoxy and especially fluorine, chlorine, bromine, CN, $C_1$-$C_4$-alkyl, methoxy, $CF_3$, $CHF_2$, $OCF_3$ and $OCHF_2$.

With a view to the use as herbicides, preference is given to 1-phenylpyrrolidin-2-one-3-carboxamides of the formula I according to the invention where not more than 3 of the radicals $R^a$, $R^b$, $R^c$, $R^d$ and $R^e$ and in particular 3 or 4 of the abovementioned radicals are different from hydrogen. Particular preference is given to 1-phenylpyrrolidin-2-one-3-carboxamides of the formula I where at least $R^b$ and/or $R^d$ are different from hydrogen. In this case, the other radicals $R^a$-$R^e$, at least one of the radicals $R^a$ and $R^e$ and especially both radicals $R^a$ and $R^e$ are particularly preferably hydrogen. Particular preference is also given to compounds of the formula I in which $R^b$ and $R^c$ or $R^d$ and $R^c$ are different from hydrogen and the other radicals of the radicals $R^a$-$R^e$ are hydrogen. Another preferred embodiment of the invention relates to compounds in which the radicals $R^a$ and $R^e$ or $R^a$ and $R^b$ or $R^a$ and $R^c$ are different from hydrogen and the other radicals of the radicals $R^a$-$R^e$ are hydrogen.

Preferred radicals $R^a$, $R^b$, $R^c$, $R^d$, $R^e$ are, in addition to hydrogen, the substituents halogen, CN, $C_1$-$C_4$-alkyl, $C_1$-$C_4$-haloalkyl, $C_1$-$C_4$-alkoxy, $C_1$-$C_4$-haloalkoxy, in particular halogen, CN, $C_1$-$C_4$-alkyl, $C_1$-$C_2$-fluoroalkyl and $C_1$-$C_2$-fluoroalkoxy and especially fluorine, chlorine, bromine, CN, $C_1$-$C_4$-alkyl, methoxy, $CF_3$, $CHF_2$, $OCF_3$ and $OCHF_2$.

A particularly preferred group of compounds of the formula I are those compounds in which $R^a$ and $R^e$ are hydrogen. Here, the radical

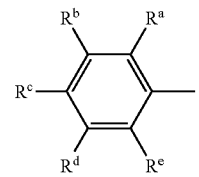

denotes, for example, a group of the formulae Q1 to Q31:

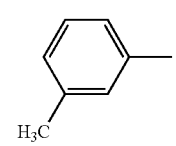
Q1

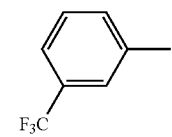
Q2

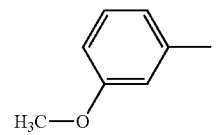
Q3

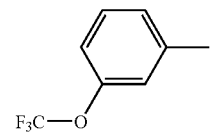
Q4

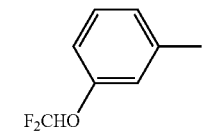
Q5

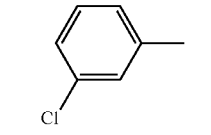
Q6

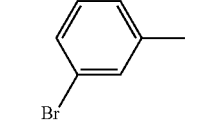
Q7

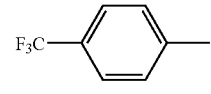
Q8

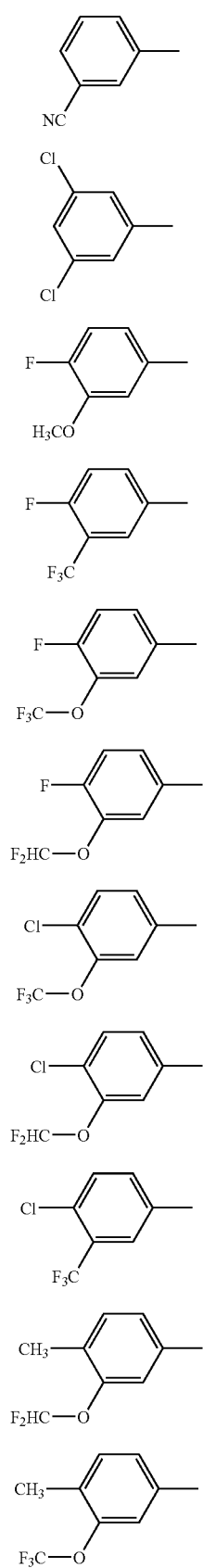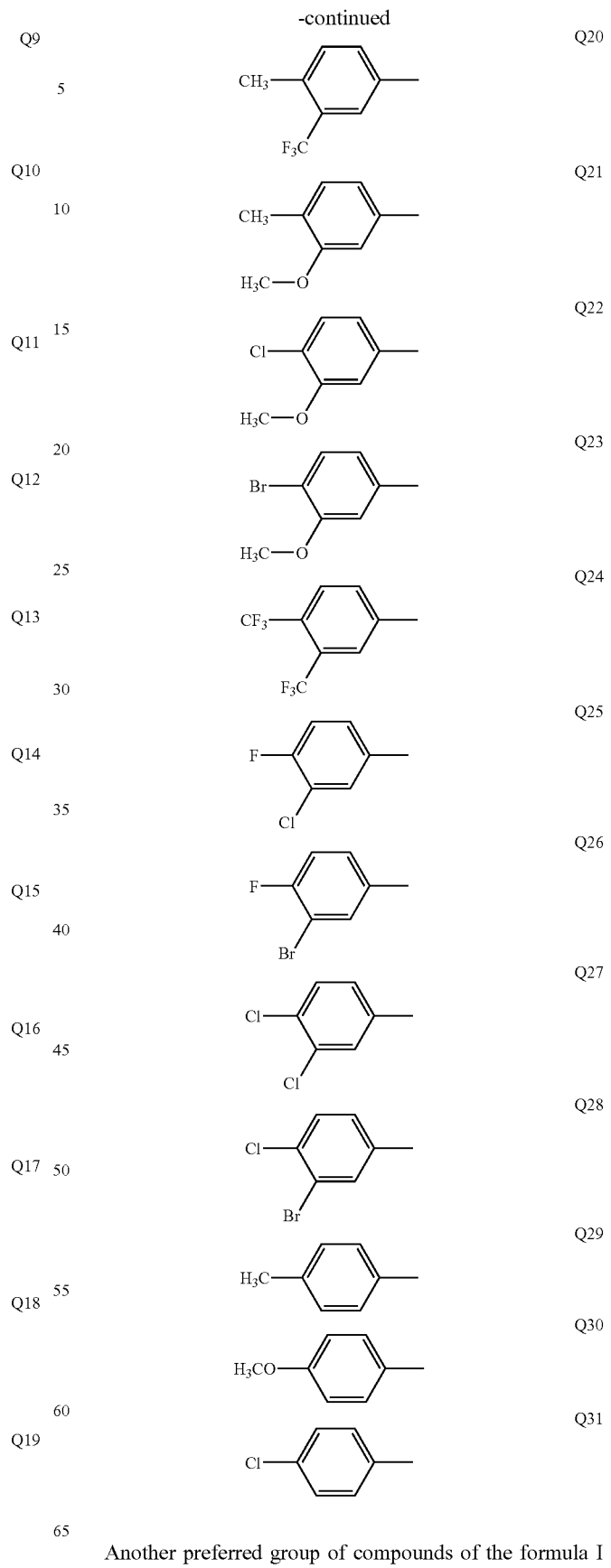
Another preferred group of compounds of the formula I are those compounds in which $R^a$ and, if appropriate, one of the radicals $R^b$, $R^c$ or $R^e$ are different from hydrogen and the other radicals $R^a$-$R^e$ are hydrogen. Here, the radical

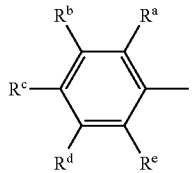

denotes, for example, a group of the formulae Q32 to Q39:

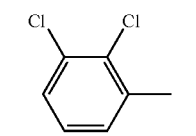
Q32

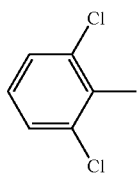
Q33

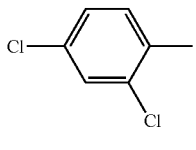
Q34

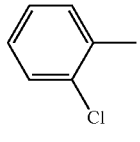
Q35

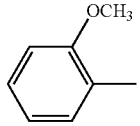
Q36

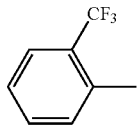
Q37

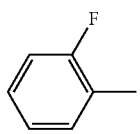
Q38

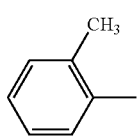
Q39

Particular preference is given to the 1-phenylpyrrolidin-2-one-3-carboxamides of the formula Ia ($\equiv$I where $R^a$=$R^b$=H, X=O, Y=O, $R^1$=H, $R^3$=$CH_3$ and n=0) where $R^b$, $R^c$, $R^d$ and $R^2$ have the meanings mentioned above, in particular the meanings mentioned as being preferred. Examples of such compounds are the compounds Ia.1 to Ia.1717 in which the variables $R^b$, $R^c$, $R^d$ and $R^2$ together have the meanings given in one row of Table 1.

TABLE 1

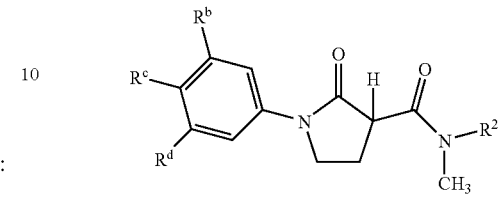
(Ia)

| No. | $R^b$ | $R^c$ | $R^d$ | $R^2$ |
|---|---|---|---|---|
| 1. | Cl | H | H | H |
| 2. | Br | H | H | H |
| 3. | F | H | H | H |
| 4. | $CH_3$ | H | H | H |
| 5. | $C_2H_5$ | H | H | H |
| 6. | $CH(CH_3)_2$ | H | H | H |
| 7. | $OCH_3$ | H | H | H |
| 8. | CN | H | H | H |
| 9. | $CF_3$ | H | H | H |
| 10. | $OCF_3$ | H | H | H |
| 11. | $OCHF_2$ | H | H | H |
| 12. | Cl | H | H | $CH_3$ |
| 13. | Br | H | H | $CH_3$ |
| 14. | F | H | H | $CH_3$ |
| 15. | $CH_3$ | H | H | $CH_3$ |
| 16. | $C_2H_5$ | H | H | $CH_3$ |
| 17. | $CH(CH_3)_2$ | H | H | $CH_3$ |
| 18. | $OCH_3$ | H | H | $CH_3$ |
| 19. | CN | H | H | $CH_3$ |
| 20. | $CF_3$ | H | H | $CH_3$ |
| 21. | $OCF_3$ | H | H | $CH_3$ |
| 22. | $OCHF_2$ | H | H | $CH_3$ |
| 23. | Cl | H | H | $C_2H_5$ |
| 24. | Br | H | H | $C_2H_5$ |
| 25. | F | H | H | $C_2H_5$ |
| 26. | $CH_3$ | H | H | $C_2H_5$ |
| 27. | $C_2H_5$ | H | H | $C_2H_5$ |
| 28. | $CH(CH_3)_2$ | H | H | $C_2H_5$ |
| 29. | $OCH_3$ | H | H | $C_2H_5$ |
| 30. | CN | H | H | $C_2H_5$ |
| 31. | $CF_3$ | H | H | $C_2H_5$ |
| 32. | $OCF_3$ | H | H | $C_2H_5$ |
| 33. | $OCHF_2$ | H | H | $C_2H_5$ |
| 34. | Cl | H | H | n-$C_3H_7$ |
| 35. | Br | H | H | n-$C_3H_7$ |
| 36. | F | H | H | n-$C_3H_7$ |
| 37. | $CH_3$ | H | H | n-$C_3H_7$ |
| 38. | $C_2H_5$ | H | H | n-$C_3H_7$ |
| 39. | $CH(CH_3)_2$ | H | H | n-$C_3H_7$ |
| 40. | $OCH_3$ | H | H | n-$C_3H_7$ |
| 41. | CN | H | H | n-$C_3H_7$ |
| 42. | $CF_3$ | H | H | n-$C_3H_7$ |
| 43. | $OCF_3$ | H | H | n-$C_3H_7$ |
| 44. | $OCHF_2$ | H | H | n-$C_3H_7$ |
| 45. | Cl | H | H | $CH(CH_3)_2$ |
| 46. | Br | H | H | $CH(CH_3)_2$ |
| 47. | F | H | H | $CH(CH_3)_2$ |
| 48. | $CH_3$ | H | H | $CH(CH_3)_2$ |
| 49. | $C_2H_5$ | H | H | $CH(CH_3)_2$ |
| 50. | $CH(CH_3)_2$ | H | H | $CH(CH_3)_2$ |
| 51. | $OCH_3$ | H | H | $CH(CH_3)_2$ |
| 52. | CN | H | H | $CH(CH_3)_2$ |
| 53. | $CF_3$ | H | H | $CH(CH_3)_2$ |
| 54. | $OCF_3$ | H | H | $CH(CH_3)_2$ |
| 55. | $OCHF_2$ | H | H | $CH(CH_3)_2$ |
| 56. | Cl | H | H | n-$C_4H_9$ |
| 57. | Br | H | H | n-$C_4H_9$ |
| 58. | F | H | H | n-$C_4H_9$ |
| 59. | $CH_3$ | H | H | n-$C_4H_9$ |
| 60. | $C_2H_5$ | H | H | n-$C_4H_9$ |
| 61. | $CH(CH_3)_2$ | H | H | n-$C_4H_9$ |

TABLE 1-continued (Ia)

| No. | R$^b$ | R$^c$ | R$^d$ | R$^2$ |
|---|---|---|---|---|
| 62. | OCH$_3$ | H | H | n-C$_4$H$_9$ |
| 63. | CN | H | H | n-C$_4$H$_9$ |
| 64. | CF$_3$ | H | H | n-C$_4$H$_9$ |
| 65. | OCF$_3$ | H | H | n-C$_4$H$_9$ |
| 66. | OCHF$_2$ | H | H | n-C$_4$H$_9$ |
| 67. | Cl | H | H | C(CH$_3$)$_3$ |
| 68. | Br | H | H | C(CH$_3$)$_3$ |
| 69. | F | H | H | C(CH$_3$)$_3$ |
| 70. | CH$_3$ | H | H | C(CH$_3$)$_3$ |
| 71. | C$_2$H$_5$ | H | H | C(CH$_3$)$_3$ |
| 72. | CH(CH$_3$)$_2$ | H | H | C(CH$_3$)$_3$ |
| 73. | OCH$_3$ | H | H | C(CH$_3$)$_3$ |
| 74. | CN | H | H | C(CH$_3$)$_3$ |
| 75. | CF$_3$ | H | H | C(CH$_3$)$_3$ |
| 76. | OCF$_3$ | H | H | C(CH$_3$)$_3$ |
| 77. | OCHF$_2$ | H | H | C(CH$_3$)$_3$ |
| 78. | Cl | H | H | C$_6$H$_5$ |
| 79. | Br | H | H | C$_6$H$_5$ |
| 80. | F | H | H | C$_6$H$_5$ |
| 81. | CH$_3$ | H | H | C$_6$H$_5$ |
| 82. | C$_2$H$_5$ | H | H | C$_6$H$_5$ |
| 83. | CH(CH$_3$)$_2$ | H | H | C$_6$H$_5$ |
| 84. | OCH$_3$ | H | H | C$_6$H$_5$ |
| 85. | CN | H | H | C$_6$H$_5$ |
| 86. | CF$_3$ | H | H | C$_6$H$_5$ |
| 87. | OCF$_3$ | H | H | C$_6$H$_5$ |
| 88. | OCHF$_2$ | H | H | C$_6$H$_5$ |
| 89. | Cl | H | H | cyclopropyl |
| 90. | Br | H | H | cyclopropyl |
| 91. | F | H | H | cyclopropyl |
| 92. | CH$_3$ | H | H | cyclopropyl |
| 93. | C$_2$H$_5$ | H | H | cyclopropyl |
| 94. | CH(CH$_3$)$_2$ | H | H | cyclopropyl |
| 95. | OCH$_3$ | H | H | cyclopropyl |
| 96. | CN | H | H | cyclopropyl |
| 97. | CF$_3$ | H | H | cyclopropyl |
| 98. | OCF$_3$ | H | H | cyclopropyl |
| 99. | OCHF$_2$ | H | H | cyclopropyl |
| 100. | Cl | H | H | CH$_2$-cyclopropyl |
| 101. | Br | H | H | CH$_2$-cyclopropyl |
| 102. | F | H | H | CH$_2$-cyclopropyl |
| 103. | CH$_3$ | H | H | CH$_2$-cyclopropyl |
| 104. | C$_2$H$_5$ | H | H | CH$_2$-cyclopropyl |
| 105. | CH(CH$_3$)$_2$ | H | H | CH$_2$-cyclopropyl |
| 106. | OCH$_3$ | H | H | CH$_2$-cyclopropyl |
| 107. | CN | H | H | CH$_2$-cyclopropyl |
| 108. | CF$_3$ | H | H | CH$_2$-cyclopropyl |
| 109. | OCF$_3$ | H | H | CH$_2$-cyclopropyl |
| 110. | OCHF$_2$ | H | H | CH$_2$-cyclopropyl |
| 111. | Cl | H | H | cyclobutyl |
| 112. | Br | H | H | cyclobutyl |
| 113. | F | H | H | cyclobutyl |
| 114. | CH$_3$ | H | H | cyclobutyl |
| 115. | C$_2$H$_5$ | H | H | cyclobutyl |
| 116. | CH(CH$_3$)$_2$ | H | H | cyclobutyl |
| 117. | OCH$_3$ | H | H | cyclobutyl |
| 118. | CN | H | H | cyclobutyl |
| 119. | CF$_3$ | H | H | cyclobutyl |
| 120. | OCF$_3$ | H | H | cyclobutyl |
| 121. | OCHF$_2$ | H | H | cyclobutyl |
| 122. | Cl | H | H | cyclopentyl |
| 123. | Br | H | H | cyclopentyl |
| 124. | F | H | H | cyclopentyl |
| 125. | CH$_3$ | H | H | cyclopentyl |
| 126. | C$_2$H$_5$ | H | H | cyclopentyl |
| 127. | CH(CH$_3$)$_2$ | H | H | cyclopentyl |
| 128. | OCH$_3$ | H | H | cyclopentyl |
| 129. | CN | H | H | cyclopentyl |
| 130. | CF$_3$ | H | H | cyclopentyl |
| 131. | OCF$_3$ | H | H | cyclopentyl |
| 132. | OCHF$_2$ | H | H | cyclopentyl |
| 133. | Cl | H | H | cyclohexyl |
| 134. | Br | H | H | cyclohexyl |
| 135. | F | H | H | cyclohexyl |
| 136. | CH$_3$ | H | H | cyclohexyl |
| 137. | C$_2$H$_5$ | H | H | cyclohexyl |
| 138. | CH(CH$_3$)$_2$ | H | H | cyclohexyl |
| 139. | OCH$_3$ | H | H | cyclohexyl |
| 140. | CN | H | H | cyclohexyl |
| 141. | CF$_3$ | H | H | cyclohexyl |
| 142. | OCF$_3$ | H | H | cyclohexyl |
| 143. | OCHF$_2$ | H | H | cyclohexyl |
| 144. | H | Cl | H | H |
| 145. | H | Br | H | H |
| 146. | H | F | H | H |
| 147. | H | CH$_3$ | H | H |
| 148. | H | C$_2$H$_5$ | H | H |
| 149. | H | CH(CH$_3$)$_2$ | H | H |
| 150. | H | OCH$_3$ | H | H |
| 151. | H | CN | H | H |
| 152. | H | CF$_3$ | H | H |
| 153. | H | OCF$_3$ | H | H |
| 154. | H | OCHF$_2$ | H | H |
| 155. | H | Cl | H | CH$_3$ |
| 156. | H | Br | H | CH$_3$ |
| 157. | H | F | H | CH$_3$ |
| 158. | H | CH$_3$ | H | CH$_3$ |
| 159. | H | C$_2$H$_5$ | H | CH$_3$ |
| 160. | H | CH(CH$_3$)$_2$ | H | CH$_3$ |
| 161. | H | OCH$_3$ | H | CH$_3$ |
| 162. | H | CN | H | CH$_3$ |
| 163. | H | CF$_3$ | H | CH$_3$ |
| 164. | H | OCF$_3$ | H | CH$_3$ |
| 165. | H | OCHF$_2$ | H | CH$_3$ |
| 166. | H | Cl | H | C$_2$H$_5$ |
| 167. | H | Br | H | C$_2$H$_5$ |
| 168. | H | F | H | C$_2$H$_5$ |
| 169. | H | CH$_3$ | H | C$_2$H$_5$ |
| 170. | H | C$_2$H$_5$ | H | C$_2$H$_5$ |
| 171. | H | CH(CH$_3$)$_2$ | H | C$_2$H$_5$ |
| 172. | H | OCH$_3$ | H | C$_2$H$_5$ |
| 173. | H | CN | H | C$_2$H$_5$ |
| 174. | H | CF$_3$ | H | C$_2$H$_5$ |
| 175. | H | OCF$_3$ | H | C$_2$H$_5$ |
| 176. | H | OCHF$_2$ | H | C$_2$H$_5$ |
| 177. | H | Cl | H | n-C$_3$H$_7$ |
| 178. | H | Br | H | n-C$_3$H$_7$ |
| 179. | H | F | H | n-C$_3$H$_7$ |
| 180. | H | CH$_3$ | H | n-C$_3$H$_7$ |
| 181. | H | C$_2$H$_5$ | H | n-C$_3$H$_7$ |
| 182. | H | CH(CH$_3$)$_2$ | H | n-C$_3$H$_7$ |
| 183. | H | OCH$_3$ | H | n-C$_3$H$_7$ |
| 184. | H | CN | H | n-C$_3$H$_7$ |
| 185. | H | CF$_3$ | H | n-C$_3$H$_7$ |
| 186. | H | OCF$_3$ | H | n-C$_3$H$_7$ |
| 187. | H | OCHF$_2$ | H | n-C$_3$H$_7$ |
| 188. | H | Cl | H | CH(CH$_3$)$_2$ |
| 189. | H | Br | H | CH(CH$_3$)$_2$ |
| 190. | H | F | H | CH(CH$_3$)$_2$ |
| 191. | H | CH$_3$ | H | CH(CH$_3$)$_2$ |

TABLE 1-continued (Ia)

| No. | $R^b$ | $R^c$ | $R^d$ | $R^2$ |
|---|---|---|---|---|
| 192. | H | $C_2H_5$ | H | $CH(CH_3)_2$ |
| 193. | H | $CH(CH_3)_2$ | H | $CH(CH_3)_2$ |
| 194. | H | $OCH_3$ | H | $CH(CH_3)_2$ |
| 195. | H | CN | H | $CH(CH_3)_2$ |
| 196. | H | $CF_3$ | H | $CH(CH_3)_2$ |
| 197. | H | $OCF_3$ | H | $CH(CH_3)_2$ |
| 198. | H | $OCHF_2$ | H | $CH(CH_3)_2$ |
| 199. | H | Cl | H | $n-C_4H_9$ |
| 200. | H | Br | H | $n-C_4H_9$ |
| 201. | H | F | H | $n-C_4H_9$ |
| 202. | H | $CH_3$ | H | $n-C_4H_9$ |
| 203. | H | $C_2H_5$ | H | $n-C_4H_9$ |
| 204. | H | $CH(CH_3)_2$ | H | $n-C_4H_9$ |
| 205. | H | $OCH_3$ | H | $n-C_4H_9$ |
| 206. | H | CN | H | $n-C_4H_9$ |
| 207. | H | $CF_3$ | H | $n-C_4H_9$ |
| 208. | H | $OCF_3$ | H | $n-C_4H_9$ |
| 209. | H | $OCHF_2$ | H | $n-C_4H_9$ |
| 210. | H | Cl | H | $C(CH_3)_3$ |
| 211. | H | Br | H | $C(CH_3)_3$ |
| 212. | H | F | H | $C(CH_3)_3$ |
| 213. | H | $CH_3$ | H | $C(CH_3)_3$ |
| 214. | H | $C_2H_5$ | H | $C(CH_3)_3$ |
| 215. | H | $CH(CH_3)_2$ | H | $C(CH_3)_3$ |
| 216. | H | $OCH_3$ | H | $C(CH_3)_3$ |
| 217. | H | CN | H | $C(CH_3)_3$ |
| 218. | H | $CF_3$ | H | $C(CH_3)_3$ |
| 219. | H | $OCF_3$ | H | $C(CH_3)_3$ |
| 220. | H | $OCHF_2$ | H | $C(CH_3)_3$ |
| 221. | H | Cl | H | $C_6H_5$ |
| 222. | H | Br | H | $C_6H_5$ |
| 223. | H | F | H | $C_6H_5$ |
| 224. | H | $CH_3$ | H | $C_6H_5$ |
| 225. | H | $C_2H_5$ | H | $C_6H_5$ |
| 226. | H | $CH(CH_3)_2$ | H | $C_6H_5$ |
| 227. | H | $OCH_3$ | H | $C_6H_5$ |
| 228. | H | CN | H | $C_6H_5$ |
| 229. | H | $CF_3$ | H | $C_6H_5$ |
| 230. | H | $OCF_3$ | H | $C_6H_5$ |
| 231. | H | $OCHF_2$ | H | $C_6H_5$ |
| 232. | H | Cl | H | cyclopropyl |
| 233. | H | Br | H | cyclopropyl |
| 234. | H | F | H | cyclopropyl |
| 235. | H | $CH_3$ | H | cyclopropyl |
| 236. | H | $C_2H_5$ | H | cyclopropyl |
| 237. | H | $CH(CH_3)_2$ | H | cyclopropyl |
| 238. | H | $OCH_3$ | H | cyclopropyl |
| 239. | H | CN | H | cyclopropyl |
| 240. | H | $CF_3$ | H | cyclopropyl |
| 241. | H | $OCF_3$ | H | cyclopropyl |
| 242. | H | $OCHF_2$ | H | cyclopropyl |
| 243. | H | Cl | H | $CH_2$-cyclopropyl |
| 244. | H | Br | H | $CH_2$-cyclopropyl |
| 245. | H | F | H | $CH_2$-cyclopropyl |
| 246. | H | $CH_3$ | H | $CH_2$-cyclopropyl |
| 247. | H | $C_2H_5$ | H | $CH_2$-cyclopropyl |
| 248. | H | $CH(CH_3)_2$ | H | $CH_2$-cyclopropyl |
| 249. | H | $OCH_3$ | H | $CH_2$-cyclopropyl |
| 250. | H | CN | H | $CH_2$-cyclopropyl |
| 251. | H | $CF_3$ | H | $CH_2$-cyclopropyl |
| 252. | H | $OCF_3$ | H | $CH_2$-cyclopropyl |
| 253. | H | $OCHF_2$ | H | $CH_2$-cyclopropyl |
| 254. | H | Cl | H | cyclobutyl |
| 255. | H | Br | H | cyclobutyl |
| 256. | H | F | H | cyclobutyl |
| 257. | H | $CH_3$ | H | cyclobutyl |
| 258. | H | $C_2H_5$ | H | cyclobutyl |
| 259. | H | $CH(CH_3)_2$ | H | cyclobuty). |
| 260. | H | $OCH_3$ | H | cyclobutyl |
| 261. | H | CN | H | cyclobutyl |
| 262. | H | $CF_3$ | H | cyclobutyl |
| 263. | H | $OCF_3$ | H | cyclobutyl |
| 264. | H | $OCHF_2$ | H | cyclobutyl |
| 265. | H | Cl | H | cyclopentyl |
| 266. | H | Br | H | cyclopentyl |
| 267. | H | F | H | cyclopentyl |
| 268. | H | $CH_3$ | H | cyclopentyl |
| 269. | H | $C_2H_5$ | H | cyclopentyl |
| 270. | H | $CH(CH_3)_2$ | H | cyclopentyl |
| 271. | H | $OCH_3$ | H | cyclopentyl |
| 272. | H | CN | H | cyclopentyl |
| 273. | H | $CF_3$ | H | cyclopentyl |
| 274. | H | $OCF_3$ | H | cyclopentyl |
| 275. | H | $OCHF_2$ | H | cyclopentyl |
| 276. | H | Cl | H | cyclohexyl |
| 277. | H | Br | H | cyclohexyl |
| 278. | H | F | H | cyclohexyl |
| 279. | H | $CH_3$ | H | cyclohexyl |
| 280. | H | $C_2H_5$ | H | cyclohexyl |
| 281. | H | $CH(CH_3)_2$ | H | cyclohexyl |
| 282. | H | $OCH_3$ | H | cyclohexyl |
| 283. | H | CN | H | cyclohexyl |
| 284. | H | $CF_3$ | H | cyclohexyl |
| 285. | H | $OCF_3$ | H | cyclohexyl |
| 286. | H | $OCHF_2$ | H | cyclohexyl |
| 287. | $CF_3$ | Br | H | H |
| 288. | $CF_3$ | $OCH_3$ | H | H |
| 289. | $CF_3$ | Cl | H | H |
| 290. | $CF_3$ | F | H | H |
| 291. | $CF_3$ | $CH_3$ | H | H |
| 292. | $CF_3$ | $C_2H_5$ | H | H |
| 293. | $CF_3$ | $CF_3$ | H | H |
| 294. | $CF_3$ | $OCF_3$ | H | H |
| 295. | $CF_3$ | $OCHF_2$ | H | H |
| 296. | $CF_3$ | Br | H | $CH_3$ |
| 297. | $CF_3$ | $OCH_3$ | H | $CH_3$ |
| 298. | $CF_3$ | Cl | H | $CH_3$ |
| 299. | $CF_3$ | F | H | $CH_3$ |
| 300. | $CF_3$ | $CH_3$ | H | $CH_3$ |
| 301. | $CF_3$ | $C_2H_5$ | H | $CH_3$ |
| 302. | $CF_3$ | $CF_3$ | H | $CH_3$ |
| 303. | $CF_3$ | $OCF_3$ | H | $CH_3$ |
| 304. | $CF_3$ | $OCHF_2$ | H | $CH_3$ |
| 305. | $CF_3$ | Br | H | $C_2H_5$ |
| 306. | $CF_3$ | $OCH_3$ | H | $C_2H_5$ |
| 307. | $CF_3$ | Cl | H | $C_2H_5$ |
| 308. | $CF_3$ | F | H | $C_2H_5$ |
| 309. | $CF_3$ | $CH_3$ | H | $C_2H_5$ |
| 310. | $CF_3$ | $C_2H_5$ | H | $C_2H_5$ |
| 311. | $CF_3$ | $CF_3$ | H | $C_2H_5$ |
| 312. | $CF_3$ | $OCF_3$ | H | $C_2H_5$ |
| 313. | $CF_3$ | $OCHF_2$ | H | $C_2H_5$ |
| 314. | $CF_3$ | Br | H | $n-C_3H_7$ |
| 315. | $CF_3$ | $OCH_3$ | H | $n-C_3H_7$ |
| 316. | $CF_3$ | Cl | H | $n-C_3H_7$ |
| 317. | $CF_3$ | F | H | $n-C_3H_7$ |
| 318. | $CF_3$ | $CH_3$ | H | $n-C_3H_7$ |
| 319. | $CF_3$ | $C_2H_5$ | H | $n-C_3H_7$ |
| 320. | $CF_3$ | $CF_3$ | H | $n-C_3H_7$ |
| 321. | $CF_3$ | $OCF_3$ | H | $n-C_3H_7$ |

TABLE 1-continued (Ia)

| No. | R$^b$ | R$^c$ | R$^d$ | R$^2$ |
|---|---|---|---|---|
| 322. | CF$_3$ | OCHF$_2$ | H | n-C$_3$H$_7$ |
| 323. | CF$_3$ | Br | H | CH(CH$_3$)$_2$ |
| 324. | CF$_3$ | OCH$_3$ | H | CH(CH$_3$)$_2$ |
| 325. | CF$_3$ | Cl | H | CH(CH$_3$)$_2$ |
| 326. | CF$_3$ | F | H | CH(CH$_3$)$_2$ |
| 327. | CF$_3$ | CH$_3$ | H | CH(CH$_3$)$_2$ |
| 328. | CF$_3$ | C$_2$H$_5$ | H | CH(CH$_3$)$_2$ |
| 329. | CF$_3$ | CF$_3$ | H | CH(CH$_3$)$_2$ |
| 330. | CF$_3$ | OCF$_3$ | H | CH(CH$_3$)$_2$ |
| 331. | CF$_3$ | OCHF$_2$ | H | CH(CH$_3$)$_2$ |
| 332. | CF$_3$ | Br | H | n-C$_4$H$_9$ |
| 333. | CF$_3$ | OCH$_3$ | H | n-C$_4$H$_9$ |
| 334. | CF$_3$ | Cl | H | n-C$_4$H$_9$ |
| 335. | CF$_3$ | F | H | n-C$_4$H$_9$ |
| 336. | CF$_3$ | CH$_3$ | H | n-C$_4$H$_9$ |
| 337. | CF$_3$ | C$_2$H$_5$ | H | n-C$_4$H$_9$ |
| 338. | CF$_3$ | CF$_3$ | H | n-C$_4$H$_9$ |
| 339. | CF$_3$ | OCF$_3$ | H | n-C$_4$H$_9$ |
| 340. | CF$_3$ | OCHF$_2$ | H | n-C$_4$H$_9$ |
| 341. | CF$_3$ | Br | H | C(CH$_3$)$_3$ |
| 342. | CF$_3$ | OCH$_3$ | H | C(CH$_3$)$_3$ |
| 343. | CF$_3$ | Cl | H | C(CH$_3$)$_3$ |
| 344. | CF$_3$ | F | H | C(CH$_3$)$_3$ |
| 345. | CF$_3$ | CH$_3$ | H | C(CH$_3$)$_3$ |
| 346. | CF$_3$ | C$_2$H$_5$ | H | C(CH$_3$)$_3$ |
| 347. | CF$_3$ | CF$_3$ | H | C(CH$_3$)$_3$ |
| 348. | CF$_3$ | OCF$_3$ | H | C(CH$_3$)$_3$ |
| 349. | CF$_3$ | OCHF$_2$ | H | C(CH$_3$)$_3$ |
| 350. | CF$_3$ | Br | H | C$_6$H$_5$ |
| 351. | CF$_3$ | OCH$_3$ | H | C$_6$H$_5$ |
| 352. | CF$_3$ | Cl | H | C$_6$H$_5$ |
| 353. | CF$_3$ | F | H | C$_6$H$_5$ |
| 354. | CF$_3$ | CH$_3$ | H | C$_6$H$_5$ |
| 355. | CF$_3$ | C$_2$H$_5$ | H | C$_6$H$_5$ |
| 356. | CF$_3$ | CF$_3$ | H | C$_6$H$_5$ |
| 357. | CF$_3$ | OCF$_3$ | H | C$_6$H$_5$ |
| 358. | CF$_3$ | OCHF$_2$ | H | C$_6$H$_5$ |
| 359. | CF$_3$ | Br | H | cyclopropyl |
| 360. | CF$_3$ | OCH$_3$ | H | cyclopropyl |
| 361. | CF$_3$ | Cl | H | cyclopropyl |
| 362. | CF$_3$ | F | H | cyclopropyl |
| 363. | CF$_3$ | CH$_3$ | H | cyclopropyl |
| 364. | CF$_3$ | C$_2$H$_5$ | H | cyclopropyl |
| 365. | CF$_3$ | CF$_3$ | H | cyclopropyl |
| 366. | CF$_3$ | OCF$_3$ | H | cyclopropyl |
| 367. | CF$_3$ | OCHF$_2$ | H | cyclopropyl |
| 368. | CF$_3$ | Br | H | CH$_2$-cyclopropyl |
| 369. | CF$_3$ | OCH$_3$ | H | CH$_2$-cyclopropyl |
| 370. | CF$_3$ | Cl | H | CH$_2$-cyclopropyl |
| 371. | CF$_3$ | F | H | CH$_2$-cyclopropyl |
| 372. | CF$_3$ | CH$_3$ | H | CH$_2$-cyclopropyl |
| 373. | CF$_3$ | C$_2$H$_5$ | H | CH$_2$-cyclopropyl |
| 374. | CF$_3$ | CF$_3$ | H | CH$_2$-cyclopropyl |
| 375. | CF$_3$ | OCF$_3$ | H | CH$_2$-cyclopropyl |
| 376. | CF$_3$ | OCHF$_2$ | H | CH$_2$-cyclopropyl |
| 377. | CF$_3$ | Br | H | cyclobutyl |
| 378. | CF$_3$ | OCH$_3$ | H | cyclobutyl |
| 379. | CF$_3$ | Cl | H | cyclobutyl |
| 380. | CF$_3$ | F | H | cyclobutyl |
| 381. | CF$_3$ | CH$_3$ | H | cyclobutyl |
| 382. | CF$_3$ | C$_2$H$_5$ | H | cyclobutyl |
| 383. | CF$_3$ | CF$_3$ | H | cyclobutyl |
| 384. | CF$_3$ | OCF$_3$ | H | cyclobutyl |
| 385. | CF$_3$ | OCHF$_2$ | H | cyclobutyl |
| 386. | CF$_3$ | Br | H | cyclopentyl |
| 387. | CF$_3$ | OCH$_3$ | H | cyclopentyl |
| 388. | CF$_3$ | Cl | H | cyclopentyl |
| 389. | CF$_3$ | F | H | cyclopentyl |
| 390. | CF$_3$ | CH$_3$ | H | cyclopentyl |
| 391. | CF$_3$ | C$_2$H$_5$ | H | cyclopentyl |
| 392. | CF$_3$ | CF$_3$ | H | cyclopentyl |
| 393. | CF$_3$ | OCF$_3$ | H | cyclopentyl |
| 394. | CF$_3$ | OCHF$_2$ | H | cyclopentyl |
| 395. | CF$_3$ | Br | H | cyclohexyl |
| 396. | CF$_3$ | OCH$_3$ | H | cyclohexyl |
| 397. | CF$_3$ | Cl | H | cyclohexyl |
| 398. | CF$_3$ | F | H | cyclohexyl |
| 399. | CF$_3$ | CH$_3$ | H | cyclohexyl |
| 400. | CF$_3$ | C$_2$H$_5$ | H | cyclohexyl |
| 401. | CF$_3$ | CF$_3$ | H | cyclohexyl |
| 402. | CF$_3$ | OCF$_3$ | H | cyclohexyl |
| 403. | CF$_3$ | OCHF$_2$ | H | cyclohexyl |
| 404. | CF$_3$ | H | Br | H |
| 405. | CF$_3$ | H | OCH$_3$ | H |
| 406. | CF$_3$ | H | Cl | H |
| 407. | CF$_3$ | H | F | H |
| 408. | CF$_3$ | H | CH$_3$ | H |
| 409. | CF$_3$ | H | C$_2$H$_5$ | H |
| 410. | CF$_3$ | H | CF$_3$ | H |
| 411. | CF$_3$ | H | OCF$_3$ | H |
| 412. | CF$_3$ | H | OCHF$_2$ | H |
| 413. | CF$_3$ | H | Br | CH$_3$ |
| 414. | CF$_3$ | H | OCH$_3$ | CH$_3$ |
| 415. | CF$_3$ | H | Cl | CH$_3$ |
| 416. | CF$_3$ | H | F | CH$_3$ |
| 417. | CF$_3$ | H | CH$_3$ | CH$_3$ |
| 418. | CF$_3$ | H | C$_2$H$_5$ | CH$_3$ |
| 419. | CF$_3$ | H | CF$_3$ | CH$_3$ |
| 420. | CF$_3$ | H | OCF$_3$ | CH$_3$ |
| 421. | CF$_3$ | H | OCHF$_2$ | CH$_3$ |
| 422. | CF$_3$ | H | Br | C$_2$H$_5$ |
| 423. | CF$_3$ | H | OCH$_3$ | C$_2$H$_5$ |
| 424. | CF$_3$ | H | Cl | C$_2$H$_5$ |
| 425. | CF$_3$ | H | F | C$_2$H$_5$ |
| 426. | CF$_3$ | H | CH$_3$ | C$_2$H$_5$ |
| 427. | CF$_3$ | H | C$_2$H$_5$ | C$_2$H$_5$ |
| 428. | CF$_3$ | H | CF$_3$ | C$_2$H$_5$ |
| 429. | CF$_3$ | H | OCF$_3$ | C$_2$H$_5$ |
| 430. | CF$_3$ | H | OCHF$_2$ | C$_2$H$_5$ |
| 431. | CF$_3$ | H | Br | n-C$_3$H$_7$ |
| 432. | CF$_3$ | H | OCH$_3$ | n-C$_3$H$_7$ |
| 433. | CF$_3$ | H | Cl | n-C$_3$H$_7$ |
| 434. | CF$_3$ | H | F | n-C$_3$H$_7$ |
| 435. | CF$_3$ | H | CH$_3$ | n-C$_3$H$_7$ |
| 436. | CF$_3$ | H | C$_2$H$_5$ | n-C$_3$H$_7$ |
| 437. | CF$_3$ | H | CF$_3$ | n-C$_3$H$_7$ |
| 438. | CF$_3$ | H | OCF$_3$ | n-C$_3$H$_7$ |
| 439. | CF$_3$ | H | OCHF$_2$ | n-C$_3$H$_7$ |
| 440. | CF$_3$ | H | Br | CH(CH$_3$)$_2$ |
| 441. | CF$_3$ | H | OCH$_3$ | CH(CH$_3$)$_2$ |
| 442. | CF$_3$ | H | Cl | CH(CH$_3$)$_2$ |
| 443. | CF$_3$ | H | F | CH(CH$_3$)$_2$ |
| 444. | CF$_3$ | H | CH$_3$ | CH(CH$_3$)$_2$ |
| 445. | CF$_3$ | H | C$_2$H$_5$ | CH(CH$_3$)$_2$ |
| 446. | CF$_3$ | H | CF$_3$ | CH(CH$_3$)$_2$ |
| 447. | CF$_3$ | H | OCF$_3$ | CH(CH$_3$)$_2$ |
| 448. | CF$_3$ | H | OCHF$_2$ | CH(CH$_3$)$_2$ |
| 449. | CF$_3$ | H | Br | n-C$_4$H$_9$ |
| 450. | CF$_3$ | H | OCH$_3$ | n-C$_4$H$_9$ |
| 451. | CF$_3$ | H | Cl | n-C$_4$H$_9$ |

TABLE 1-continued (Ia)

| No. | $R^b$ | $R^c$ | $R^d$ | $R^2$ |
|---|---|---|---|---|
| 452. | $CF_3$ | H | F | n-$C_4H_9$ |
| 453. | $CF_3$ | H | $CH_3$ | n-$C_4H_9$ |
| 454. | $CF_3$ | H | $C_2H_5$ | n-$C_4H_9$ |
| 455. | $CF_3$ | H | $CF_3$ | n-$C_4H_9$ |
| 456. | $CF_3$ | H | $OCF_3$ | n-$C_4H_9$ |
| 457. | $CF_3$ | H | $OCHF_2$ | n-$C_4H_9$ |
| 458. | $CF_3$ | H | Br | $C(CH_3)_3$ |
| 459. | $CF_3$ | H | $OCH_3$ | $C(CH_3)_3$ |
| 460. | $CF_3$ | H | Cl | $C(CH_3)_3$ |
| 461. | $CF_3$ | H | F | $C(CH_3)_3$ |
| 462. | $CF_3$ | H | $CH_3$ | $C(CH_3)_3$ |
| 463. | $CF_3$ | H | $C_2H_5$ | $C(CH_3)_3$ |
| 464. | $CF_3$ | H | $CF_3$ | $C(CH_3)_3$ |
| 465. | $CF_3$ | H | $OCF_3$ | $C(CH_3)_3$ |
| 466. | $CF_3$ | H | $OCHF_2$ | $C(CH_3)_3$ |
| 467. | $CF_3$ | H | Br | $C_6H_5$ |
| 468. | $CF_3$ | H | $OCH_3$ | $C_6H_5$ |
| 469. | $CF_3$ | H | Cl | $C_6H_5$ |
| 470. | $CF_3$ | H | F | $C_6H_5$ |
| 471. | $CF_3$ | H | $CH_3$ | $C_6H_5$ |
| 472. | $CF_3$ | H | $C_2H_5$ | $C_6H_5$ |
| 473. | $CF_3$ | H | $CF_3$ | $C_6H_5$ |
| 474. | $CF_3$ | H | $OCF_3$ | $C_6H_5$ |
| 475. | $CF_3$ | H | $OCHF_2$ | $C_6H_5$ |
| 476. | $CF_3$ | H | Br | cyclopropyl |
| 477. | $CF_3$ | H | $OCH_3$ | cyclopropyl |
| 478. | $CF_3$ | H | Cl | cyclopropyl |
| 479. | $CF_3$ | H | F | cyclopropyl |
| 480. | $CF_3$ | H | $CH_3$ | cyclopropyl |
| 481. | $CF_3$ | H | $C_2H_5$ | cyclopropyl |
| 482. | $CF_3$ | H | $CF_3$ | cyclopropyl |
| 483. | $CF_3$ | H | $OCF_3$ | cyclopropyl |
| 484. | $CF_3$ | H | $OCHF_2$ | cyclopropyl |
| 485. | $CF_3$ | H | Br | $CH_2$-cyclopropyl |
| 486. | $CF_3$ | H | $OCH_3$ | $CH_2$-cyclopropyl |
| 487. | $CF_3$ | H | Cl | $CH_2$-cyclopropyl |
| 488. | $CF_3$ | H | F | $CH_2$-cyclopropyl |
| 489. | $CF_3$ | H | $CH_3$ | $CH_2$-cyclopropyl |
| 490. | $CF_3$ | H | $C_2H_5$ | $CH_2$-cyclopropyl |
| 491. | $CF_3$ | H | $CF_3$ | $CH_2$-cyclopropyl |
| 492. | $CF_3$ | H | $OCF_3$ | $CH_2$-cyclopropyl |
| 493. | $CF_3$ | H | $OCHF_2$ | $CH_2$-cyclopropyl |
| 494. | $CF_3$ | H | Br | cyclobutyl |
| 495. | $CF_3$ | H | $OCH_3$ | cyclobutyl |
| 496. | $CF_3$ | H | Cl | cyclobutyl |
| 497. | $CF_3$ | H | F | cyclobutyl |
| 498. | $CF_3$ | H | $CH_3$ | cyclobutyl |
| 499. | $CF_3$ | H | $C_2H_5$ | cyclobutyl |
| 500. | $CF_3$ | H | $CF_3$ | cyclobutyl |
| 501. | $CF_3$ | H | $OCF_3$ | cyclobutyl |
| 502. | $CF_3$ | H | $OCHF_2$ | cyclobutyl |
| 503. | $CF_3$ | H | Br | cyclopentyl |
| 504. | $CF_3$ | H | $OCH_3$ | cyclopentyl |
| 505. | $CF_3$ | H | Cl | cyclopentyl |
| 506. | $CF_3$ | H | F | cyclopentyl |
| 507. | $CF_3$ | H | $CH_3$ | cyclopentyl |
| 508. | $CF_3$ | H | $C_2H_5$ | cyclopentyl |
| 509. | $CF_3$ | H | $CF_3$ | cyclopentyl |
| 510. | $CF_3$ | H | $OCF_3$ | cyclopentyl |
| 511. | $CF_3$ | H | $OCHF_2$ | cyclopentyl |
| 512. | $CF_3$ | H | Br | cyclohexyl |
| 513. | $CF_3$ | H | $OCH_3$ | cyclohexyl |
| 514. | $CF_3$ | H | Cl | cyclohexyl |
| 515. | $CF_3$ | H | F | cyclohexyl |
| 516. | $CF_3$ | H | $CH_3$ | cyclohexyl |
| 517. | $CF_3$ | H | $C_2H_5$ | cyclohexyl |
| 518. | $CF_3$ | H | $CF_3$ | cyclohexyl |
| 519. | $CF_3$ | H | $OCF_3$ | cyclohexyl |
| 520. | $CF_3$ | H | $OCHF_2$ | cyclohexyl |
| 521. | $OCF_3$ | Br | H | H |
| 522. | $OCF_3$ | $OCH_3$ | H | H |
| 523. | $OCF_3$ | Cl | H | H |
| 524. | $OCF_3$ | F | H | H |
| 525. | $OCF_3$ | $CH_3$ | H | H |
| 526. | $OCF_3$ | $C_2H_5$ | H | H |
| 527. | $OCF_3$ | $CF_3$ | H | H |
| 528. | $OCF_3$ | $OCF_3$ | H | H |
| 529. | $OCF_3$ | $OCHF_2$ | H | H |
| 530. | $OCF_3$ | Br | H | $CH_3$ |
| 531. | $OCF_3$ | $OCH_3$ | H | $CH_3$ |
| 532. | $OCF_3$ | Cl | H | $CH_3$ |
| 533. | $OCF_3$ | F | H | $CH_3$ |
| 534. | $OCF_3$ | Cl3 | H | $CH_3$ |
| 535. | $OCF_3$ | $C_2H_5$ | H | $CH_3$ |
| 536. | $OCF_3$ | $CF_3$ | H | $CH_3$ |
| 537. | $OCF_3$ | $OCF_3$ | H | $CH_3$ |
| 538. | $OCF_3$ | $OCHF_2$ | H | $CH_3$ |
| 539. | $OCF_3$ | Br | H | $C_2H_5$ |
| 540. | $OCF_3$ | $OCH_3$ | H | $C_2H_5$ |
| 541. | $OCF_3$ | Cl | H | $C_2H_5$ |
| 542. | $OCF_3$ | F | H | $C_2H_5$ |
| 543. | $OCF_3$ | $CH_3$ | H | $C_2H_5$ |
| 544. | $OCF_3$ | $C_2H_5$ | H | $C_2H_5$ |
| 545. | $OCF_3$ | $CF_3$ | H | $C_2H_5$ |
| 546. | $OCF_3$ | $OCF_3$ | H | $C_2H_5$ |
| 547. | $OCF_3$ | $OCHF_2$ | H | $C_2H_5$ |
| 548. | $OCF_3$ | Br | H | n-$C_3H_7$ |
| 549. | $OCF_3$ | $OCH_3$ | H | n-$C_3H_7$ |
| 550. | $OCF_3$ | Cl | H | n-$C_3H_7$ |
| 551. | $OCF_3$ | F | H | n-$C_3H_7$ |
| 552. | $OCF_3$ | $CH_3$ | H | n-$C_3H_7$ |
| 553. | $OCF_3$ | $C_2H_5$ | H | n-$C_3H_7$ |
| 554. | $OCF_3$ | $CF_3$ | H | n-$C_3H_7$ |
| 555. | $OCF_3$ | $OCF_3$ | H | n-$C_3H_7$ |
| 556. | $OCF_3$ | $OCHF_2$ | H | n-$C_3H_7$ |
| 557. | $OCF_3$ | Br | H | $CH(CH_3)_2$ |
| 558. | $OCF_3$ | $OCH_3$ | H | $CH(CH_3)_2$ |
| 559. | $OCF_3$ | Cl | H | $CH(CH_3)_2$ |
| 560. | $OCF_3$ | F | H | $CH(CH_3)_2$ |
| 561. | $OCF_3$ | $CH_3$ | H | $CH(CH_3)_2$ |
| 562. | $OCF_3$ | $C_2H_5$ | H | $CH(CH_3)_2$ |
| 563. | $OCF_3$ | $CF_3$ | H | $CH(CH_3)_2$ |
| 564. | $OCF_3$ | $OCF_3$ | H | $CH(CH_3)_2$ |
| 565. | $OCF_3$ | $OCHF_2$ | H | $CH(CH_3)_2$ |
| 566. | $OCF_3$ | Br | H | n-$C_4H_9$ |
| 567. | $OCF_3$ | $OCH_3$ | H | n-$C_4H_9$ |
| 568. | $OCF_3$ | Cl | H | n-$C_4H_9$ |
| 569. | $OCF_3$ | F | H | n-$C_4H_9$ |
| 570. | $OCF_3$ | $CH_3$ | H | n-$C_4H_9$ |
| 571. | $OCF_3$ | $C_2H_5$ | H | n-$C_4H_9$ |
| 572. | $OCF_3$ | $CF_3$ | H | n-$C_4H_9$ |
| 573. | $OCF_3$ | $OCF_3$ | H | n-$C_4H_9$ |
| 574. | $OCF_3$ | $OCHF_2$ | H | n-$C_4H_9$ |
| 575. | $OCF_3$ | Br | H | $C(CH_3)_3$ |
| 576. | $OCF_3$ | $OCH_3$ | H | $C(CH_3)_3$ |
| 577. | $OCF_3$ | Cl | H | $C(CH_3)_3$ |
| 578. | $OCF_3$ | F | H | $C(CH_3)_3$ |
| 579. | $OCF_3$ | $CH_3$ | H | $C(CH_3)_3$ |
| 580. | $OCF_3$ | $C_2H_5$ | H | $C(CH_3)_3$ |
| 581. | $OCF_3$ | $CF_3$ | H | $C(CH_3)_3$ |

TABLE 1-continued (Ia)

| No. | $R^b$ | $R^c$ | $R^d$ | $R^2$ |
|---|---|---|---|---|
| 582. | $OCF_3$ | $OCF_3$ | H | $C(CH_3)_3$ |
| 583. | $OCF_3$ | $OCHF_2$ | H | $C(CH_3)_3$ |
| 584. | $OCF_3$ | Br | H | $C_6H_5$ |
| 585. | $OCF_3$ | $OCH_3$ | H | $C_6H_5$ |
| 586. | $OCF_3$ | Cl | H | $C_6H_5$ |
| 587. | $OCF_3$ | F | H | $C_6H_5$ |
| 588. | $OCF_3$ | $CH_3$ | H | $C_6H_5$ |
| 589. | $OCF_3$ | $C_2H_5$ | H | $C_6H_5$ |
| 590. | $OCF_3$ | $CF_3$ | H | $C_6H_5$ |
| 591. | $OCF_3$ | $OCF_3$ | H | $C_6H_5$ |
| 592. | $OCF_3$ | $OCHF_2$ | H | $C_6H_5$ |
| 593. | $OCF_3$ | Br | H | cyclopropyl |
| 594. | $OCF_3$ | $OCH_3$ | H | cyclopropyl |
| 595. | $OCF_3$ | Cl | H | cyclopropyl |
| 596. | $OCF_3$ | F | H | cyclopropyl |
| 597. | $OCF_3$ | $CH_3$ | H | cyclopropyl |
| 598. | $OCF_3$ | $C_2H_5$ | H | cyclopropyl |
| 599. | $OCF_3$ | $CF_3$ | H | cyclopropyl |
| 600. | $OCF_3$ | $OCF_3$ | H | cyclopropyl |
| 601. | $OCF_3$ | $OCHF_2$ | H | cyclopropyl |
| 602. | $OCF_3$ | Br | H | $CH_2$-cyclopropyl |
| 603. | $OCF_3$ | $OCH_3$ | H | $CH_2$-cyclopropyl |
| 604. | $OCF_3$ | Cl | H | $CH_2$-cyclopropyl |
| 605. | $OCF_3$ | F | H | $CH_2$-cyclopropyl |
| 606. | $OCF_3$ | $CH_3$ | H | $CH_2$-cyclopropyl |
| 607. | $OCF_3$ | $C_2H_5$ | H | $CH_2$-cyclopropyl |
| 608. | $OCF_3$ | $OCF_3$ | H | $CH_2$-cyclopropyl |
| 609. | $OCF_3$ | $CF_3$ | H | $CH_2$-cyclopropyl |
| 610. | $OCF_3$ | $OCHF_2$ | H | $CH_2$-cyclopropyl |
| 611. | $OCF_3$ | Br | H | cyclobutyl |
| 612. | $OCF_3$ | $OCH_3$ | H | cyclobutyl |
| 613. | $OCF_3$ | Cl | H | cyclobutyl |
| 614. | $OCF_3$ | F | H | cyclobutyl |
| 615. | $OCF_3$ | $CH_3$ | H | cyclobutyl |
| 616. | $OCF_3$ | $C_2H_5$ | H | cyclobutyl |
| 617. | $OCF_3$ | $OCF_3$ | H | cyclobutyl |
| 618. | $OCF_3$ | $CF_3$ | H | cyclobutyl |
| 619. | $OCF_3$ | $OCHF_2$ | H | cyclobutyl |
| 620. | $OCF_3$ | Br | H | cyclopentyl |
| 621. | $OCF_3$ | $OCH_3$ | H | cyclopentyl |
| 622. | $OCF_3$ | Cl | H | cyclopentyl |
| 623. | $OCF_3$ | F | H | cyclopentyl |
| 624. | $OCF_3$ | $CH_3$ | H | cyclopentyl |
| 625. | $OCF_3$ | $C_2H_5$ | H | cyclopentyl |
| 626. | $OCF_3$ | $OCF_3$ | H | cyclopentyl |
| 627. | $OCF_3$ | $CF_3$ | H | cyclopentyl |
| 628. | $OCF_3$ | $OCHF_2$ | H | cyclopentyl |
| 629. | $OCF_3$ | Br | H | cyclohexyl |
| 630. | $OCF_3$ | $OCH_3$ | H | cyclohexyl |
| 631. | $OCF_3$ | Cl | H | cyclohexyl |
| 632. | $OCF_3$ | F | H | cyclohexyl |
| 633. | $OCF_3$ | $CH_3$ | H | cyclohexyl |
| 634. | $OCF_3$ | $C_2H_5$ | H | cyclohexyl |
| 635. | $OCF_3$ | $OCF_3$ | H | cyclohexyl |
| 636. | $OCF_3$ | $CF_3$ | H | cyclohexyl |
| 637. | $OCF_3$ | $OCHF_2$ | H | cyclohexyl |
| 638. | $OCF_3$ | H | Br | H |
| 639. | $OCF_3$ | H | $OCH_3$ | H |
| 640. | $OCF_3$ | H | Cl | H |
| 641. | $OCF_3$ | H | F | H |
| 642. | $OCF_3$ | H | $CH_3$ | H |
| 643. | $OCF_3$ | H | $C_2H_5$ | H |
| 644. | $OCF_3$ | H | $CF_3$ | H |
| 645. | $OCF_3$ | H | $OCF_3$ | H |
| 646. | $OCF_3$ | H | $OCHF_2$ | H |
| 647. | $OCF_3$ | H | Br | $CH_3$ |
| 648. | $OCF_3$ | H | $OCH_3$ | $CH_3$ |
| 649. | $OCF_3$ | H | Cl | $CH_3$ |
| 650. | $OCF_3$ | H | F | $CH_3$ |
| 651. | $OCF_3$ | H | $CH_3$ | $CH_3$ |
| 652. | $OCF_3$ | H | $C_2H_5$ | $CH_3$ |
| 653. | $OCF_3$ | H | $CF_3$ | $CH_3$ |
| 654. | $OCF_3$ | H | $OCF_3$ | $CH_3$ |
| 655. | $OCF_3$ | H | $OCHF_2$ | $CH_3$ |
| 656. | $OCF_3$ | H | Br | $C_2H_5$ |
| 657. | $OCF_3$ | H | $OCH_3$ | $C_2H_5$ |
| 658. | $OCF_3$ | H | Cl | $C_2H_5$ |
| 659. | $OCF_3$ | H | F | $C_2H_5$ |
| 660. | $OCF_3$ | H | $CH_3$ | $C_2H_5$ |
| 661. | $OCF_3$ | H | $C_2H_5$ | $C_2H_5$ |
| 662. | $OCF_3$ | H | $CF_3$ | $C_2H_5$ |
| 663. | $OCF_3$ | H | $OCF_3$ | $C_2H_5$ |
| 664. | $OCF_3$ | H | $OCHF_2$ | $C_2H_5$ |
| 665. | $OCF_3$ | H | Br | $n-C_3H_7$ |
| 666. | $OCF_3$ | H | $OCH_3$ | $n-C_3H_7$ |
| 667. | $OCF_3$ | H | Cl | $n-C_3H_7$ |
| 668. | $OCF_3$ | H | F | $n-C_3H_7$ |
| 669. | $OCF_3$ | H | $CH_3$ | $n-C_3H_7$ |
| 670. | $OCF_3$ | H | $C_2H_5$ | $n-C_3H_7$ |
| 671. | $OCF_3$ | H | $CF_3$ | $n-C_3H_7$ |
| 672. | $OCF_3$ | H | $OCF_3$ | $n-C_3H_7$ |
| 673. | $OCF_3$ | H | $OCHF_2$ | $n-C_3H_7$ |
| 674. | $OCF_3$ | H | Br | $CH(CH_3)_2$ |
| 675. | $OCF_3$ | H | $OCH_3$ | $CH(CH_3)_2$ |
| 676. | $OCF_3$ | H | Cl | $CH(CH_3)_2$ |
| 677. | $OCF_3$ | H | F | $CH(CH_3)_2$ |
| 678. | $OCF_3$ | H | $CH_3$ | $CH(CH_3)_2$ |
| 679. | $OCF_3$ | H | $C_2H_5$ | $CH(CH_3)_2$ |
| 680. | $OCF_3$ | H | $CF_3$ | $CH(CH_3)_2$ |
| 681. | $OCF_3$ | H | $OCF_3$ | $CH(CH_3)_2$ |
| 682. | $OCF_3$ | H | $OCHF_2$ | $CH(CH_3)_2$ |
| 683. | $OCF_3$ | H | Br | $n-C_4H_9$ |
| 684. | $OCF_3$ | H | $OCH_3$ | $n-C_4H_9$ |
| 685. | $OCF_3$ | H | Cl | $n-C_4H_9$ |
| 686. | $OCF_3$ | H | F | $n-C_4H_9$ |
| 687. | $OCF_3$ | H | $CH_3$ | $n-C_4H_9$ |
| 688. | $OCF_3$ | H | $C_2H_5$ | $n-C_4H_9$ |
| 689. | $OCF_3$ | H | $CF_3$ | $n-C_4H_9$ |
| 690. | $OCF_3$ | H | $OCF_3$ | $n-C_4H_9$ |
| 691. | $OCF_3$ | H | $OCHF_2$ | $n-C_4H_9$ |
| 692. | $OCF_3$ | H | Br | $C(CH_3)_3$ |
| 693. | $OCF_3$ | H | $OCH_3$ | $C(CH_3)_3$ |
| 694. | $OCF_3$ | H | Cl | $C(CH_3)_3$ |
| 695. | $OCF_3$ | H | F | $C(CH_3)_3$ |
| 696. | $OCF_3$ | H | $CH_3$ | $C(CH_3)_3$ |
| 697. | $OCF_3$ | H | $C_2H_5$ | $C(CH_3)_3$ |
| 698. | $OCF_3$ | H | $CF_3$ | $C(CH_3)_3$ |
| 699. | $OCF_3$ | H | $OCF_3$ | $C(CH_3)_3$ |
| 700. | $OCF_3$ | H | $OCHF_2$ | $C(CH_3)_3$ |
| 701. | $OCF_3$ | H | Br | $C_6H_5$ |
| 702. | $OCF_3$ | H | $OCH_3$ | $C_6H_5$ |
| 703. | $OCF_3$ | H | Cl | $C_6H_5$ |
| 704. | $OCF_3$ | H | F | $C_6H_5$ |
| 705. | $OCF_3$ | H | $CH_3$ | $C_6H_5$ |
| 706. | $OCF_3$ | H | $C_2H_5$ | $C_6H_5$ |
| 707. | $OCF_3$ | H | $CF_3$ | $C_6H_5$ |
| 708. | $OCF_3$ | H | $OCF_3$ | $C_6H_5$ |
| 709. | $OCF_3$ | H | $OCHF_2$ | $C_6H_5$ |
| 710. | $OCF_3$ | H | Br | cyclopropyl |
| 711. | $OCF_3$ | H | $OCH_3$ | cyclopropyl |

TABLE 1-continued (Ia)

| No. | $R^b$ | $R^c$ | $R^d$ | $R^2$ |
|---|---|---|---|---|
| 712. | OCF$_3$ | H | Cl | cyclopropyl |
| 713. | OCF$_3$ | H | F | cyclopropyl |
| 714. | OCF$_3$ | H | CH$_3$ | cyclopropyl |
| 715. | OCF$_3$ | H | C$_2$H$_5$ | cyclopropyl |
| 716. | OCF$_3$ | H | CF$_3$ | cyclopropyl |
| 717. | OCF$_3$ | H | OCF$_3$ | cyclopropyl |
| 718. | OCF$_3$ | H | OCHF$_2$ | cyclopropyl |
| 719. | OCF$_3$ | H | Br | CH$_2$-cyclopropyl |
| 720. | OCF$_3$ | H | OCH$_3$ | CH$_2$-cyclopropyl |
| 721. | OCF$_3$ | H | Cl | CH$_2$-cyclopropyl |
| 722. | OCF$_3$ | H | F | CH$_2$-cyclopropyl |
| 723. | OCF$_3$ | H | CH$_3$ | CH$_2$-cyclopropyl |
| 724. | OCF$_3$ | H | C$_2$H$_5$ | CH$_2$-cyclopropyl |
| 725. | OCF$_3$ | H | CF$_3$ | CH$_2$-cyclopropyl |
| 726. | OCF$_3$ | H | OCF$_3$ | CH$_2$-cyclopropyl |
| 727. | OCF$_3$ | H | OCHF$_2$ | CH$_2$-cyclopropyl |
| 728. | OCF$_3$ | H | Br | cyclobutyl |
| 729. | OCF$_3$ | H | OCH$_3$ | cyclobutyl |
| 730. | OCF$_3$ | H | Cl | cyclobutyl |
| 731. | OCF$_3$ | H | F | cyclobutyl |
| 732. | OCF$_3$ | H | CH$_3$ | cyclobutyl |
| 733. | OCF$_3$ | H | C$_2$H$_5$ | cyclobutyl |
| 734. | OCF$_3$ | H | CF$_3$ | cyclobutyl |
| 735. | OCF$_3$ | H | OCF$_3$ | cyclobutyl |
| 736. | OCF$_3$ | H | OCHF$_2$ | cyclobutyl |
| 737. | OCF$_3$ | H | Br | cyclopentyl |
| 738. | OCF$_3$ | H | OCH$_3$ | cyclopentyl |
| 739. | OCF$_3$ | H | Cl | cyclopentyl |
| 740. | OCF$_3$ | H | F | cyclopentyl |
| 741. | OCF$_3$ | H | CH$_3$ | cyclopentyl |
| 742. | OCF$_3$ | H | C$_2$H$_5$ | cyclopentyl |
| 743. | OCF$_3$ | H | CF$_3$ | cyclopentyl |
| 744. | OCF$_3$ | H | OCF$_3$ | cyclopentyl |
| 745. | OCF$_3$ | H | OCHF$_2$ | cyclopentyl |
| 746. | OCF$_3$ | H | Br | cyclohexyl |
| 747. | OCF$_3$ | H | OCH$_3$ | cyclohexyl |
| 748. | OCF$_3$ | H | Cl | cyclohexyl |
| 749. | OCF$_3$ | H | F | cyclohexyl |
| 750. | OCF$_3$ | H | CH$_3$ | cyclohexyl |
| 751. | OCF$_3$ | H | C$_2$H$_5$ | cyclohexyl |
| 752. | OCF$_3$ | H | CF$_3$ | cyclohexyl |
| 753. | OCF$_3$ | H | OCF$_3$ | cyclohexyl |
| 754. | OCF$_3$ | H | OCHF$_2$ | cyclohexyl |
| 755. | OCHF$_2$ | Br | H | H |
| 756. | OCHF$_2$ | OCH$_3$ | H | H |
| 757. | OCHF$_2$ | Cl | H | H |
| 758. | OCHF$_2$ | F | H | H |
| 759. | OCHF$_2$ | CH$_3$ | H | H |
| 760. | OCHF$_2$ | C$_2$H$_5$ | H | H |
| 761. | OCHF$_2$ | OCF$_3$ | H | H |
| 762. | OCHF$_2$ | CF$_3$ | H | H |
| 763. | OCHF$_2$ | Br | H | CH$_3$ |
| 764. | OCHF$_2$ | OCH$_3$ | H | CH$_3$ |
| 765. | OCHF$_2$ | Cl | H | CH$_3$ |
| 766. | OCHF$_2$ | F | H | CH$_3$ |
| 767. | OCHF$_2$ | CH$_3$ | H | CH$_3$ |
| 768. | OCHF$_2$ | C$_2$H$_5$ | H | CH$_3$ |
| 769. | OCHF$_2$ | OCF$_3$ | H | CH$_3$ |
| 770. | OCHF$_2$ | CF$_3$ | H | CH$_3$ |
| 771. | OCHF$_2$ | Br | H | C$_2$H$_5$ |
| 772. | OCHF$_2$ | OCH$_3$ | H | C$_2$H$_5$ |
| 773. | OCHF$_2$ | Cl | H | C$_2$H$_5$ |
| 774. | OCHF$_2$ | F | H | C$_2$H$_5$ |
| 775. | OCHF$_2$ | CH$_3$ | H | C$_2$H$_5$ |
| 776. | OCHF$_2$ | C$_2$H$_5$ | H | C$_2$H$_5$ |
| 777. | OCHF$_2$ | OCF$_3$ | H | C$_2$H$_5$ |
| 778. | OCHF$_2$ | CF$_3$ | H | C$_2$H$_5$ |
| 779. | OCHF$_2$ | Br | H | n-C$_3$H$_7$ |
| 780. | OCHF$_2$ | OCH$_3$ | H | n-C$_3$H$_7$ |
| 781. | OCHF$_2$ | Cl | H | n-C$_3$H$_7$ |
| 782. | OCHF$_2$ | F | H | n-C$_3$H$_7$ |
| 783. | OCHF$_2$ | CH$_3$ | H | n-C$_3$H$_7$ |
| 784. | OCHF$_2$ | C$_2$H$_5$ | H | n-C$_3$H$_7$ |
| 785. | OCHF$_2$ | OCF$_3$ | H | n-C$_3$H$_7$ |
| 786. | OCHF$_2$ | CF$_3$ | H | n-C$_3$H$_7$ |
| 787. | OCHF$_2$ | Br | H | CH(CH$_3$)$_2$ |
| 788. | OCHF$_2$ | OCH$_3$ | H | CH(CH$_3$)$_2$ |
| 789. | OCHF$_2$ | Cl | H | CH(CH$_3$)$_2$ |
| 790. | OCHF$_2$ | F | H | CH(CH$_3$)$_2$ |
| 791. | OCHF$_2$ | CH$_3$ | H | CH(CH$_3$)$_2$ |
| 792. | OCHF$_2$ | C$_2$H$_5$ | H | CH(CH$_3$)$_2$ |
| 793. | OCHF$_2$ | OCF$_3$ | H | CH(CH$_3$)$_2$ |
| 794. | OCHF$_2$ | CF$_3$ | H | CH(CH$_3$)$_2$ |
| 795. | OCHF$_2$ | Br | H | n-C$_4$H$_9$ |
| 796. | OCHF$_2$ | OCH$_3$ | H | n-C$_4$H$_9$ |
| 797. | OCHF$_2$ | Cl | H | n-C$_4$H$_9$ |
| 798. | OCHF$_2$ | F | H | n-C$_4$H$_9$ |
| 799. | OCHF$_2$ | CH$_3$ | H | n-C$_4$H$_9$ |
| 800. | OCHF$_2$ | C$_2$H$_5$ | H | n-C$_4$H$_9$ |
| 801. | OCHF$_2$ | OCF$_3$ | H | n-C$_4$H$_9$ |
| 802. | OCHF$_2$ | CF$_3$ | H | n-C$_4$H$_9$ |
| 803. | OCHF$_2$ | Br | H | C(CH$_3$)$_3$ |
| 804. | OCHF$_2$ | OCH$_3$ | H | C(CH$_3$)$_3$ |
| 805. | OCHF$_2$ | Cl | H | C(CH$_3$)$_3$ |
| 806. | OCHF$_2$ | F | H | C(CH$_3$)$_3$ |
| 807. | OCHF$_2$ | CH$_3$ | H | C(CH$_3$)$_3$ |
| 808. | OCHF$_2$ | C$_2$H$_5$ | H | C(CH$_3$)$_3$ |
| 809. | OCHF$_2$ | OCF$_3$ | H | C(CH$_3$)$_3$ |
| 810. | OCHF$_2$ | CF$_3$ | H | C(CH$_3$)$_3$ |
| 811. | OCHF$_2$ | Br | H | C$_6$H$_5$ |
| 812. | OCHF$_2$ | OCH$_3$ | H | C$_6$H$_5$ |
| 813. | OCHF$_2$ | Cl | H | C$_6$H$_5$ |
| 814. | OCHF$_2$ | F | H | C$_6$H$_5$ |
| 815. | OCHF$_2$ | CH$_3$ | H | C$_6$H$_5$ |
| 816. | OCHF$_2$ | C$_2$H$_5$ | H | C$_6$H$_5$ |
| 817. | OCHF$_2$ | OCF$_3$ | H | C$_6$H$_5$ |
| 818. | OCHF$_2$ | CF$_3$ | H | C$_6$H$_5$ |
| 819. | OCHF$_2$ | Br | H | cyclopropyl |
| 820. | OCHF$_2$ | OCH$_3$ | H | cyclopropyl |
| 821. | OCHF$_2$ | Cl | H | cyclopropyl |
| 822. | OCHF$_2$ | F | H | cyclopropyl |
| 823. | OCHF$_2$ | CH$_3$ | H | cyclopropyl |
| 824. | OCHF$_2$ | C$_2$H$_5$ | H | cyclopropyl |
| 825. | OCHF$_2$ | OCF$_3$ | H | cyclopropyl |
| 826. | OCHF$_2$ | CF$_3$ | H | cyclopropyl |
| 827. | OCHF$_2$ | Br | H | CH$_2$-cyclopropyl |
| 828. | OCHF$_2$ | OCH$_3$ | H | CH$_2$-cyclopropyl |
| 829. | OCHF$_2$ | Cl | H | CH$_2$-cyclopropyl |
| 830. | OCHF$_2$ | F | H | CH$_2$-cyclopropyl |
| 831. | OCHF$_2$ | CH$_3$ | H | CH$_2$-cyclopropyl |
| 832. | OCHF$_2$ | C$_2$H$_5$ | H | CH$_2$-cyclopropyl |
| 833. | OCHF$_2$ | OCF$_3$ | H | CH$_2$-cyclopropyl |
| 834. | OCHF$_2$ | CF$_3$ | H | CH$_2$-cyclopropyl |
| 835. | OCHF$_2$ | Br | H | cyclobutyl |
| 836. | OCHF$_2$ | OCH$_3$ | H | cyclobutyl |
| 837. | OCHF$_2$ | Cl | H | cyclobutyl |
| 838. | OCHF$_2$ | F | H | cyclobutyl |
| 839. | OCHF$_2$ | CH$_3$ | H | cyclobutyl |
| 840. | OCHF$_2$ | C$_2$H$_5$ | H | cyclobutyl |
| 841. | OCHF$_2$ | OCF$_3$ | H | cyclobutyl |

TABLE 1-continued (Ia)

| No. | $R^b$ | $R^c$ | $R^d$ | $R^2$ |
|---|---|---|---|---|
| 842. | OCHF$_2$ | CF$_3$ | H | cyclobutyl |
| 843. | OCHF$_2$ | Br | H | cyclopentyl |
| 844. | OCHF$_2$ | OCH$_3$ | H | cyclopentyl |
| 845. | OCHF$_2$ | Cl | H | cyclopentyl |
| 846. | OCHF$_2$ | F | H | cyclopentyl |
| 847. | OCHF$_2$ | CH$_3$ | H | cyclopentyl |
| 848. | OCHF$_2$ | C$_2$H$_5$ | H | cyclopentyl |
| 849. | OCHF$_2$ | OCF$_3$ | H | cyclopentyl |
| 850. | OCHF$_2$ | CF$_3$ | H | cyclopentyl |
| 851. | OCHF$_2$ | Br | H | cyclohexyl |
| 852. | OCHF$_2$ | OCH$_3$ | H | cyclohexyl |
| 853. | OCHF$_2$ | Cl | H | cyclohexyl |
| 854. | OCHF$_2$ | F | H | cyclohexyl |
| 855. | OCHF$_2$ | CH$_3$ | H | cyclohexyl |
| 856. | OCHF$_2$ | C$_2$H$_5$ | H | cyclohexyl |
| 857. | OCHF$_2$ | OCF$_3$ | H | cyclohexyl |
| 858. | OCHF$_2$ | CF$_3$ | H | cyclohexyl |
| 859. | OCHF$_2$ | H | Br | H |
| 860. | OCHF$_2$ | H | OCH$_3$ | H |
| 861. | OCHF$_2$ | H | Cl | H |
| 862. | OCHF$_2$ | H | F | H |
| 863. | OCHF$_2$ | H | CH$_3$ | H |
| 864. | OCHF$_2$ | H | C$_2$H$_5$ | H |
| 865. | OCHF$_2$ | H | OCF$_3$ | H |
| 866. | OCHF$_2$ | H | CF$_3$ | H |
| 867. | OCHF$_2$ | H | Br | CH$_3$ |
| 868. | OCHF$_2$ | H | OCH$_3$ | CH$_3$ |
| 869. | OCHF$_2$ | H | Cl | CH$_3$ |
| 870. | OCHF$_2$ | H | F | CH$_3$ |
| 871. | OCHF$_2$ | H | CH$_3$ | CH$_3$ |
| 872. | OCHF$_2$ | H | C$_2$H$_5$ | CH$_3$ |
| 873. | OCHF$_2$ | H | OCF$_3$ | CH$_3$ |
| 874. | OCHF$_2$ | H | CF$_3$ | CH$_3$ |
| 875. | OCHF$_2$ | H | Br | C$_2$H$_5$ |
| 876. | OCHF$_2$ | H | OCH$_3$ | C$_2$H$_5$ |
| 877. | OCHF$_2$ | H | Cl | C$_2$H$_5$ |
| 878. | OCHF$_2$ | H | F | C$_2$H$_5$ |
| 879. | OCHF$_2$ | H | CH$_3$ | C$_2$H$_5$ |
| 880. | OCHF$_2$ | H | C$_2$H$_5$ | C$_2$H$_5$ |
| 881. | OCHF$_2$ | H | OCF$_3$ | C$_2$H$_5$ |
| 882. | OCHF$_2$ | H | CF$_3$ | C$_2$H$_5$ |
| 883. | OCHF$_2$ | H | Br | n-C$_3$H$_7$ |
| 884. | OCHF$_2$ | H | OCH$_3$ | n-C$_3$H$_7$ |
| 885. | OCHF$_2$ | H | Cl | n-C$_3$H$_7$ |
| 886. | OCHF$_2$ | H | F | n-C$_3$H$_7$ |
| 887. | OCHF$_2$ | H | CH$_3$ | n-C$_3$H$_7$ |
| 888. | OCHF$_2$ | H | C$_2$H$_5$ | n-C$_3$H$_7$ |
| 889. | OCHF$_2$ | H | OCF$_3$ | n-C$_3$H$_7$ |
| 890. | OCHF$_2$ | H | CF$_3$ | n-C$_3$H$_7$ |
| 891. | OCHF$_2$ | H | Br | CH(CH$_3$)$_2$ |
| 892. | OCHF$_2$ | H | OCH$_3$ | CH(CH$_3$)$_2$ |
| 893. | OCHF$_2$ | H | Cl | CH(CH$_3$)$_2$ |
| 894. | OCHF$_2$ | H | F | CH(CH$_3$)$_2$ |
| 895. | OCHF$_2$ | H | CH$_3$ | CH(CH$_3$)$_2$ |
| 896. | OCHF$_2$ | H | C$_2$H$_5$ | CH(CH$_3$)$_2$ |
| 897. | OCHF$_2$ | H | OCF$_3$ | CH(CH$_3$)$_2$ |
| 898. | OCHF$_2$ | H | CF$_3$ | CH(CH$_3$)$_2$ |
| 899. | OCHF$_2$ | H | Br | n-C$_4$H$_9$ |
| 900. | OCHF$_2$ | H | OCH$_3$ | n-C$_4$H$_9$ |
| 901. | OCHF$_2$ | H | Cl | n-C$_4$H$_9$ |
| 902. | OCHF$_2$ | H | F | n-C$_4$H$_9$ |
| 903. | OCHF$_2$ | H | CH$_3$ | n-C$_4$H$_9$ |
| 904. | OCHF$_2$ | H | C$_2$H$_5$ | n-C$_4$H$_9$ |
| 905. | OCHF$_2$ | H | OCF$_3$ | n-C$_4$H$_9$ |
| 906. | OCHF$_2$ | H | CF$_3$ | n-C$_4$H$_9$ |
| 907. | OCHF$_2$ | H | Br | C(CH$_3$)$_3$ |
| 908. | OCHF$_2$ | H | OCH$_3$ | C(CH$_3$)$_3$ |
| 909. | OCHF$_2$ | H | Cl | C(CH$_3$)$_3$ |
| 910. | OCHF$_2$ | H | F | C(CH$_3$)$_3$ |
| 911. | OCHF$_2$ | H | CH$_3$ | C(CH$_3$)$_3$ |
| 912. | OCHF$_2$ | H | C$_2$H$_5$ | C(CH$_3$)$_3$ |
| 913. | OCHF$_2$ | H | OCF$_3$ | C(CH$_3$)$_3$ |
| 914. | OCHF$_2$ | H | CF$_3$ | C(CH$_3$)$_3$ |
| 915. | OCHF$_2$ | H | Br | C$_6$H$_5$ |
| 916. | OCHF$_2$ | H | OCH$_3$ | C$_6$H$_5$ |
| 917. | OCHF$_2$ | H | Cl | C$_6$H$_5$ |
| 918. | OCHF$_2$ | H | F | C$_6$H$_5$ |
| 919. | OCHF$_2$ | H | CH$_3$ | C$_6$H$_5$ |
| 920. | OCHF$_2$ | H | C$_2$H$_5$ | C$_6$H$_5$ |
| 921. | OCHF$_2$ | H | OCF$_3$ | C$_6$H$_5$ |
| 922. | OCHF$_2$ | H | CF$_3$ | C$_6$H$_5$ |
| 923. | OCHF$_2$ | H | Br | cyclopropyl |
| 924. | OCHF$_2$ | H | OCH$_3$ | cyclopropyl |
| 925. | OCHF$_2$ | H | Cl | cyclopropyl |
| 926. | OCHF$_2$ | H | F | cyclopropyl |
| 927. | OCHF$_2$ | H | CH$_3$ | cyclopropyl |
| 928. | OCHF$_2$ | H | C$_2$H$_5$ | cyclopropyl |
| 929. | OCHF$_2$ | H | OCF$_3$ | cyclopropyl |
| 930. | OCHF$_2$ | H | CF$_3$ | cyclopropyl |
| 931. | OCHF$_2$ | H | Br | CH$_2$-cyclopropyl |
| 932. | OCHF$_2$ | H | OCH$_3$ | CH$_2$-cyclopropyl |
| 933. | OCHF$_2$ | H | Cl | CH$_2$-cyclopropyl |
| 934. | OCHF$_2$ | H | F | CH$_2$-cyclopropyl |
| 935. | OCHF$_2$ | H | CH$_3$ | CH$_2$-cyclopropyl |
| 936. | OCHF$_2$ | H | C$_2$H$_5$ | CH$_2$-cyclopropyl |
| 937. | OCHF$_2$ | H | OCF$_3$ | CH$_2$-cyclopropyl |
| 938. | OCHF$_2$ | H | CF$_3$ | CH$_2$-cyclopropyl |
| 939. | OCHF$_2$ | H | Br | cyclobutyl |
| 940. | OCHF$_2$ | H | OCH$_3$ | cyclobutyl |
| 941. | OCHF$_2$ | H | Cl | cyclobutyl |
| 942. | OCHF$_2$ | H | F | cyclobutyl |
| 943. | OCHF$_2$ | H | CH$_3$ | cyclobutyl |
| 944. | OCHF$_2$ | H | C$_2$H$_5$ | cyclobutyl |
| 945. | OCHF$_2$ | H | OCF$_3$ | cyclobutyl |
| 946. | OCHF$_2$ | H | CF$_3$ | cyclobutyl |
| 947. | OCHF$_2$ | H | Br | cyclopentyl |
| 948. | OCHF$_2$ | H | OCH$_3$ | cyclopentyl |
| 949. | OCHF$_2$ | H | Cl | cyclopentyl |
| 950. | OCHF$_2$ | H | F | cyclopentyl |
| 951. | OCHF$_2$ | H | CH$_3$ | cyclopentyl |
| 952. | OCHF$_2$ | H | C$_2$H$_5$ | cyclopentyl |
| 953. | OCHF$_2$ | H | OCF$_3$ | cyclopentyl |
| 954. | OCHF$_2$ | H | CF$_3$ | cyclopentyl |
| 955. | OCHF$_2$ | H | Br | cyclohexyl |
| 956. | OCHF$_2$ | H | OCH$_3$ | cyclohexyl |
| 957. | OCHF$_2$ | H | Cl | cyclohexyl |
| 958. | OCHF$_2$ | H | F | cyclohexyl |
| 959. | OCHF$_2$ | H | CH$_3$ | cyclohexyl |
| 960. | OCHF$_2$ | H | C$_2$H$_5$ | cyclohexyl |
| 961. | OCHF$_2$ | H | OCF$_3$ | cyclohexyl |
| 962. | OCHF$_2$ | H | CF$_3$ | cyclohexyl |
| 963. | OCH$_3$ | Br | H | H |
| 964. | OCH$_3$ | OCH$_3$ | H | H |
| 965. | OCH$_3$ | Cl | H | H |
| 966. | OCH$_3$ | F | H | H |
| 967. | OCH$_3$ | CH$_3$ | H | H |
| 968. | OCH$_3$ | C$_2$H$_5$ | H | H |
| 969. | OCH$_3$ | CF$_3$ | H | H |
| 970. | OCH$_3$ | OCF$_3$ | H | H |
| 971. | OCH$_3$ | OCHF$_2$ | H | H |

TABLE 1-continued (Ia)

| No. | R$^b$ | R$^c$ | R$^d$ | R$^2$ |
|---|---|---|---|---|
| 972. | OCH$_3$ | Br | H | CH$_3$ |
| 973. | OCH$_3$ | OCH$_3$ | H | CH$_3$ |
| 974. | OCH$_3$ | Cl | H | CH$_3$ |
| 975. | OCH$_3$ | F | H | CH$_3$ |
| 976. | OCH$_3$ | CH$_3$ | H | CH$_3$ |
| 977. | OCH$_3$ | C$_2$H$_5$ | H | CH$_3$ |
| 978. | OCH$_3$ | CF$_3$ | H | CH$_3$ |
| 979. | OCH$_3$ | OCF$_3$ | H | CH$_3$ |
| 980. | OCH$_3$ | OCHF$_2$ | H | CH$_3$ |
| 981. | OCH$_3$ | Br | H | C$_2$H$_5$ |
| 982. | OCH$_3$ | OCH$_3$ | H | C$_2$H$_5$ |
| 983. | OCH$_3$ | Cl | H | C$_2$H$_5$ |
| 984. | OCH$_3$ | F | H | C$_2$H$_5$ |
| 985. | OCH$_3$ | CH$_3$ | H | C$_2$H$_5$ |
| 986. | OCH$_3$ | C$_2$H$_5$ | H | C$_2$H$_5$ |
| 987. | OCH$_3$ | CF$_3$ | H | C$_2$H$_5$ |
| 988. | OCH$_3$ | OCF$_3$ | H | C$_2$H$_5$ |
| 989. | OCH$_3$ | OCHF$_2$ | H | C$_2$H$_5$ |
| 990. | OCH$_3$ | Br | H | n-C$_3$H$_7$ |
| 991. | OCH$_3$ | OCH$_3$ | H | n-C$_3$H$_7$ |
| 992. | OCH$_3$ | Cl | H | n-C$_3$H$_7$ |
| 993. | OCH$_3$ | F | H | n-C$_3$H$_7$ |
| 994. | OCH$_3$ | CH$_3$ | H | n-C$_3$H$_7$ |
| 995. | OCH$_3$ | C$_2$H$_5$ | H | n-C$_3$H$_7$ |
| 996. | OCH$_3$ | CF$_3$ | H | n-C$_3$H$_7$ |
| 997. | OCH$_3$ | OCF$_3$ | H | n-C$_3$H$_7$ |
| 998. | OCH$_3$ | OCHF$_2$ | H | n-C$_3$H$_7$ |
| 999. | OCH$_3$ | Br | H | CH(CH$_3$)$_2$ |
| 1000. | OCH$_3$ | OCH$_3$ | H | CH(CH$_3$)$_2$ |
| 1001. | OCH$_3$ | Cl | H | CH(CH$_3$)$_2$ |
| 1002. | OCH$_3$ | F | H | CH(CH$_3$)$_2$ |
| 1003. | OCH$_3$ | CH$_3$ | H | CH(CH$_3$)$_2$ |
| 1004. | OCH$_3$ | C$_2$H$_5$ | H | CH(CH$_3$)$_2$ |
| 1005. | OCH$_3$ | CF$_3$ | H | CH(CH$_3$)$_2$ |
| 1006. | OCH$_3$ | OCF$_3$ | H | CH(CH$_3$)$_2$ |
| 1007. | OCH$_3$ | OCHF$_2$ | H | CH(CH$_3$)$_2$ |
| 1008. | OCH$_3$ | Br | H | n-C$_4$H$_9$ |
| 1009. | OCH$_3$ | OCH$_3$ | H | n-C$_4$H$_9$ |
| 1010. | OCH$_3$ | Cl | H | n-C$_4$H$_9$ |
| 1011. | OCH$_3$ | F | H | n-C$_4$H$_9$ |
| 1012. | OCH$_3$ | CH$_3$ | H | n-C$_4$H$_9$ |
| 1013. | OCH$_3$ | C$_2$H$_5$ | H | n-C$_4$H$_9$ |
| 1014. | OCH$_3$ | CF$_3$ | H | n-C$_4$H$_9$ |
| 1015. | OCH$_3$ | OCF$_3$ | H | n-C$_4$H$_9$ |
| 1016. | OCH$_3$ | OCHF$_2$ | H | n-C$_4$H$_9$ |
| 1017. | OCH$_3$ | Br | H | C(CH$_3$)$_3$ |
| 1018. | OCH$_3$ | OCH$_3$ | H | C(CH$_3$)$_3$ |
| 1019. | OCH$_3$ | Cl | H | C(CH$_3$)$_3$ |
| 1020. | OCH$_3$ | F | H | C(CH$_3$)$_3$ |
| 1021. | OCH$_3$ | CH$_3$ | H | C(CH$_3$)$_3$ |
| 1022. | OCH$_3$ | C$_2$H$_5$ | H | C(CH$_3$)$_3$ |
| 1023. | OCH$_3$ | CF$_3$ | H | C(CH$_3$)$_3$ |
| 1024. | OCH$_3$ | OCF$_3$ | H | C(CH$_3$)$_3$ |
| 1025. | OCH$_3$ | OCHF$_2$ | H | C(CH$_3$)$_3$ |
| 1026. | OCH$_3$ | Br | H | C$_6$H$_5$ |
| 1027. | OCH$_3$ | OCH$_3$ | H | C$_6$H$_5$ |
| 1028. | OCH$_3$ | Cl | H | C$_6$H$_5$ |
| 1029. | OCH$_3$ | F | H | C$_6$H$_5$ |
| 1030. | OCH$_3$ | CH$_3$ | H | C$_6$H$_5$ |
| 1031. | OCH$_3$ | C$_2$H$_5$ | H | C$_6$H$_5$ |
| 1032. | OCH$_3$ | CF$_3$ | H | C$_6$H$_5$ |
| 1033. | OCH$_3$ | OCF$_3$ | H | C$_6$H$_5$ |
| 1034. | OCH$_3$ | OCHF$_2$ | H | C$_6$H$_5$ |
| 1035. | OCH$_3$ | Br | H | cyclopropyl |
| 1036. | OCH$_3$ | OCH$_3$ | H | cyclopropyl |

TABLE 1-continued (Ia)

| No. | R$^b$ | R$^c$ | R$^d$ | R$^2$ |
|---|---|---|---|---|
| 1037. | OCH$_3$ | Cl | H | cyclopropyl |
| 1038. | OCH$_3$ | F | H | cyclopropyl |
| 1039. | OCH$_3$ | CH$_3$ | H | cyclopropyl |
| 1040. | OCH$_3$ | C$_2$H$_5$ | H | cyclopropyl |
| 1041. | OCH$_3$ | CF$_3$ | H | cyclopropyl |
| 1042. | OCH$_3$ | OCF$_3$ | H | cyclopropyl |
| 1043. | OCH$_3$ | OCHF$_2$ | H | cyclopropyl |
| 1044. | OCH$_3$ | Br | H | CH$_2$-cyclopropyl |
| 1045. | OCH$_3$ | OCH$_3$ | H | CH$_2$-cyclopropyl |
| 1046. | OCH$_3$ | Cl | H | CH$_2$-cyclopropyl |
| 1047. | OCH$_3$ | F | H | CH$_2$-cyclopropyl |
| 1048. | OCH$_3$ | CH$_3$ | H | CH$_2$-cyclopropyl |
| 1049. | OCH$_3$ | C$_2$H$_5$ | H | CH$_2$-cyclopropyl |
| 1050. | OCH$_3$ | CF$_3$ | H | CH$_2$-cyclopropyl |
| 1051. | OCH$_3$ | OCF$_3$ | H | CH$_2$-cyclopropyl |
| 1052. | OCH$_3$ | OCHF$_2$ | H | CH$_2$-cyclopropyl |
| 1053. | OCH$_3$ | Br | H | cyclobutyl |
| 1054. | OCH$_3$ | OCH$_3$ | H | cyclobutyl |
| 1055. | OCH$_3$ | Cl | H | cyclobutyl |
| 1056. | OCH$_3$ | F | H | cyclobutyl |
| 1057. | OCH$_3$ | CH$_3$ | H | cyclobutyl |
| 1058. | OCH$_3$ | C$_2$H$_5$ | H | cyclobutyl |
| 1059. | OCH$_3$ | CF$_3$ | H | cyclobutyl |
| 1060. | OCH$_3$ | OCF$_3$ | H | cyclobutyl |
| 1061. | OCH$_3$ | OCHF$_2$ | H | cyclobutyl |
| 1062. | OCH$_3$ | Br | H | cyclopentyl |
| 1063. | OCH$_3$ | OCH$_3$ | H | cyclopentyl |
| 1064. | OCH$_3$ | Cl | H | cyclopentyl |
| 1065. | OCH$_3$ | F | H | cyclopentyl |
| 1066. | OCH$_3$ | CH$_3$ | H | cyclopentyl |
| 1067. | OCH$_3$ | C$_2$H$_5$ | H | cyclopentyl |
| 1068. | OCH$_3$ | CF$_3$ | H | cyclopentyl |
| 1069. | OCH$_3$ | OCF$_3$ | H | cyclopentyl |
| 1070. | OCH$_3$ | OCHF$_2$ | H | cyclopentyl |
| 1071. | OCH$_3$ | Br | H | cyclohexyl |
| 1072. | OCH$_3$ | OCH$_3$ | H | cyclohexyl |
| 1073. | OCH$_3$ | Cl | H | cyclohexyl |
| 1074. | OCH$_3$ | F | H | cyclohexyl |
| 1075. | OCH$_3$ | CH$_3$ | H | cyclohexyl |
| 1076. | OCH$_3$ | C$_2$H$_5$ | H | cyclohexyl |
| 1077. | OCH$_3$ | CF$_3$ | H | cyclohexyl |
| 1078. | OCH$_3$ | OCF$_3$ | H | cyclohexyl |
| 1079. | OCH$_3$ | OCHF$_2$ | H | cyclohexyl |
| 1080. | OCH$_3$ | H | Br | H |
| 1081. | OCH$_3$ | H | OCH$_3$ | H |
| 1082. | OCH$_3$ | H | Cl | H |
| 1083. | OCH$_3$ | H | F | H |
| 1084. | OCH$_3$ | H | CH$_3$ | H |
| 1085. | OCH$_3$ | H | C$_2$H$_5$ | H |
| 1086. | OCH$_3$ | H | CF$_3$ | H |
| 1087. | OCH$_3$ | H | OCF$_3$ | H |
| 1088. | OCH$_3$ | H | OCHF$_2$ | H |
| 1089. | OCH$_3$ | H | Br | CH$_3$ |
| 1090. | OCH$_3$ | H | OCH$_3$ | CH$_3$ |
| 1091. | OCH$_3$ | H | Cl | CH$_3$ |
| 1092. | OCH$_3$ | H | F | CH$_3$ |
| 1093. | OCH$_3$ | H | CH$_3$ | CH$_3$ |
| 1094. | OCH$_3$ | H | C$_2$H$_5$ | CH$_3$ |
| 1095. | OCH$_3$ | H | CF$_3$ | CH$_3$ |
| 1096. | OCH$_3$ | H | OCF$_3$ | CH$_3$ |
| 1097. | OCH$_3$ | H | OCHF$_2$ | CH$_3$ |
| 1098. | OCH$_3$ | H | Br | C$_2$H$_5$ |
| 1099. | OCH$_3$ | H | OCH$_3$ | C$_2$H$_5$ |
| 1100. | OCH$_3$ | H | Cl | C$_2$H$_5$ |
| 1101. | OCH$_3$ | H | F | C$_2$H$_5$ |

TABLE 1-continued (Ia)

| No. | $R^b$ | $R^c$ | $R^d$ | $R^2$ |
|---|---|---|---|---|
| 1102. | OCH$_3$ | H | CH$_3$ | C$_2$H$_5$ |
| 1103. | OCH$_3$ | H | C$_2$H$_5$ | C$_2$H$_5$ |
| 1104. | OCH$_3$ | H | CF$_3$ | C$_2$H$_5$ |
| 1105. | OCH$_3$ | H | OCF$_3$ | C$_2$H$_5$ |
| 1106. | OCH$_3$ | H | OCHF$_2$ | C$_2$H$_5$ |
| 1107. | OCH$_3$ | H | Br | n-C$_3$H$_7$ |
| 1108. | OCH$_3$ | H | OCH$_3$ | n-C$_3$H$_7$ |
| 1109. | OCH$_3$ | H | Cl | n-C$_3$H$_7$ |
| 1110. | OCH$_3$ | H | F | n-C$_3$H$_7$ |
| 1111. | OCH$_3$ | H | CH$_3$ | n-C$_3$H$_7$ |
| 1112. | OCH$_3$ | H | C$_2$H$_5$ | n-C$_3$H$_7$ |
| 1113. | OCH$_3$ | H | CF$_3$ | n-C$_3$H$_7$ |
| 1114. | OCH$_3$ | H | OCF$_3$ | n-C$_3$H$_7$ |
| 1115. | OCH$_3$ | H | OCHF$_2$ | n-C$_3$H$_7$ |
| 1116. | OCH$_3$ | H | Br | CH(CH$_3$)$_2$ |
| 1117. | OCH$_3$ | H | OCH$_3$ | CH(CH$_3$)$_2$ |
| 1118. | OCH$_3$ | H | Cl | CH(CH$_3$)$_2$ |
| 1119. | OCH$_3$ | H | F | CH(CH$_3$)$_2$ |
| 1120. | OCH$_3$ | H | CH$_3$ | CH(CH$_3$)$_2$ |
| 1121. | OCH$_3$ | H | C$_2$H$_5$ | CH(CH$_3$)$_2$ |
| 1122. | OCH$_3$ | H | CF$_3$ | CH(CH$_3$)$_2$ |
| 1123. | OCH$_3$ | H | OCF$_3$ | CH(CH$_3$)$_2$ |
| 1124. | OCH$_3$ | H | OCHF$_2$ | CH(CH$_3$)$_2$ |
| 1125. | OCH$_3$ | H | Br | n-C$_4$H$_9$ |
| 1126. | OCH$_3$ | H | OCH$_3$ | n-C$_4$H$_9$ |
| 1127. | OCH$_3$ | H | Cl | n-C$_4$H$_9$ |
| 1128. | OCH$_3$ | H | F | n-C$_4$H$_9$ |
| 1129. | OCH$_3$ | H | CH$_3$ | n-C$_4$H$_9$ |
| 1130. | OCH$_3$ | H | C$_2$H$_5$ | n-C$_4$H$_9$ |
| 1131. | OCH$_3$ | H | CF$_3$ | n-C$_4$H$_9$ |
| 1132. | OCH$_3$ | H | OCF$_3$ | n-C$_4$H$_9$ |
| 1133. | OCH$_3$ | H | OCHF$_2$ | n-C$_4$H$_9$ |
| 1134. | OCH$_3$ | H | Br | C(CH$_3$)$_3$ |
| 1135. | OCH$_3$ | H | OCH$_3$ | C(CH$_3$)$_3$ |
| 1136. | OCH$_3$ | H | Cl | C(CH$_3$)$_3$ |
| 1137. | OCH$_3$ | H | F | C(CH$_3$)$_3$ |
| 1138. | OCH$_3$ | H | CH$_3$ | C(CH$_3$)$_3$ |
| 1139. | OCH$_3$ | H | C$_2$H$_5$ | C(CH$_3$)$_3$ |
| 1140. | OCH$_3$ | H | CF$_3$ | C(CH$_3$)$_3$ |
| 1141. | OCH$_3$ | H | OCF$_3$ | C(CH$_3$)$_3$ |
| 1142. | OCH$_3$ | H | OCHF$_2$ | C(CH$_3$)$_3$ |
| 1143. | OCH$_3$ | H | Br | C$_6$H$_5$ |
| 1144. | OCH$_3$ | H | OCH$_3$ | C$_6$H$_5$ |
| 1145. | OCH$_3$ | H | Cl | C$_6$H$_5$ |
| 1146. | OCH$_3$ | H | F | C$_6$H$_5$ |
| 1147. | OCH$_3$ | H | CH$_3$ | C$_6$H$_5$ |
| 1148. | OCH$_3$ | H | C$_2$H$_5$ | C$_6$H$_5$ |
| 1149. | OCH$_3$ | H | CF$_3$ | C$_6$H$_5$ |
| 1150. | OCH$_3$ | H | OCF$_3$ | C$_6$H$_5$ |
| 1151. | OCH$_3$ | H | OCHF$_2$ | C$_6$H$_5$ |
| 1152. | OCH$_3$ | H | Br | cyclopropyl |
| 1153. | OCH$_3$ | H | OCH$_3$ | cyclopropyl |
| 1154. | OCH$_3$ | H | Cl | cyclopropyl |
| 1155. | OCH$_3$ | H | F | cyclopropyl |
| 1156. | OCH$_3$ | H | CH$_3$ | cyclopropyl |
| 1157. | OCH$_3$ | H | C$_2$H$_5$ | cyclopropyl |
| 1158. | OCH$_3$ | H | CF$_3$ | cyclopropyl |
| 1159. | OCH$_3$ | H | OCF$_3$ | cyclopropyl |
| 1160. | OCH$_3$ | H | OCHF$_2$ | cyclopropyl |
| 1161. | OCH$_3$ | H | Br | CH$_2$-cyclopropyl |
| 1162. | OCH$_3$ | H | OCH$_3$ | CH$_2$-cyclopropyl |
| 1163. | OCH$_3$ | H | Cl | CH$_2$-cyclopropyl |
| 1164. | OCH$_3$ | H | F | CH$_2$-cyclopropyl |
| 1165. | OCH$_3$ | H | CH$_3$ | CH$_2$-cyclopropyl |
| 1166. | OCH$_3$ | H | C$_2$H$_5$ | CH$_2$-cyclopropyl |
| 1167. | OCH$_3$ | H | CF$_3$ | CH$_2$-cyclopropyl |
| 1168. | OCH$_3$ | H | OCF$_3$ | CH$_2$-cyclopropyl |
| 1169. | OCH$_3$ | H | OCHF$_2$ | CH$_2$-cyclopropyl |
| 1170. | OCH$_3$ | H | Br | cyclobutyl |
| 1171. | OCH$_3$ | H | OCH$_3$ | cyclobutyl |
| 1172. | OCH$_3$ | H | Cl | cyclobutyl |
| 1173. | OCH$_3$ | H | F | cyclobutyl |
| 1174. | OCH$_3$ | H | CH$_3$ | cyclobutyl |
| 1175. | OCH$_3$ | H | C$_2$H$_5$ | cyclobutyl |
| 1176. | OCH$_3$ | H | CF$_3$ | cyclobutyl |
| 1177. | OCH$_3$ | H | OCF$_3$ | cyclobutyl |
| 1178. | OCH$_3$ | H | OCHF$_2$ | cyclobutyl |
| 1179. | OCH$_3$ | H | Br | cyclopentyl |
| 1180. | OCH$_3$ | H | OCH$_3$ | cyclopentyl |
| 1181. | OCH$_3$ | H | Cl | cyclopentyl |
| 1182. | OCH$_3$ | H | F | cyclopentyl |
| 1183. | OCH$_3$ | H | CH$_3$ | cyclopentyl |
| 1184. | OCH$_3$ | H | C$_2$H$_5$ | cyclopentyl |
| 1185. | OCH$_3$ | H | CF$_3$ | cyclopentyl |
| 1186. | OCH$_3$ | H | OCF$_3$ | cyclopentyl |
| 1187. | OCH$_3$ | H | OCHF$_2$ | cyclopentyl |
| 1188. | OCH$_3$ | H | Br | cyclohexyl |
| 1189. | OCH$_3$ | H | OCH$_3$ | cyclohexyl |
| 1190. | OCH$_3$ | H | Cl | cyclohexyl |
| 1191. | OCH$_3$ | H | F | cyclohexyl |
| 1192. | OCH$_3$ | H | CH$_3$ | cyclohexyl |
| 1193. | OCH$_3$ | H | C$_2$H$_5$ | cyclohexyl |
| 1194. | OCH$_3$ | H | CF$_3$ | cyclohexyl |
| 1195. | OCH$_3$ | H | OCF$_3$ | cyclohexyl |
| 1196. | OCH$_3$ | H | OCHF$_2$ | cyclohexyl |
| 1197. | Cl | Cl | H | H |
| 1198. | Cl | F | H | H |
| 1199. | Cl | CH$_3$ | H | H |
| 1200. | Cl | OCH$_3$ | H | H |
| 1201. | Cl | Br | H | H |
| 1202. | Cl | CF$_3$ | H | H |
| 1203. | Cl | OCF$_3$ | H | H |
| 1204. | Cl | Cl | H | CH$_3$ |
| 1205. | Cl | F | H | CH$_3$ |
| 1206. | Cl | CH$_3$ | H | CH$_3$ |
| 1207. | Cl | OCH$_3$ | H | CH$_3$ |
| 1208. | Cl | Br | H | CH$_3$ |
| 1209. | Cl | CF$_3$ | H | CH$_3$ |
| 1210. | Cl | OCF$_3$ | H | CH$_3$ |
| 1211. | Cl | Cl | H | C$_2$H$_5$ |
| 1212. | Cl | F | H | C$_2$H$_5$ |
| 1213. | Cl | CH$_3$ | H | C$_2$H$_5$ |
| 1214. | Cl | OCH$_3$ | H | C$_2$H$_5$ |
| 1215. | Cl | Br | H | C$_2$H$_5$ |
| 1216. | Cl | CF$_3$ | H | C$_2$H$_5$ |
| 1217. | Cl | OCF$_3$ | H | C$_2$H$_5$ |
| 1218. | Cl | Cl | H | n-C$_3$H$_7$ |
| 1219. | Cl | F | H | n-C$_3$H$_7$ |
| 1220. | Cl | CH$_3$ | H | n-C$_3$H$_7$ |
| 1221. | Cl | OCH$_3$ | H | n-C$_3$H$_7$ |
| 1222. | Cl | Br | H | n-C$_3$H$_7$ |
| 1223. | Cl | CF$_3$ | H | n-C$_3$H$_7$ |
| 1224. | Cl | OCF$_3$ | H | n-C$_3$H$_7$ |
| 1225. | Cl | Cl | H | CH(CH$_3$)$_2$ |
| 1226. | Cl | F | H | CH(CH$_3$)$_2$ |
| 1227. | Cl | CH$_3$ | H | CH(CH$_3$)$_2$ |
| 1228. | Cl | OCH$_3$ | H | CH(CH$_3$)$_2$ |
| 1229. | Cl | Br | H | CH(CH$_3$)$_2$ |
| 1230. | Cl | CF$_3$ | H | CH(CH$_3$)$_2$ |
| 1231. | Cl | OCF$_3$ | H | CH(CH$_3$)$_2$ |

TABLE 1-continued (Ia)

| No. | $R^b$ | $R^c$ | $R^d$ | $R^2$ |
|---|---|---|---|---|
| 1232. | Cl | Cl | H | n-C$_4$H$_9$ |
| 1233. | Cl | F | H | n-C$_4$H$_9$ |
| 1234. | Cl | CH$_3$ | H | n-C$_4$H$_9$ |
| 1235. | Cl | OCH$_3$ | H | n-C$_4$H$_9$ |
| 1236. | Cl | Br | H | n-C$_4$H$_9$ |
| 1237. | Cl | CF$_3$ | H | n-C$_4$H$_9$ |
| 1238. | Cl | OCF$_3$ | H | n-C$_4$H$_9$ |
| 1239. | Cl | Cl | H | C(CH$_3$)$_3$ |
| 1240. | Cl | F | H | C(CH$_3$)$_3$ |
| 1241. | Cl | CH$_3$ | H | C(CH$_3$)$_3$ |
| 1242. | Cl | OCH$_3$ | H | C(CH$_3$)$_3$ |
| 1243. | Cl | Br | H | C(CH$_3$)$_3$ |
| 1244. | Cl | CF$_3$ | H | C(CH$_3$)$_3$ |
| 1245. | Cl | OCF$_3$ | H | C(CH$_3$)$_3$ |
| 1246. | Cl | Cl | H | C$_6$H$_5$ |
| 1247. | Cl | F | H | C$_6$H$_5$ |
| 1248. | Cl | CH$_3$ | H | C$_6$H$_5$ |
| 1249. | Cl | OCH$_3$ | H | C$_6$H$_5$ |
| 1250. | Cl | Br | H | C$_6$H$_5$ |
| 1251. | Cl | CF$_3$ | H | C$_6$H$_5$ |
| 1252. | Cl | OCF$_3$ | H | C$_6$H$_5$ |
| 1253. | Cl | Cl | H | cyclopropyl |
| 1254. | Cl | F | H | cyclopropyl |
| 1255. | Cl | CH$_3$ | H | cyclopropyl |
| 1256. | Cl | OCH$_3$ | H | cyclopropyl |
| 1257. | Cl | Br | H | cyclopropyl |
| 1258. | Cl | CF$_3$ | H | cyclopropyl |
| 1259. | Cl | OCF$_3$ | H | cyclopropyl |
| 1260. | Cl | Cl | H | CH$_2$-cyclopropyl |
| 1261. | Cl | F | H | CH$_2$-cyclopropyl |
| 1262. | Cl | CH$_3$ | H | CH$_2$-cyclopropyl |
| 1263. | Cl | OCH$_3$ | H | CH$_2$-cyclopropyl |
| 1264. | Cl | Br | H | CH$_2$-cyclopropyl |
| 1265. | Cl | CF$_3$ | H | CH$_2$-cyclopropyl |
| 1266. | Cl | OCF$_3$ | H | CH$_2$-cyclopropyl |
| 1267. | Cl | Cl | H | cyclobutyl |
| 1268. | Cl | F | H | cyclobutyl |
| 1269. | Cl | CH$_3$ | H | cyclobutyl |
| 1270. | Cl | OCH$_3$ | H | cyclobutyl |
| 1271. | Cl | Br | H | cyclobutyl |
| 1272. | Cl | CF$_3$ | H | cyclobutyl |
| 1273. | Cl | OCF$_3$ | H | cyclobutyl |
| 1274. | Cl | Cl | H | cyclopentyl |
| 1275. | Cl | F | H | cyclopentyl |
| 1276. | Cl | CH$_3$ | H | cyclopentyl |
| 1277. | Cl | OCH$_3$ | H | cyclopentyl |
| 1278. | Cl | Br | H | cyclopentyl |
| 1279. | Cl | CF$_3$ | H | cyclopentyl |
| 1280. | Cl | OCF$_3$ | H | cyclopentyl |
| 1281. | Cl | Cl | H | cyclohexyl |
| 1282. | Cl | F | H | cyclohexyl |
| 1283. | Cl | CH$_3$ | H | cyclohexyl |
| 1284. | Cl | OCH$_3$ | H | cyclohexyl |
| 1285. | Cl | Br | H | cyclohexyl |
| 1286. | Cl | CF$_3$ | H | cyclohexyl |
| 1287. | Cl | OCF$_3$ | H | cyclohexyl |
| 1288. | Cl | H | Cl | H |
| 1289. | Cl | H | F | H |
| 1290. | Cl | H | CH$_3$ | H |
| 1291. | Cl | H | OCH$_3$ | H |
| 1292. | Cl | H | Br | H |
| 1293. | Cl | H | CF$_3$ | H |
| 1294. | Cl | H | OCF$_3$ | H |
| 1295. | Cl | H | Cl | CH$_3$ |
| 1296. | Cl | H | F | CH$_3$ |
| 1297. | Cl | H | CH$_3$ | CH$_3$ |
| 1298. | Cl | H | OCH$_3$ | CH$_3$ |
| 1299. | Cl | H | Br | CH$_3$ |
| 1300. | Cl | H | CF$_3$ | CH$_3$ |
| 1301. | Cl | H | OCF$_3$ | CH$_3$ |
| 1302. | Cl | H | Cl | C$_2$H$_5$ |
| 1303. | Cl | H | F | C$_2$H$_5$ |
| 1304. | Cl | H | CH$_3$ | C$_2$H$_5$ |
| 1305. | Cl | H | OCH$_3$ | C$_2$H$_5$ |
| 1306. | Cl | H | Br | C$_2$H$_5$ |
| 1307. | Cl | H | CF$_3$ | C$_2$H$_5$ |
| 1308. | Cl | H | OCF$_3$ | C$_2$H$_5$ |
| 1309. | Cl | H | Cl | n-C$_3$H$_7$ |
| 1310. | Cl | H | F | n-C$_3$H$_7$ |
| 1311. | Cl | H | CH$_3$ | n-C$_3$H$_7$ |
| 1312. | Cl | H | OCH$_3$ | n-C$_3$H$_7$ |
| 1313. | Cl | H | Br | n-C$_3$H$_7$ |
| 1314. | Cl | H | CF$_3$ | n-C$_3$H$_7$ |
| 1315. | Cl | H | OCF$_3$ | n-C$_3$H$_7$ |
| 1316. | Cl | H | Cl | CH(CH$_3$)$_2$ |
| 1317. | Cl | H | F | CH(CH$_3$)$_2$ |
| 1318. | Cl | H | CH$_3$ | CH(CH$_3$)$_2$ |
| 1319. | Cl | H | OCH$_3$ | CH(CH$_3$)$_2$ |
| 1320. | Cl | H | Br | CH(CH$_3$)$_2$ |
| 1321. | Cl | H | CF$_3$ | CH(CH$_3$)$_2$ |
| 1322. | Cl | H | OCF$_3$ | CH(CH$_3$)$_2$ |
| 1323. | Cl | H | Cl | n-C$_4$H$_9$ |
| 1324. | Cl | H | F | n-C$_4$H$_9$ |
| 1325. | Cl | H | CH$_3$ | n-C$_4$H$_9$ |
| 1326. | Cl | H | OCH$_3$ | n-C$_4$H$_9$ |
| 1327. | Cl | H | Br | n-C$_4$H$_9$ |
| 1328. | Cl | H | CF$_3$ | n-C$_4$H$_9$ |
| 1329. | Cl | H | OCF$_3$ | n-C$_4$H$_9$ |
| 1330. | Cl | H | Cl | C(CH$_3$)$_3$ |
| 1331. | Cl | H | F | C(CH$_3$)$_3$ |
| 1332. | Cl | H | CH$_3$ | C(CH$_3$)$_3$ |
| 1333. | Cl | H | OCH$_3$ | C(CH$_3$)$_3$ |
| 1334. | Cl | H | Br | C(CH$_3$)$_3$ |
| 1335. | Cl | H | CF$_3$ | C(CH$_3$)$_3$ |
| 1336. | Cl | H | OCF$_3$ | C(CH$_3$)$_3$ |
| 1337. | Cl. | H | Cl | C$_6$H$_5$ |
| 1338. | Cl | H | F | C$_6$H$_5$ |
| 1339. | Cl | H | CH$_3$ | C$_6$H$_5$ |
| 1340. | Cl | H | OCH$_3$ | C$_6$H$_5$ |
| 1341. | Cl | H | Br | C$_6$H$_5$ |
| 1342. | Cl | H | CF$_3$ | C$_6$H$_5$ |
| 1343. | Cl | H | OCF$_3$ | C$_6$H$_5$ |
| 1344. | Cl | H | Cl | cyclopropyl |
| 1345. | Cl | H | F | cyclopropyl |
| 1346. | Cl | H | CH$_3$ | cyclopropyl |
| 1347. | Cl | H | OCH$_3$ | cyclopropyl |
| 1348. | Cl | H | Br | cyclopropyl |
| 1349. | Cl | H | CF$_3$ | cyclopropyl |
| 1350. | Cl | H | OCF$_3$ | cyclopropyl |
| 1351. | Cl | H | Cl | CH$_2$-cyclopropyl |
| 1352. | Cl | H | F | CH$_2$-cyclopropyl |
| 1353. | Cl | H | CH$_3$ | CH$_2$-cyclopropyl |
| 1354. | Cl | H | OCH$_3$ | CH$_2$-cyclopropyl |
| 1355. | Cl | H | Br | CH$_2$-cyclopropyl |
| 1356. | Cl | H | CF$_3$ | CH$_2$-cyclopropyl |
| 1357. | Cl | H | OCF$_3$ | CH$_2$-cyclopropyl |
| 1358. | Cl | H | Cl | cyclobutyl |
| 1359. | Cl | H | F | cyclobutyl |
| 1360. | Cl | H | CH$_3$ | cyclobutyl |
| 1361. | Cl | H | OCH$_3$ | cyclobutyl |

TABLE 1-continued (Ia)

| No. | $R^b$ | $R^c$ | $R^d$ | $R^2$ |
|---|---|---|---|---|
| 1362. | Cl | H | Br | cyclobutyl |
| 1363. | Cl | H | $CF_3$ | cyclobutyl |
| 1364. | Cl | H | $OCF_3$ | cyclobutyl |
| 1365. | Cl | H | Cl | cyclopentyl |
| 1366. | Cl | H | F | cyclopentyl |
| 1367. | Cl | H | $CH_3$ | cyclopentyl |
| 1368. | Cl | H | $OCH_3$ | cyclopentyl |
| 1369. | Cl | H | Br | cyclopentyl |
| 1370. | Cl | H | $CF_3$ | cyclopentyl |
| 1371. | Cl | H | $OCF_3$ | cyclopentyl |
| 1372. | Cl | H | Cl | cyclohexyl |
| 1373. | Cl | H | F | cyclohexyl |
| 1374. | Cl | H | $CH_3$ | cyclohexyl |
| 1375. | Cl | H | $OCH_3$ | cyclohexyl |
| 1376. | Cl | H | Br | cyclohexyl |
| 1377. | Cl | H | $CF_3$ | cyclohexyl |
| 1378. | Cl | H | $OCF_3$ | cyclohexyl |
| 1379. | Br | Cl | H | H |
| 1380. | Br | F | H | H |
| 1381. | Br | $CH_3$ | H | H |
| 1382. | Br | $OCH_3$ | H | H |
| 1383. | Br | Br | H | H |
| 1384. | Br | $CF_3$ | H | H |
| 1385. | Br | $OCF_3$ | H | H |
| 1386. | Br | Cl | H | $CH_3$ |
| 1387. | Br | F | H | $CH_3$ |
| 1388. | Br | $CH_3$ | H | $CH_3$ |
| 1389. | Br | $OCH_3$ | H | $CH_3$ |
| 1390. | Br | Br | H | $CH_3$ |
| 1391. | Br | $CF_3$ | H | $CH_3$ |
| 1392. | Br | $OCF_3$ | H | $CH_3$ |
| 1393. | Br | Cl | H | $C_2H_5$ |
| 1394. | Br | F | H | $C_2H_5$ |
| 1395. | Br | $CH_3$ | H | $C_2H_5$ |
| 1396. | Br | $OCH_3$ | H | $C_2H_5$ |
| 1397. | Br | Br | H | $C_2H_5$ |
| 1398. | Br | $CF_3$ | H | $C_2H_5$ |
| 1399. | Br | $OCF_3$ | H | $C_2H_5$ |
| 1400. | Br | Cl | H | $n-C_3H_7$ |
| 1401. | Br | F | H | $n-C_3H_7$ |
| 1402. | Br | $CH_3$ | H | $n-C_3H_7$ |
| 1403. | Br | $OCH_3$ | H | $n-C_3H_7$ |
| 1404. | Br | Br | H | $n-C_3H_7$ |
| 1405. | Br | $CF_3$ | H | $n-C_3H_7$ |
| 1406. | Br | $OCF_3$ | H | $n-C_3H_7$ |
| 1407. | Br | Cl | H | $CH(CH_3)_2$ |
| 1408. | Br | F | H | $CH(CH_3)_2$ |
| 1409. | Br | $CH_3$ | H | $CH(CH_3)_2$ |
| 1410. | Br | $OCH_3$ | H | $CH(CH_3)_2$ |
| 1411. | Br | Br | H | $CH(CH_3)_2$ |
| 1412. | Br | $CF_3$ | H | $CH(CH_3)_2$ |
| 1413. | Br | $OCF_3$ | H | $CH(CH_3)_2$ |
| 1414. | Br | Cl | H | $n-C_4H_9$ |
| 1415. | Br | F | H | $n-C_4H_9$ |
| 1416. | Br | $CH_3$ | H | $n-C_4H_9$ |
| 1417. | Br | $OCH_3$ | H | $n-C_4H_9$ |
| 1418. | Br | Br | H | $n-C_4H_9$ |
| 1419. | Br | $CF_3$ | H | $n-C_4H_9$ |
| 1420. | Br | $OCF_3$ | H | $n-C_4H_9$ |
| 1421. | Br | Cl | H | $C(CH_3)_3$ |
| 1422. | Br | F | H | $C(CH_3)_3$ |
| 1423. | Br | $CH_3$ | H | $C(CH_3)_3$ |
| 1424. | Br | $OCH_3$ | H | $C(CH_3)_3$ |
| 1425. | Br | Br | H | $C(CH_3)_3$ |
| 1426. | Br | $CF_3$ | H | $C(CH_3)_3$ |
| 1427. | Br | $OCF_3$ | H | $C(CH_3)_3$ |
| 1428. | Br | Cl | H | $C_6H_5$ |
| 1429. | Br | F | H | $C_6H_5$ |
| 1430. | Br | $CH_3$ | H | $C_6H_5$ |
| 1431. | Br | $OCH_3$ | H | $C_6H_5$ |
| 1432. | Br | Br | H | $C_6H_5$ |
| 1433. | Br | $CF_3$ | H | $C_6H_5$ |
| 1434. | Br | $OCF_3$ | H | $C_6H_5$ |
| 1435. | Br | Cl | H | cyclopropyl |
| 1436. | Br | F | H | cyclopropyl |
| 1437. | Br | $CH_3$ | H | cyclopropyl |
| 1438. | Br | $OCH_3$ | H | cyclopropyl |
| 1439. | Br | Br | H | cyclopropyl |
| 1440. | Br | $CF_3$ | H | cyclopropyl |
| 1441. | Br | $OCF_3$ | H | cyclopropyl |
| 1442. | Br | Cl | H | $CH_2$-cyclopropyl |
| 1443. | Br | F | H | $CH_2$-cyclopropyl |
| 1444. | Br | $CH_3$ | H | $CH_2$-cyclopropyl |
| 1445. | Br | $OCH_3$ | H | $CH_2$-cyclopropyl |
| 1446. | Br | Br | H | $CH_2$-cyclopropyl |
| 1447. | Br | $CF_3$ | H | $CH_2$-cyclopropyl |
| 1448. | Br | $OCF_3$ | H | $CH_2$-cyclopropyl |
| 1449. | Br | Cl | H | cyclobutyl |
| 1450. | Br | F | H | cyclobutyl |
| 1451. | Br | $CH_3$ | H | cyclobutyl |
| 1452. | Br | $OCH_3$ | H | cyclobutyl |
| 1453. | Br | Br | H | cyclobutyl |
| 1454. | Br | $CF_3$ | H | cyclobutyl |
| 1455. | Br | $OCF_3$ | H | cyclobutyl |
| 1456. | Br | Cl | H | cyclopentyl |
| 1457. | Br | F | H | cyclopentyl |
| 1458. | Br | $CH_3$ | H | cyclopentyl |
| 1459. | Br | $OCH_3$ | H | cyclopentyl |
| 1460. | Br | Br | H | cyclopentyl |
| 1461. | Br | $CF_3$ | H | cyclopentyl |
| 1462. | Br | $OCF_3$ | H | cyclopentyl |
| 1463. | Br | Cl | H | cyclohexyl |
| 1464. | Br | F | H | cyclohexyl |
| 1465. | Br | $CH_3$ | H | cyclohexyl |
| 1466. | Br | $OCH_3$ | H | cyclohexyl |
| 1467. | Br | Br | H | cyclohexyl |
| 1468. | Br | $CF_3$ | H | cyclohexyl |
| 1469. | Br | $OOF_3$ | H | cyclohexyl |
| 1470. | Br | H | Cl | H |
| 1471. | Br | H | F | H |
| 1472. | Br | H | $CH_3$ | H |
| 1473. | Br | H | $OCH_3$ | H |
| 1474. | Br | H | Br | H |
| 1475. | Br | H | $CF_3$ | H |
| 1476. | Br | H | $OCF_3$ | H |
| 1477. | Br | H | Cl | $CH_3$ |
| 1478. | Br | H | F | $CH_3$ |
| 1479. | Br | H | $CH_3$ | $CH_3$ |
| 1480. | Br | H | $OCH_3$ | $CH_3$ |
| 1481. | Br | H | Br | $CH_3$ |
| 1482. | Br | H | $CF_3$ | $CH_3$ |
| 1483. | Br | H | $OCF_3$ | $CH_3$ |
| 1484. | Br | H | Cl | $C_2H_5$ |
| 1485. | Br | H | F | $C_2H_5$ |
| 1486. | Br | H | $CH_3$ | $C_2H_5$ |
| 1487. | Br | H | $OCH_3$ | $C_2H_5$ |
| 1488. | Br. | H | Br | $C_2H_5$ |
| 1489. | Br | H | $CF_3$ | $C_2H_5$ |
| 1490. | Br | H | $OCF_3$ | $C_2H_5$ |
| 1491. | Br | H | Cl | $n-C_3H_7$ |

TABLE 1-continued (Ia)

| No. | $R^b$ | $R^c$ | $R^d$ | $R^2$ |
|---|---|---|---|---|
| 1492. | Br | H | F | n-C$_3$H$_7$ |
| 1493. | Br | H | CH$_3$ | n-C$_3$H$_7$ |
| 1494. | Br | H | OCH3 | n-C$_3$H$_7$ |
| 1495. | Br | H | Br | n-C$_3$H$_7$ |
| 1496. | Br | H | CF$_3$ | n-C$_3$H$_7$ |
| 1497. | Br | H | OCF$_3$ | n-C$_3$H$_7$ |
| 1498. | Br | H | Cl | CH(CH$_3$)$_2$ |
| 1499. | Br | H | F | CH(CH$_3$)$_2$ |
| 1500. | Br | H | CH$_3$ | CH(CH$_3$)$_2$ |
| 1501. | Br | H | OCH$_3$ | CH(CH$_3$)$_2$ |
| 1502. | Br | H | Br | CH(CH$_3$)$_2$ |
| 1503. | Br | H | CF$_3$ | CH(CH$_3$)$_2$ |
| 1504. | Br | H | OCF$_3$ | CH(CH$_3$)$_2$ |
| 1505. | Br | H | Cl | n-C$_4$H$_9$ |
| 1506. | Br | H | F | n-C$_4$H$_9$ |
| 1507. | Br | H | CH$_3$ | n-C$_4$H$_9$ |
| 1508. | Br | H | OCH$_3$ | n-C$_4$H$_9$ |
| 1509. | Br | H | Br | n-C$_4$H$_9$ |
| 1510. | Br | H | CF$_3$ | n-C$_4$H$_9$ |
| 1511. | Br | H | OCF$_3$ | n-C$_4$H$_9$ |
| 1512. | Br | H | Cl | C(CH$_3$)$_3$ |
| 1513. | Br | H | F | C(CH$_3$)$_3$ |
| 1514. | Br | H | CH$_3$ | C(CH$_3$)$_3$ |
| 1515. | Br | H | OCH$_3$ | C(CH$_3$)$_3$ |
| 1516. | Br | H | Br | C(CH$_3$)$_3$ |
| 1517. | Br | H | CF$_3$ | C(CH$_3$)$_3$ |
| 1518. | Br | H | OCF$_3$ | C(CH$_3$)$_3$ |
| 1519. | Br | H | Cl | C$_6$H$_5$ |
| 1520. | Br | H | F | C$_6$H$_5$ |
| 1521. | Br | H | CH$_3$ | C$_6$H$_5$ |
| 1522. | Br | H | OCH$_3$ | C$_6$H$_5$ |
| 1523. | Br | H | Br | C$_6$H$_5$ |
| 1524. | Br | H | CF$_3$ | C$_6$H$_5$ |
| 1525. | Br | H | OCF$_3$ | C$_6$H$_5$ |
| 1526. | Br | H | Cl | cyclopropyl |
| 1527. | Br | H | F | cyclopropyl |
| 1528. | Br | H | CH$_3$ | cyclopropyl |
| 1529. | Br | H | OCH$_3$ | cyclopropyl |
| 1530. | Br | H | Br | cyclopropyl |
| 1531. | Br | H | CF$_3$ | cyclopropyl |
| 1532. | Br | H | OCF$_3$ | cyclopropyl |
| 1533. | Br | H | Cl | CH$_2$-cyclopropyl |
| 1534. | Br | H | F | CH$_2$-cyclopropyl |
| 1535. | Br | H | CH$_3$ | CH$_2$-cyclopropyl |
| 1536. | Br | H | OCH$_3$ | CH$_2$-cyclopropyl |
| 1537. | Br | H | Br | CH$_2$-cyclopropyl |
| 1538. | Br | H | CF$_3$ | CH$_2$-cyclopropyl |
| 1539. | Br | H | OCF$_3$ | CH$_2$-cyclopropyl |
| 1540. | Br | H | Cl | cyclobutyl |
| 1541. | Br | H | F | cyclobutyl |
| 1542. | Br | H | CH$_3$ | cyclobutyl |
| 1543. | Br | H | OCH$_3$ | cyclobutyl |
| 1544. | Br | H | Br | cyclobutyl |
| 1545. | Br | H | CF$_3$ | cyclobutyl |
| 1546. | Br | H | OCF$_3$ | cyclobutyl |
| 1547. | Br | H | Cl | cyclopentyl |
| 1548. | Br | H | F | cyclopentyl |
| 1549. | Br | H | CH$_3$ | cyclopentyl |
| 1550. | Br | H | OCH$_3$ | cyclopentyl |
| 1551. | Br | H | Br | cyclopentyl |
| 1552. | Br | H | CF$_3$ | cyclopentyl |
| 1553. | Br | H | OCF$_3$ | cyclopentyl |
| 1554. | Br | H | Cl | cyclohexyl |
| 1555. | Br | H | F | cyclohexyl |
| 1556. | Br | H | CH$_3$ | cyclohexyl |
| 1557. | Br | H | OCH$_3$ | cyclohexyl |
| 1558. | Br | H | Br | cyclohexyl |
| 1559. | Br | H | CF$_3$ | cyclohexyl |
| 1560. | Br | H | OCF$_3$ | cyclohexyl |
| 1561. | CH$_3$ | Cl | H | H |
| 1562. | CH$_3$ | F | H | H |
| 1563. | CH$_3$ | CH$_3$ | H | H |
| 1564. | CH$_3$ | OCH$_3$ | H | H |
| 1565. | CH$_3$ | Br | H | H |
| 1566. | CH$_3$ | CF$_3$ | H | H |
| 1567. | CH$_3$ | OCF$_3$ | H | H |
| 1568. | CH$_3$ | Cl | H | CH$_3$ |
| 1569. | CH$_3$ | F | H | CH$_3$ |
| 1570. | CH$_3$ | CH$_3$ | H | CH$_3$ |
| 1571. | CH$_3$ | Br | H | CH$_3$ |
| 1572. | CH$_3$ | CF$_3$ | H | CH$_3$ |
| 1573. | CH$_3$ | OCF$_3$ | H | CH$_3$ |
| 1574. | CH$_3$ | Cl | H | C$_2$H$_5$ |
| 1575. | CH$_3$ | F | H | C$_2$H$_5$ |
| 1576. | CH$_3$ | CH$_3$ | H | C$_2$H$_5$ |
| 1577. | CH$_3$ | Br | H | C$_2$H$_5$ |
| 1578. | CH$_3$ | CF$_3$ | H | C$_2$H$_5$ |
| 1579. | CH$_3$ | OCF$_3$ | H | C$_2$H$_5$ |
| 1580. | CH$_3$ | Cl | H | n-C$_3$H$_7$ |
| 1581. | CH$_3$ | F | H | n-C$_3$H$_7$ |
| 1582. | CH$_3$ | CH$_3$ | H | n-C$_3$H$_7$ |
| 1583. | CH$_3$ | Br | H | n-C$_3$H$_7$ |
| 1584. | CH$_3$ | CF$_3$ | H | n-C$_3$H$_7$ |
| 1585. | CH$_3$ | OCF$_3$ | H | n-C$_3$H$_7$ |
| 1586. | CH$_3$ | Cl | H | CH(CH$_3$)$_2$ |
| 1587. | CH$_3$ | F | H | CH(CH$_3$)$_2$ |
| 1588. | CH$_3$ | CH$_3$ | H | CH(CH$_3$)$_2$ |
| 1589. | CH$_3$ | Br | H | CH(CH$_3$)$_2$ |
| 1590. | CH$_3$ | CF$_3$ | H | CH(CH$_3$)$_2$ |
| 1591. | CH$_3$ | OCF$_3$ | H | CH(CH$_3$)$_2$ |
| 1592. | CH$_3$ | Cl | H | n-C$_4$H$_9$ |
| 1593. | CH$_3$ | F | H | n-C$_4$H$_9$ |
| 1594. | CH$_3$ | CH$_3$ | H | n-C$_4$H$_9$ |
| 1595. | CH$_3$ | Br | H | n-C$_4$H$_9$ |
| 1596. | CH$_3$ | CF$_3$ | H | n-C$_4$H$_9$ |
| 1597. | CH$_3$ | OCF$_3$ | H | n-C$_4$H$_9$ |
| 1598. | CH$_3$ | Cl | H | C(CH$_3$)$_3$ |
| 1599. | CH$_3$ | F | H | C(CH$_3$)$_3$ |
| 1600. | CH$_3$ | CH$_3$ | H | C(CH$_3$)$_3$ |
| 1601. | CH$_3$ | Br | H | C(CH$_3$)$_3$ |
| 1602. | CH$_3$ | CF$_3$ | H | C(CH$_3$)$_3$ |
| 1603. | CH$_3$ | OCF$_3$ | H | C(CH$_3$)$_3$ |
| 1604. | CH$_3$ | Cl | H | C$_6$H$_5$ |
| 1605. | CH$_3$ | F | H | C$_6$H$_5$ |
| 1606. | CH$_3$ | CH$_3$ | H | C$_6$H$_5$ |
| 1607. | CH$_3$ | Br | H | C$_6$H$_5$ |
| 1608. | CH$_3$ | CF$_3$ | H | C$_6$H$_5$ |
| 1609. | CH$_3$ | OCF$_3$ | H | C$_6$H$_5$ |
| 1610. | CH$_3$ | Cl | H | cyclopropyl |
| 1611. | CH$_3$ | F | H | cyclopropyl |
| 1612. | CH$_3$ | CH$_3$ | H | cyclopropyl |
| 1613. | CH$_3$ | Br | H | cyclopropyl |
| 1614. | CH$_3$ | CF$_3$ | H | cyclopropyl |
| 1615. | CH$_3$ | OCF$_3$ | H | cyclopropyl |
| 1616. | CH$_3$ | Cl | H | CH$_2$-cyclopropyl |
| 1617. | CH$_3$ | F | H | CH$_2$-cyclopropyl |
| 1618. | CH$_3$ | CH$_3$ | H | CH$_2$-cyclopropyl |
| 1619. | CH$_3$ | Br | H | CH$_2$-cyclopropyl |
| 1620. | CH$_3$ | CF$_3$ | H | CH$_2$-cyclopropyl |
| 1621. | CH$_3$ | OCF$_3$ | H | CH$_2$-cyclopropyl |

TABLE 1-continued (Ia)

| No. | R$^b$ | R$^c$ | R$^d$ | R$^2$ |
|---|---|---|---|---|
| 1622. | CH$_3$ | Cl | H | cyclobutyl |
| 1623. | CH$_3$ | F | H | cyclobutyl |
| 1624. | CH$_3$ | CH$_3$ | H | cyclobutyl |
| 1625. | CH$_3$ | Br | H | cyclobutyl |
| 1626. | CH$_3$ | CF$_3$ | H | cyclobutyl |
| 1627. | CH$_3$ | OCF$_3$ | H | cyclobutyl |
| 1628. | CH$_3$ | Cl | H | cyclopentyl |
| 1629. | CH$_3$ | F | H | cyclopentyl |
| 1630. | CH$_3$ | CH$_3$ | H | cyclopentyl |
| 1631. | CH$_3$ | Br | H | cyclopentyl |
| 1632. | CH$_3$ | CF$_3$ | H | cyclopentyl |
| 1633. | CH$_3$ | OCF$_3$ | H | cyclopentyl |
| 1634. | CH$_3$ | Cl | H | cyclohexyl |
| 1635. | CH$_3$ | F | H | cyclohexyl |
| 1636. | CH$_3$ | CH$_3$ | H | cyclohexyl |
| 1637. | CH$_3$ | Br | H | cyclohexyl |
| 1638. | CH$_3$ | CF$_3$ | H | cyclohexyl |
| 1639. | CH$_3$ | OCF$_3$ | H | cyclohexyl |
| 1640. | CH$_3$ | H | Cl | H |
| 1641. | CH$_3$ | H | F | H |
| 1642. | CH$_3$ | H | CH$_3$ | H |
| 1643. | CH$_3$ | H | Br | H |
| 1644. | CH$_3$ | H | CF$_3$ | H |
| 1645. | CH$_3$ | H | OCF$_3$ | H |
| 1646. | CH$_3$ | H | Cl | CH$_3$ |
| 1647. | CH$_3$ | H | F | CH$_3$ |
| 1648. | CH$_3$ | H | CH$_3$ | CH$_3$ |
| 1649. | CH$_3$ | H | Br | CH$_3$ |
| 1650. | CH$_3$ | H | CF$_3$ | CH$_3$ |
| 1651. | CH$_3$ | H | OCF$_3$ | CH$_3$ |
| 1652. | CH$_3$ | H | Cl | C$_2$H$_5$ |
| 1653. | CH$_3$ | H | F | C$_2$H$_5$ |
| 1654. | CH$_3$ | H | CH$_3$ | C$_2$H$_5$ |
| 1655. | CH$_3$ | H | Br | C$_2$H$_5$ |
| 1656. | CH$_3$ | H | CF$_3$ | C$_2$H$_5$ |
| 1657. | CH$_3$ | H | OCF$_3$ | C$_2$H$_5$ |
| 1658. | CH$_3$ | H | Cl | n-C$_3$H$_7$ |
| 1659. | CH$_3$ | H | F | n-C$_3$H$_7$ |
| 1660. | CH$_3$ | H | CH$_3$ | n-C$_3$H$_7$ |
| 1661. | CH$_3$ | H | Br | n-C$_3$H$_7$ |
| 1662. | CH$_3$ | H | CF$_3$ | n-C$_3$H$_7$ |
| 1663. | CH$_3$ | H | OCF$_3$ | n-C$_3$H$_7$ |
| 1664. | CH$_3$ | H | Cl | CH(CH$_3$)$_2$ |
| 1665. | CH$_3$ | H | F | CH(CH$_3$)$_2$ |
| 1666. | CH$_3$ | H | CH$_3$ | CH(CH$_3$)$_2$ |
| 1667. | CH$_3$ | H | Br | CH(CH$_3$)$_2$ |
| 1668. | CH$_3$ | H | CF$_3$ | CH(CH$_3$)$_2$ |
| 1669. | CH$_3$ | H | OCF$_3$ | CH(CH$_3$)$_2$ |
| 1670. | CH$_3$ | H | Cl | n-C$_4$H$_9$ |
| 1671. | CH$_3$ | H | F | n-C$_4$H$_9$ |
| 1672. | CH$_3$ | H | CH$_3$ | n-C$_4$H$_9$ |
| 1673. | CH$_3$ | H | Br | n-C$_4$H$_9$ |
| 1674. | CH$_3$ | H | CF$_3$ | n-C$_4$H$_9$ |
| 1675. | CH$_3$ | H | OCF$_3$ | n-C$_4$H$_9$ |
| 1676. | CH$_3$ | H | Cl | C(CH$_3$)$_3$ |
| 1677. | CH$_3$ | H | F | C(CH$_3$)$_3$ |
| 1678. | CH$_3$ | H | CH$_3$ | C(CH$_3$)$_3$ |
| 1679. | CH$_3$ | H | Br | C(CH$_3$)$_3$ |
| 1680. | CH$_3$ | H | CF$_3$ | C(CH$_3$)$_3$ |
| 1681. | CH$_3$ | H | OCF$_3$ | C(CH$_3$)$_3$ |
| 1682. | CH$_3$ | H | Cl | C$_6$H$_5$ |
| 1683. | CH$_3$ | H | F | C$_6$H$_5$ |
| 1684. | CH$_3$ | H | CH$_3$ | C$_6$H$_5$ |
| 1685. | CH$_3$ | H | Br | C$_6$H$_5$ |
| 1686. | CH$_3$ | H | CF$_3$ | C$_6$H$_5$ |
| 1687. | CH$_3$ | H | OCF$_3$ | C$_6$H$_5$ |
| 1688. | CH$_3$ | H | Cl | cyclopropyl |
| 1689. | CH$_3$ | H | F | cyclopropyl |
| 1690. | CH$_3$ | H | CH$_3$ | cyclopropyl |
| 1691. | CH$_3$ | H | Br | cyclopropyl |
| 1692. | CH$_3$ | H | CF$_3$ | cyclopropyl |
| 1693. | CH$_3$ | H | OCF$_3$ | cyclopropyl |
| 1694. | CH$_3$ | H | Cl | CH$_2$-cyclopropyl |
| 1695. | CH$_3$ | H | F | CH$_2$-cyclopropyl |
| 1696. | CH$_3$ | H | CH$_3$ | CH$_2$-cyclopropyl |
| 1697. | CH$_3$ | H | Br | CH$_2$-cyclopropyl |
| 1698. | CH$_3$ | H | CF$_3$ | CH$_2$-cyclopropyl |
| 1699. | CH$_3$ | H | OCF$_3$ | CH$_2$-cyclopropyl |
| 1700. | CH$_3$ | H | Cl | cyclobutyl |
| 1701. | CH$_3$ | H | F | cyclobutyl |
| 1702. | CH$_3$ | H | CH$_3$ | cyclobutyl |
| 1703. | CH$_3$ | H | Br | cyclobutyl |
| 1704. | CH$_3$ | H | CF$_3$ | cyclobutyl |
| 1705. | CH$_3$ | H | OCF$_3$ | cyclobutyl |
| 1706. | CH$_3$ | H | Cl | cyclopentyl |
| 1707. | CH$_3$ | H | F | cyclopentyl |
| 1708. | CH$_3$ | H | CH$_3$ | cyclopentyl |
| 1709. | CH$_3$ | H | Br | cyclopentyl |
| 1710. | CH$_3$ | H | CF$_3$ | cyclopentyl |
| 1711. | CH$_3$ | H | OCF$_3$ | cyclopentyl |
| 1712. | CH$_3$ | H | Cl | cyclohexyl |
| 1713. | CH$_3$ | H | F | cyclohexyl |
| 1714. | CH$_3$ | H | CH$_3$ | cyclohexyl |
| 1715. | CH$_3$ | H | Br | cyclohexyl |
| 1716. | CH$_3$ | H | CF$_3$ | cyclohexyl |
| 1717. | CH$_3$ | H | OCF$_3$ | cyclohexyl |

Particular preference is also given to the 1-phenylpyrrolidin-2-one-3-carboxamides of the formula Ib (≡I where R$^a$=R$^e$=H, X=O, Y=O, R$^1$=H, R$^3$=H and n=0) where R$^b$, R$^c$, R$^d$ and R$^2$ have the meanings given above, in particular the meanings mentioned as being preferred. Examples of such compounds are the compounds Ib.1 to Ib.1717 in which the variables R$^b$, R$^c$, R$^d$ and R$^2$ together have the meanings given in one row of Table 1.

(Ib)

Particular preference is also given to the 1-phenylpyrrolidin-2-one-3-carboxamides of the formula Ic (≡I where R$^a$=R$^e$=H, X=O, Y=O, R$^1$=H, R$^3$=C$_2$H$_5$ and n=0) where R$^b$, R$^c$, R$^d$ and R$^2$ have the meanings given above, in particular the meanings mentioned as being preferred. Examples of such compounds are the compounds Ic.1 to Ic.1717 in which the variables R$^b$, R$^c$, R$^d$ and R$^2$ together have the meanings given in one row of Table 1.

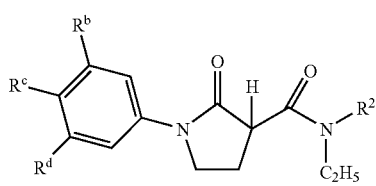

(Ic)

Particular preference is also given to the 1-phenylpyrrolidin-2-one-3-carboxamides of the formula Id (≡I where X=O, Y=O, $R^1$=H, $R^3$=CH(CH$_3$)$_2$ and n=0) where $R^b$, $R^c$, $R^d$ and $R^2$ have the meanings given above, in particular the meanings mentioned as being preferred. Examples of such compounds are the compounds Id.1 to Id.1717 in which the variables $R^b$, $R^c$, $R^d$ and $R^2$ together have the meanings given in one row of Table 1.

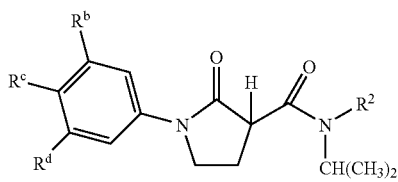

(Id)

Particular preference is also given to the 1-phenylpyrrolidin-2-one-3-carboxamides of the formula Ie (≡I where X=O, Y=O, $R^1$=H, $R^3$=H, A=O and n=1) where $R^b$, $R^c$, $R^d$ and $R^2$ have the meanings given above, in particular the meanings mentioned as being preferred. Examples of such compounds are the compounds Ie.1 to Ie.1717 in which the variables $R^b$, $R^c$, $R^d$ and $R^2$ together have the meanings given in one row of Table 1.

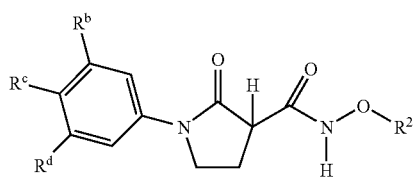

(Ie)

Particular preference is also given to the 1-phenylpyrrolidin-2-one-3-carboxamides of the formula If (≡I where X=O, Y=O, $R^1$=H, $R^3$=CH$_3$, A=O and n=1) where $R^b$, $R^c$, $R^d$ and $R^2$ have the meanings given above, in particular the meanings mentioned as being preferred. Examples of such compounds are the compounds If.1 to If.1717 in which the variables $R^b$, $R^c$, $R^d$ and $R^2$ together have the meanings given in one row of Table 1.

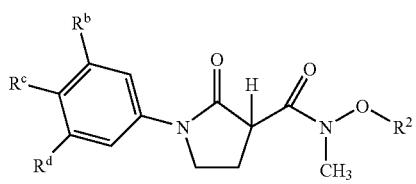

(If)

Particular preference is also given to the 1-phenylpyrrolidin-2-one-3-carboxamides of the formula Ig (≡I where X=O, Y=O, $R^1$=H, $R^3$=C$_2$H$_5$, A=O and n=1) where $R^b$, $R^c$, $R^d$ and $R^2$ have the meanings given above, in particular the meanings mentioned as being preferred. Examples of such compounds are the compounds Ig.1 to Ig.1717 in which the variables $R^b$, $R^c$, $R^d$ and $R^2$ together have the meanings given in one row of Table 1.

(Ig)

Particular preference is also given to the 1-phenylpyrrolidin-2-one-3-carboxamides of the formula Ih (≡I where X=O, Y=O, $R^1$H, $R^3$=CH(CH$_3$)$_2$, A=O and n=1) where $R^b$, $R^c$, $R^d$ and $R^2$ have the meanings given above, in particular the meanings mentioned as being preferred. Examples of such compounds are the compounds Ih.1 to Ih.1717 in which the variables $R^b$, $R^c$, $R^d$ and $R^2$ together have the meanings given in one row of Table 1.

(Ih)

Particular preference is also given to the 1-phenylpyrrolidin-2-one-3-carboxamides of the formula Ii (≡I where X=O, Y=O, $R^1$=H, $R^3$=H, n=1 and A=NR$^{12}$ where $R^{12}$=H) where $R^b$, $R^c$, $R^d$ and $R^2$ have the meanings given above, in particular the meanings mentioned as being preferred. Examples of such compounds are the compounds Ii.1 to Ii.1717 in which the variables $R^b$, $R^c$, $R^d$ and $R^2$ together have the meanings given in one row of Table 1.

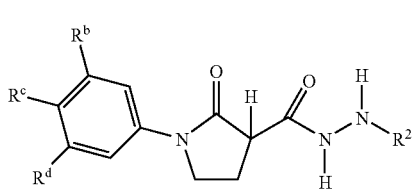

(Ii)

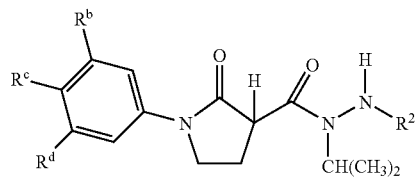

(Il)

Particular preference is also given to the 1-phenylpyrrolidin-2-one-3-carboxamides of the formula Ij (≡I where X=O, Y=O, $R^1$=H, $R^3$=$CH_3$, n=1 and A=$NR^{12}$ where $R^{12}$=H) where $R^b$, $R^c$, $R^d$ and $R^2$ have the meanings given above, in particular the meanings mentioned as being preferred. Examples of such compounds are the compounds Ij.1 to Ij.1717 in which the variables $R^b$, $R^c$, $R^d$ and $R^2$ together have the meanings given in one row of Table 1.

Particular preference is also given to the 1-phenylpyrrolidin-2-one-3-carboxamides of the formula Im (≡I where X=O, Y=O, $R^1$=H, $R^3$=H, n=1 and A=$NR^{12}$ where $R^{12}$=$CH_3$) where $R^b$, $R^c$, $R^d$ and $R^2$ have the meanings given above, in particular the meanings mentioned as being preferred. Examples of such compounds are the compounds Im.1 to Im.1717 in which the variables $R^b$, $R^c$, $R^d$ and $R^2$ together have the meanings given in one row of Table 1.

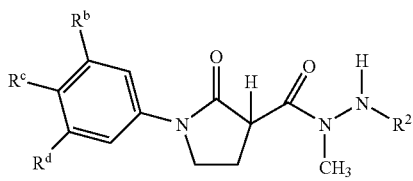

(Ij)

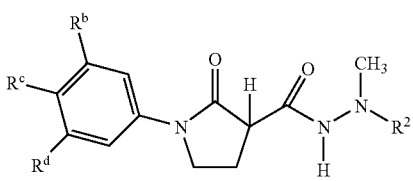

(Im)

Particular preference is also given to the 1-phenylpyrrolidin-2-one-3-carboxamides of the formula Ik (≡I where X=O, Y=O, $R^1$=H, $R^3$=$C_2H_5$, n=1 and A=$NR^{12}$ where $R^{12}$=H) where $R^b$, $R^c$, $R^d$ and $R^2$ have the meanings given above, in particular the meanings mentioned as being preferred. Examples of such compounds are the compounds Ik.1 to Ik.1717 in which the variables $R^b$, $R^c$, $R^d$ and $R^2$ together have the meanings given in one row of Table 1.

Particular preference is also given to the 1-phenylpyrrolidin-2-one-3-carboxamides of the formula In (≡I where X=O, Y=O, $R^1$=H, $R^3$=$CH_3$, n=1 and A=$NR^{12}$ where $R^{12}$=$CH_3$) where $R^b$, $R^c$, $R^d$ and $R^2$ have the meanings given above, in particular the meanings mentioned as being preferred. Examples of such compounds are the compounds In.1 to In.1717 in which the variables $R^b$, $R^c$, $R^d$ and $R^2$ together have the meanings given in one row of Table 1.

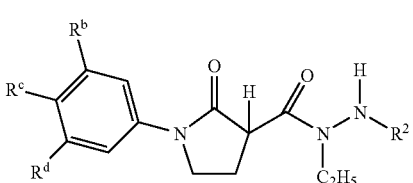

(Ik)

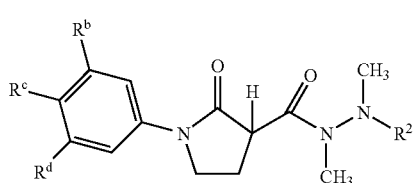

(In)

Particular preference is also given to the 1-phenylpyrrolidin-2-one-3-carboxamides of the formula Il (≡I where X=O, Y=O, $R^1$=H, $R^3$=$CH(CH_3)_2$, n=1 and A=$NR^{12}$ where $R^{12}$=H) where $R^b$, $R^c$, $R^d$ and $R^2$ have the meanings given above, in particular the meanings mentioned as being preferred. Examples of such compounds are the compounds Il.1 to Il.1717 in which the variables $R^b$, $R^c$, $R^d$ and $R^2$ together have the meanings given in one row of Table 1.

Particular preference is also given to the 1-phenylpyrrolidin-2-one-3-carboxamides of the formula Io (≡I where X=O, Y=O, $R^1$=H, $R^3$=$C_2H_5$, n=1 and A=$NR^{12}$ where $R^{12}$=$CH_3$) where $R^b$, $R^c$, $R^d$ and $R^2$ have the meanings given above, in particular the meanings mentioned as being preferred. Examples of such compounds are the compounds Io.1 to Io.1717 in which the variables $R^b$, $R^c$, $R^d$ and $R^2$ together have the meanings given in one row of Table 1.

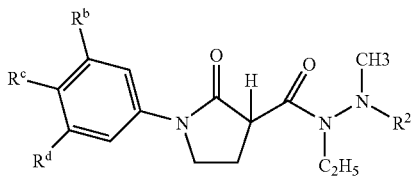

(Io)

Particular preference is also given to the 1-phenylpyrrolidin-2-one-3-carboxamides of the formula Ip (≡I where X=O, Y=O, $R^1$=H, $R^3$=CH(CH$_3$)$_2$, n=1 and A=NR$^{12}$ where $R^{12}$=CH$_3$) where $R^b$, $R^c$, $R^d$ and $R^2$ have the meanings given above, in particular the meanings mentioned as being preferred. Examples of such compounds are the compounds Ip.1 to Ip.1717 in which the variables $R^b$, $R^c$, $R^d$ and $R^2$ together have the meanings given in one row of Table 1.

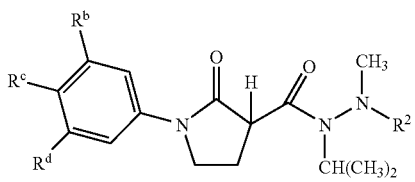

(Ip)

The 1-phenylpyrrolidin-2-one-3-carboxamides of the formula I according to the invention can be prepared, for example, by one of the processes A to G described below.

A) Amidation of a Carboxylic Acid II or a Carboxylic Acid Derivative of II

The preparation of the compound I according to the invention can be carried out, for example, according to Scheme 1 by reacting an activated form of a pyrrolidine-3-carboxylic acid of the formula II with an amine III.

Scheme 1:

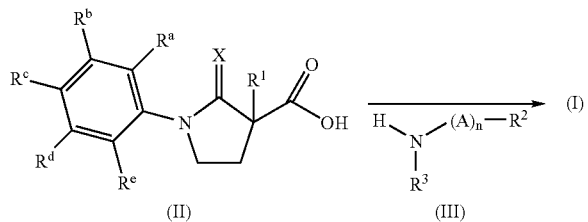

In Scheme 1, the variables $R^1$, X, $R^a$, $R^b$, $R^c$, $R^d$, $R^e$, A, n, $R^2$ and $R^3$ are as defined above. Such reactions are known, for example from WO 01/83459, and can be applied in an analogous manner to the reaction illustrated in Scheme 1. The carboxylic acid II is preferably initially activated by carrying out the reaction in the presence of a coupling agent. Suitable coupling agents are, for example, N,N'-carbonyldiimidazole or carbodiimides, such as dicyclohexylcarbodiimide. These compounds are generally employed in at least equimolar amount and up to a four-fold excess, based on the carboxylic acid II. If appropriate, it may be advantageous to carry out the reaction of the carboxylic acid II with the coupling agent in the presence of a catalytic amount of a tertiary aminopyridine, such as 4-dimethylaminopyridine (DMAP). In this case, the amount of aminopyridine added is preferably 5 to 10 mol %, based on the carboxylic acid II. The reaction is usually carried out in a solvent. Suitable solvents are, for example, chlorinated hydrocarbons, such as methylene chloride, 1,2-dichloroethane, ethers, for example dialkyl ethers, such as diethyl ether, methyl tert-butyl ether, or cyclic ethers, such as tetrahydrofuran or dioxane, carboxamides, such as dimethylformamide, N-methyllactams, such as N-methylpyrrolidone, nitriles, such as acetonitrile, aromatic hydrocarbons, such as toluene, or mixtures of these.

The molar ratio of amine III to carboxylic acid II is generally at least 0.9:1, preferably at least 1:1. If appropriate, it may be advantageous to employ the amine in a slight excess, for example in an excess of up to 30%, based on the carboxylic acid II.

In general, the reaction temperature is in the range from 0° C. to the boiling point of the solvent.

Alternatively, the carboxylic acid II can initially be activated by converting it into its acid halide, preferably its acid chloride. Means for this purpose are known, for example from U.S. Pat. No. 4,874,422. Suitable compounds are inorganic acid halides, preferably acid chlorides, such as thionyl chloride, phosphoryl chloride phosphorus pentachloride or phosphorus trichloride, and organic acid chlorides, such as oxalyl chloride. The acid halide of II formed can be isolated and then be reacted with the amine III. It is also possible to react the acid chloride of II formed directly, without isolation, with the amine III. If appropriate, the reactivity of the acid halide is enhanced by adding catalytic amounts of an N,N-dialkylcarboxamide, such as dimethylformamide. The halogenating agent is usually employed in an at least equimolar amount, based on the carboxylic acid II. The acid halides thionyl chloride, phosphorus trichloride or phosphoryl chloride can simultaneously act as solvent. Suitable solvents are furthermore-solvents which are inert under the reaction conditions, for example chlorinated hydrocarbons, such as methylene chloride, 1,2-dichloroethane, aromatic hydrocarbons, such as benzene or toluene, aliphatic and cycloaliphatic hydrocarbons, such as hexane, petroleum ether, cyclohexane, and mixtures thereof. The reaction temperature is generally between room temperature and the boiling point of the solvent. After the reaction has ended, excess halogenating agent is generally removed. The resulting acid halide of II is then reacted with the amine III. In general, the amine III is dissolved in the solvent which was also used for preparing the carbonyl halide, unless the solvent is one of the acid halides mentioned above.

If appropriate, the reaction is carried out in the presence of an auxiliary base which is preferably employed in an equimolar amount or an up to four-fold excess, based on the carboxylic acid II. Suitable bases are, for example, amines such as 1,5-diazabicyclo[4.3.0]non-5-ene (DBN), 1,8-diazabicyclo[5.4.0]undec-7-ene (DBU), pyridine, α-, β-, γ-lutidine or triethylamine.

It is, of course, also possible to use other methods for activating the carboxylic acid II. Such methods are described in the prior art, for example in J. Falbe, Houben Weyl, Methoden der Organischen Chemie [Methods of organic chemistry], Vol. E5, 4th Ed., 1985, p. 941 ff.

In a further process variant, the corresponding carboxylic acid ester of II (carboxylic acid ester VI), in particular the $C_1$-$C_4$-alkyl ester of II and especially the methyl or ethyl ester of II, is reacted with the amine III, if appropriate in the presence of a base. Regarding a suitable base, solvent and reaction temperatures, reference is made to what was said above. The preparation of the carboxylic acid ester VI is described below.

Compounds of the formula II where $R^1$=H can be prepared, for example, similarly to a process described in Journal of Heterocyclic Chemistry, 3 (1966), 311. The synthesis is shown in Scheme 2.

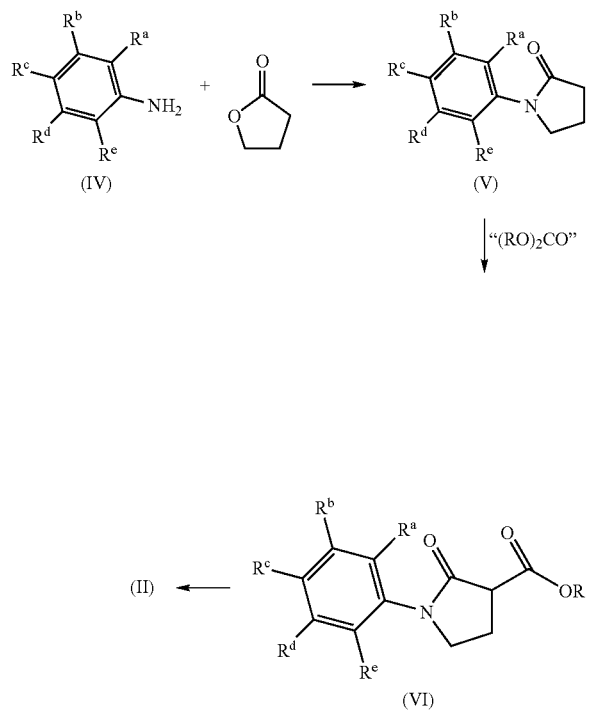

In Scheme 2, the variables $R^a$, $R^b$, $R^c$, $R^d$, $R^e$ are as defined above and R is $C_1$-$C_4$-alkyl. The reaction of the aniline compound IV with butyrolactone is usually carried out in the presence of an inorganic acid, such as sulfuric acid, phosphoric acid or hydrochloric acid, or in the presence of an organic acid, such as acetic acid. The reaction can be carried out in the absence of a solvent or in the presence of a solvent. Suitable solvents are all solvents which are inert under the reaction conditions. However, the reaction is preferably carried out in the absence of a solvent. If the reaction is carried out in the absence of a solvent, the butyrolactone is employed in an excess, based on the aniline IV. The reaction temperatures are generally in the range of from 20° C. to the boiling point of the solvent.

In the next step, the resulting pyrrolidinone V is generally reacted without further purification, for example with a carbonate $(RO)_2CO$ or a synthetic equivalent, such as a chloroformic ester. To this end, the pyrrolidinone V is generally initially converted into the corresponding enolate by treatment with a suitable base. Suitable bases include in particular organolithium compounds, such as n-butyllithium, tert-butyllithium and phenyllithium, lithium amides, such as lithium diisopropylamide, and alkali metal hydrides, such as sodium hydride. The reaction is generally carried out in an organic solvent. Suitable solvents are inert solvents, such as aliphatic and cycloaliphatic hydrocarbons, such as hexane, petroleum ether, cyclohexane, ethers, for example dialkyl ethers, such as diethyl ether, methyl tert-butyl ether, or cyclic ethers, such as tetrahydrofuran or dioxane, and also mixtures of these. In general, the deprotonation of the compound V is carried out at low temperatures to about room temperature, preferably at about 0° C. To this end, the base is employed in an at least equimolar amount, preferably a 1.1- to 4-fold molar excess, based on the compound V.

The subsequent introduction of the alkoxycarbonyl group is carried out, for example, using a carbonic acid diester, such as dimethyl carbonate or diethyl carbonate. The carbonic acid diester and the enolate of the compound V are usually employed in equimolar amounts. It is, of course, possible for one of the two reactants to be employed in a slight excess. The temperature required for the reaction is generally in the range of from 0° C. to the boiling point of the solvent.

The carboxylic acid ester VI is then hydrolyzed by known methods (see, for example, Organikum, 17th Edition, VEB Deutscher Verlag der Wissenschaften, 1988, p. 415) to give the carboxylic acid II. The hydrolysis can be carried out either in acidic medium using strong mineral acids, such as concentrated hydrochloric acid or sulfuric acid, or organic acids, such as glacial acetic acid, or mixtures of these in the presence of water, or in alkaline medium using bases, such as alkali metal hydroxide, for example sodium hydroxide or potassium hydroxide, if appropriate in the presence of water.

Suitable solvents both for acidic and basic hydrolysis of esters are, for example, ethers, for example dialkyl ethers, such as diethyl ether, methyl tert-butyl ether, or cyclic ethers, such as tetrahydrofuran or dioxane, alcohols, water and mixtures of these solvents. The reaction temperature is usually between room temperature and the boiling point of the solvent.

The compounds II can furthermore be prepared by aminoethylation of malonic acid esters VII in which $R^1$ is as defined above and R is $C_1$-$C_4$-alkyl with phenylaziridines VII and subsequent hydrolysis. The synthesis is shown in Scheme 3 and can be carried out similarly to known methods as described, for example, in Archiv der Pharmazie (Weinheim) 302(4) (1969), 253, Justus Liebigs Ann. Chem. 716 (1968), 121-126 or in Angew. Chem. 74, (1962), 694.

Scheme 3:

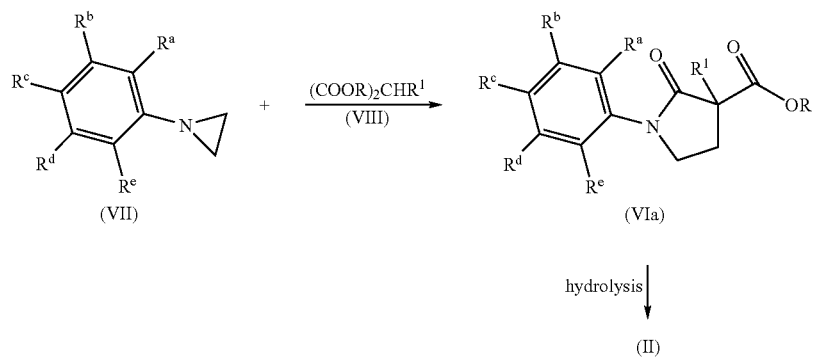

The reaction is generally carried out in the presence of LiH/LiI in a solvent. Suitable solvents include aromatic solvents, such as benzene, toluene or xylene. Frequently, the aziridine VII and the malonic acid ester are employed in approximately equimolar amounts. It may be advantageous to employ an excess of malonic acid ester VIII, preferably an excess of up to 30%, based on the aziridine VII. The resulting ester VIa is then converted according to known methods by hydrolysis in acidic or alkaline medium into the corresponding carboxylic acids II. With regard to ester hydrolysis, reference is made to what was said above.

Compounds of the formula II in which $R^1$ is H can furthermore be prepared similarly to a process described in JP 2000143624-A. To this end, anilines IV are reacted with 1,1-cyclopropanedicarboxylic acid. The synthesis route is shown in Scheme 4. The reaction is usually carried out in water or in an aliphatic nitrile, such as acetonitrile, or in mixtures thereof with water, at temperatures between 40 and 100° C.

Scheme 4:

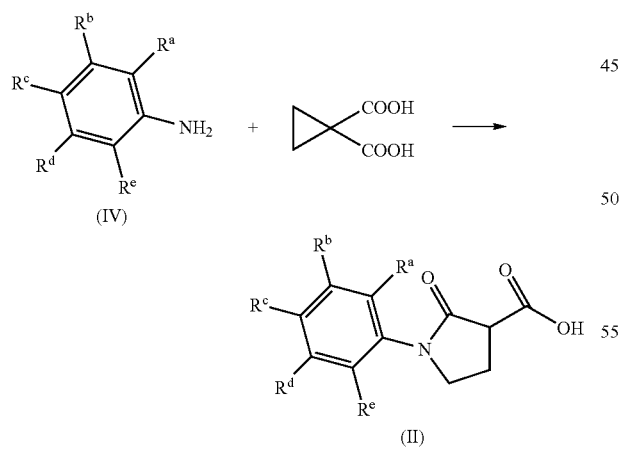

Compounds of the formula II in which $R^1$ is H can furthermore be obtained similarly to processes described in J. Am. Chem. Soc. 97 (1975), 3239 or Organic Synthesis 60, (1981), 66. The reaction of the aniline IV with the dioxaspirooctanedione IX gives the carboxylic acid II. The synthesis route is shown in Scheme 5.

Scheme 5:

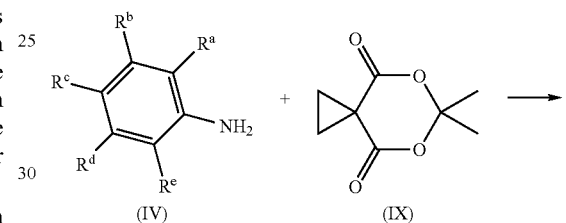

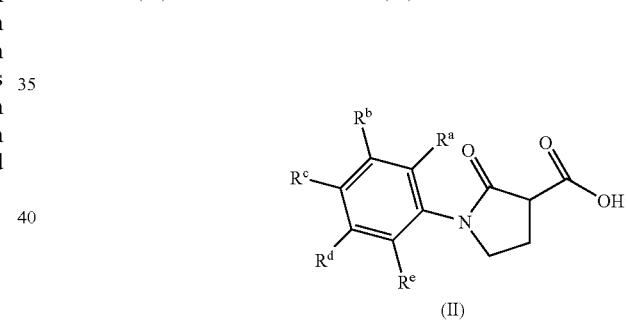

B) Linking a Pyrrolidinone X to an Aromatic Compound XI

Compounds of the formula I can furthermore be prepared by reacting suitably substituted pyrrolidinones X with aromatic compounds of the formula XI according to the synthesis shown in Scheme 6.

Scheme 6:

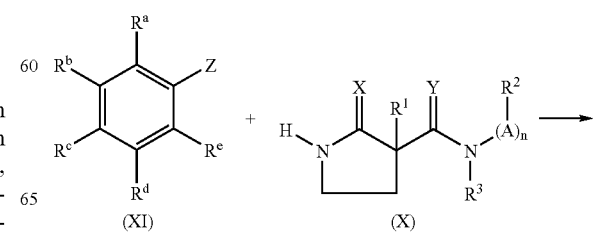

-continued

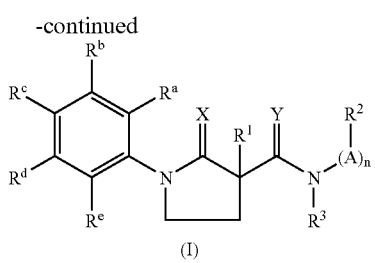

In Scheme 6, the variables $R^a$, $R^b$, $R^c$, $R^d$, $R^d$, $R^e$, X, Y, A, n, $R^1$, $R^2$ and $R^3$ are as defined above. Z is halogen, preferably fluorine, chlorine or bromine, or $B(OH)_2$, $B(OR')_2$ or $Sn(R')_3$. In these radicals, R' is aryl, such as phenyl, or $C_1$-$C_{10}$-alkyl.

The reaction is preferably carried out in a solvent, in particular a polar aprotic solvent, such as dimethylformamide, dimethyl sulfoxide, N-methylpyrrolidone, dimethylacetamide, an ether, such as diethyl ether, tetrahydrofuran or dioxane, and mixtures of these solvents.

In general, the reaction is carried out at temperatures above room temperature, preferably in the range from 50 to 200° C. To this end, the compounds of the formulae X and XI are preferably employed in approximately equimolar amounts. It is, of course, also possible to use an excess of one of the components, the excess preferably being not more than 50 mol %, in particular not more than 20 mol %, based on the component which is present in a substoichiometric amount.

The compounds I according to the invention are furthermore obtained by coupling XI (for example Z=Cl, Br, I, $B(OR)_2$, $SnR_3$) with a pyrrolidinone X, preferably in the presence of catalytically active amounts of a palladium, copper or nickel compound, if appropriate in the presence of a base, in an organic solvent or a mixture of a solvent with water, at room temperature or elevated temperatures. Processes for coupling a phenylboronic acid are described, for example, in WO 02/42275.

Suitable palladium catalysts are, in addition to palladium carboxylates, such as palladium(II) acetate, also palladium/phosphine complexes, such as tetrakistriphenylphosphinepalladium, bistriphenylphosphinepalladium(II) chloride, bis(1,2-diphenylphosphinoethane)palladium(II) chloride, bis(1,3-diphenylphosphinopropane)palladium(II) chloride, bis(1,4-diphenylphosphinobutane)palladium(II) chloride and bis(diphenylphosphino)ferrocenylpalladium(II) chloride. However, it is also possible to react palladium halides such as palladium(II) chloride in situ with phosphine ligands, giving the catalytically active complexes. Suitable phosphine ligands are, for example, arylphosphines which are unsubstituted or substituted in the ortho-, meta- or para-position by halogen, alkyl and/or $SO_3H$, such as triphenylphosphine, 1,2-bis(diphenylphosphino)ethane, 1,3-bis(diphenylphosphino)propane, 1,4-bis(diphenylphosphino)butane, bis(diphenylphosphino)ferrocene, hetarylphosphines, such as trifurylphosphine or tripyridylphosphine.

Suitable Ni catalysts are nickel(II) acetylacetonate alone or in combination with the abovementioned phosphine ligands, or Ni(II) acetylacetonate with imidazolium carbene ligands, and also complexes of nickel(II) salts with the above mentioned phosphine ligands, for example bis(triphenylphosphine)nickel(II) chloride, [1,3-bis(diphenylphosphino)propane]nickel(II) chloride, [1,4-bis(diphenylphosphino)butane]nickel(II) chloride and [bis(diphenylphosphino)ferrocene]nickel(II) chloride.

Suitable copper compounds are, in particular, copper(I) compounds, such as CuCl, CuBr and the like.

The catalyst is usually employed in substoichiometric amounts, preferably of 0.001-0.8 equivalents and particularly preferably of 0.01 to 0.5 equivalents, based on the pyrrolidinone XI used.

If appropriate, it may be advantageous to convert the compound X initially with a base into its salt. Suitable bases are, for example, alkali metal hydrides, such as sodium hydride, and sodium alkoxides, such as sodium methoxide and sodium ethoxide, lithium amides, such as lithium diisopropylamide, and also organolithium compounds, such as butyllithium and phenyllithium.

The molar ratio of compound XI to compound X is preferably in the range from 0.95:1 to 1:1.5.

Suitable bases are, if required, alkali metal and alkaline earth metal hydroxides, alkali metal (bi)carbonates and alkali metal phosphates, such as NaOH, $NaHCO_3$, $Na_2CO_3$, $KHCO_3$, $K_2CO_3$, $Ba(OH)_2$, $K_3PO_4$, alkali metal, alkaline earth metal, thallium and transition metal alkoxides, such as sodium ethoxide and thallium ethoxide. Other suitable bases are alkali metal fluorides, such as potassium fluoride, cesium fluoride, ammonium fluorides and tetrabutylammonium fluoride. The base is usually employed in an approximately stoichiometric amount or in up to 10-fold excess, based on the compound II.

Suitable solvents are organic solvents, such as DMF, dimethylacetamide, toluene, tetrahydrofuran (THF), dioxane and dimethoxyethane. If the coupling is carried out with boronic acid, the abovementioned solvents can also be employed in a mixture with water, for example in a ratio of about 5:1 to 1:5, preferably in a ratio of about 2:1 to 1:2 and in particular of about 1:1.

The reaction temperature is usually above the melting point and can be up to the boiling point of the solvent. It is preferably in the range between 50 and 150° C.

The pyrrolidino compounds X can be prepared by customary processes, for example analogously to the procedure described in process A.

C) Alkylation of Compounds of the Formula I in which $R^1$=H

Compounds of the formula I in which $R^1$ is hydrogen can be prepared according to general methods by treatment with an alkylation agent $R^1$-L in compounds of the formula I in which $R^1$ is not hydrogen. The synthesis route is shown in Scheme 7.

Scheme 7:

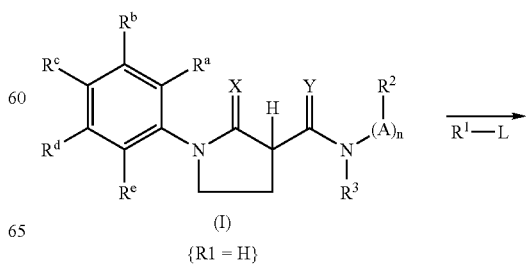

{R1 = H}

-continued

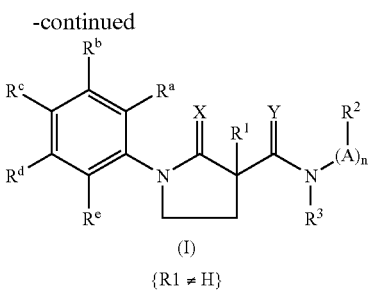
(I)
{R1 ≠ H}

In Scheme 7, the variables $R^1$, $R^a$, $R^b$, $R^c$, $R^d$, $R^d$, $R^e$, X, Y, A, n, $R^1$, $R^2$ and $R^3$ are as defined above. L is a nucleophilically displaceable leaving group, such as halogen, for example chlorine, bromine, iodine, or imidazolyl, carboxylate, such as acetate, arylsulfonate or alkylsulfonate, for example mesylate or triflate. The reaction is usually carried out in the presence of a base. Suitable bases include alkali metal or alkaline earth metal hydroxides, metal hydrides, such as alkali metal hydrides, for example sodium hydride, tertiary alkylamines, such as triethylamine, aromatic amines, such as pyridine, α-, β-, γ-lutidine, lithium diisopropylamide.

Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran, dioxane, polar aprotic solvents, such as acetonitrile, dimethylformamide or dimethyl sulfoxide.

In general, the reaction temperature is in the range from 0° C. to the boiling point of the reaction mixture.

D) Sulfurization of the Compounds of the Formula I in which X or Y is Oxygen.

Compounds of the formula I in which X or Y is oxygen can be prepared according to general methods by treatment with a sulfurizing agent in compounds of the formula I in which X or Y is sulfur. This synthesis route is illustrated in Scheme 8.

Scheme 8:

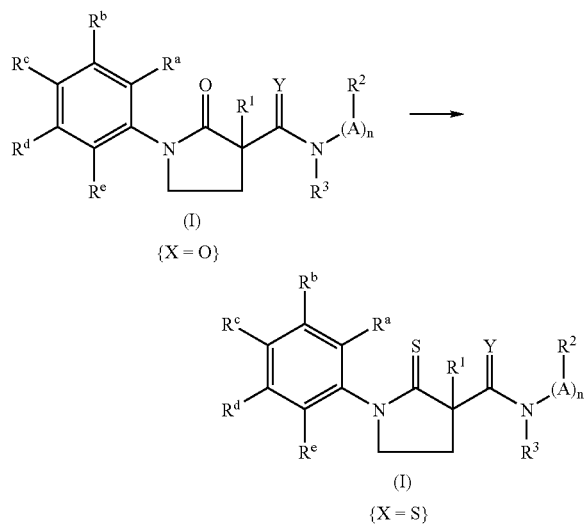

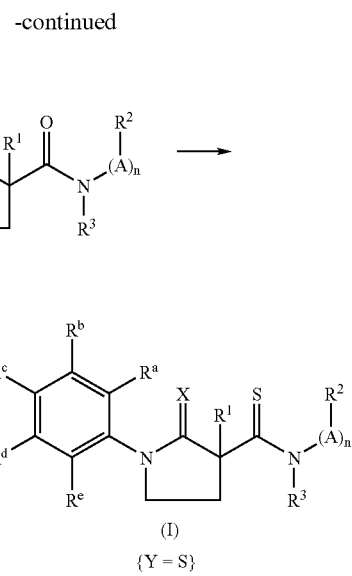

In Scheme 8, the variables $R^a$, $R^b$, $R^c$, $R^d$, $R^d$, $R^e$, X, Y, A, n, $R^1$, $R^2$ and $R^3$ are as defined above. Examples of suitable sulfurizing agents are phosphorus(V) sulfides, organotin sulfides, and also organophosphorus sulfides (see also J. March, Advanced Organic Synthesis, 2nd Edition, Wiley Interscience 1985, p. 794 and the literature cited therein). Particularly suitable sulfurizing agents are phosphorus(V) sulfide and 2,4-bis(4-methoxyphenyl)-1,3,2,4-dithiadiphosphetane-2,4-dithione ("Lawesson's reagent"). Sulfurization processes are described, for example, in WO 95/33718. The reaction can be carried out in a solvent or neat. Suitable solvents are all solvents which are inert under the reaction conditions, for example aromatic hydrocarbons, such as benzene, toluene, xylene, chlorobenzene, basic solvents, such as pyridine, ethers, such as diethyl ether, 1,2-dimethoxyethane or tetrahydrofuran, etc. The temperatures required for the reaction are generally above room temperature and in particular in the range of from 50° C. to the boiling point of the reaction mixture.

E) Condensation of an Anilide XII

A further route to the compounds I according to the invention is the reaction of an anilide XII with a suitable difunctional compound L-CH$_2$—CH$_2$-L' with ring closure according to Scheme 9.

Scheme 9:

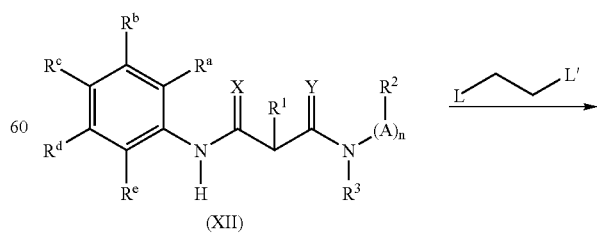

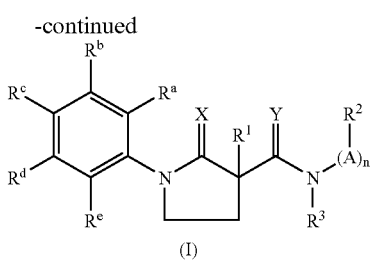

In Scheme 9, the variables $R^a$, $R^b$, $R^c$, $R^d$, $R^d$, $R^e$, X, Y, A, n, $R^1$, $R^2$ and $R^3$ are as defined above, L is as defined in C) and L' has the meaning of L.

The cyclization is carried out in the presence of a base. Suitable bases are all bases mentioned under C). In general, the reaction is carried out in an inert solvent. Suitable solvents are in particular chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran, dioxane, polar aprotic solvents, such as acetonitrile, dimethylformamide or dimethyl sulfoxide. The starting material XII and the difunctional compound L-CH$_2$—CH$_2$-L' are expediently employed in approximately equimolar amounts; however, to optimize the conversion, it may be advantageous to use an excess of one of the two components. The reaction is generally carried out at a temperature between room temperature and the boiling point of the reaction mixture.

The starting materials XII can be prepared in two steps similarly to the process described in Synlett 12 (1969), 1209. In the first step, an isocyanate XIII is reacted with meldrum acid (2,2-dimethyl-1,3-dioxane-4,6-dione). In the second step, the resulting product is then reacted with a suitable amine III. In Scheme 10, the variables $R^a$, $R^b$, $R^c$, $R^d$, $R^d$, $R^e$, X, Y, A, n, $R^1$, $R^2$ and $R^3$ are as defined above.

F) Condensations

F.1 Condensation of Anilines IV with tetrahydro-2-furanones XIV

The compounds I according to the invention can be prepared, for example, by condensing anilines IV with tetrahydro-2-furanones XIV according to the synthesis route shown in Scheme 11. Analogous reactions are known, for example from Tetrahedron Letters, 31 (21) (1990), 2991, and can be applied to the preparation of the compounds according to the invention.

Scheme 11:

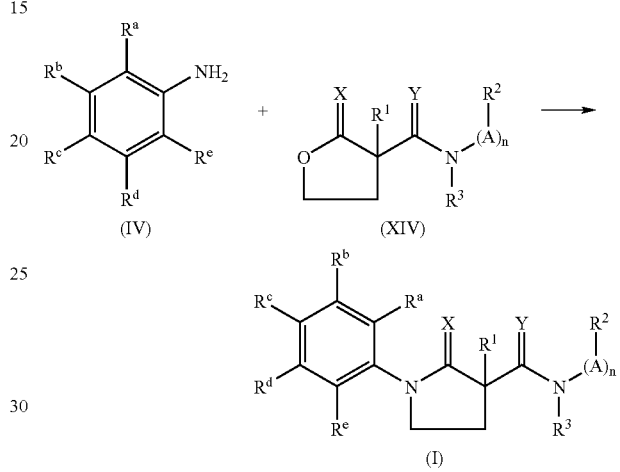

In Scheme 11, the variables $R^a$, $R^b$, $R^c$, $R^d$, $R^d$, $R^e$, X, Y, A, n, $R^1$, $R^2$ and $R^3$ are as defined above. The reaction of the anilines IV is usually carried out in a carboxylic acid, such as acetic acid, at temperatures in the range from 0° C. to 100° C. In general, the starting materials are employed in equimolar amounts, or one of the two components is employed in excess.

Scheme 10:

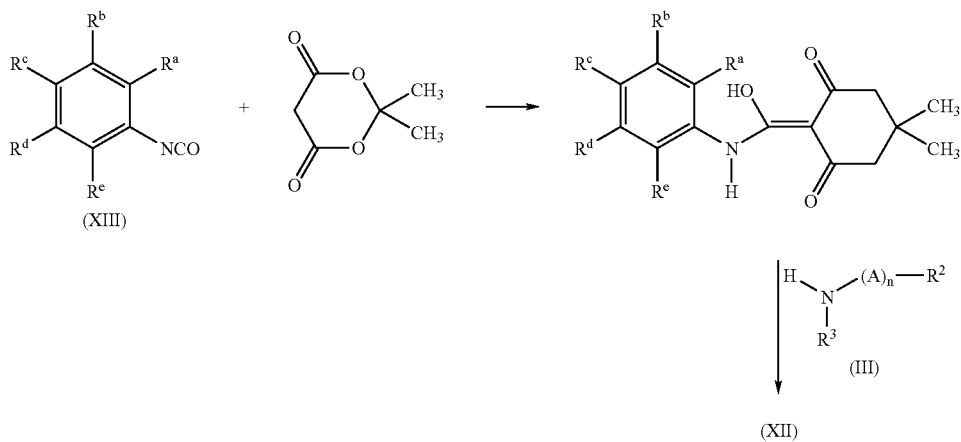

F.2 Condensation of Anilines IV with Carboxylic Acid Derivatives XV and Subsequent Cyclization The compounds I according to the invention can be prepared, for example, by condensing anilines IV with carboxylic acid derivatives XV according to the synthesis route shown in Scheme 12.

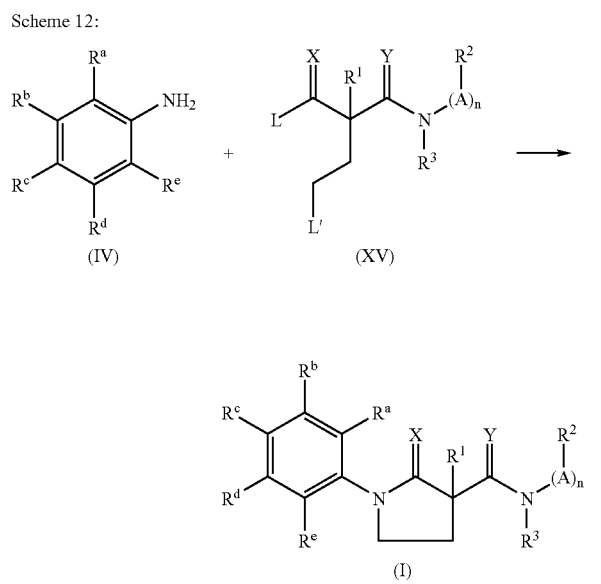

In Scheme 12, the variables $R^a$, $R^b$, $R^c$, $R^d$, $R^d$, $R^e$, X, Y, A, n, $R^1$, $R^2$ and $R^3$ are as defined above. L is as defined in C) and L' has the meaning of L. The reaction of the aniline IV with the carboxylic acid derivative XV is usually carried out in the presence of a base. Suitable bases are, for example, amines, such as 1,5-diazabicyclo[4.3.0]non-5-ene (DBN), 1,8-diazabicyclo[5.4.0]undec-7-ene (DBU), pyridine or triethylamine. The base is usually employed in up to six-fold excess, based on the carboxylic acid derivative XV. The reaction is generally carried out in a solvent. Suitable solvents are, for example, chlorinated hydrocarbons, such as methylene chloride, 1,2-dichloroethane, ethers, for example dialkyl ethers, such as diethyl ether, methyl tert-butyl ether, or cyclic ethers, such as tetrahydrofuran or dioxane, carbonamides, such as dimethylformamide, N-methyllactams, such as N-methylpyrrolidone, nitriles, such as acetonitrile, aromatic hydrocarbons, such as toluene, aromatic amines, such as pyridine, or mixtures of these. In general, the reaction temperature is in a range of from 0° C. to the boiling point of the solvent.

G) Reaction of a Pyrrolidinone XVI with an iso(thio)cyanate XVII

Compounds of the formula I can be prepared by reacting pyrrolidinones XVI with an iso(thio)cyanate XVII in the presence of a base according to the synthesis route shown in Scheme 13. Such reactions are known, for example, from U.S. Pat. No. 5,185,349.

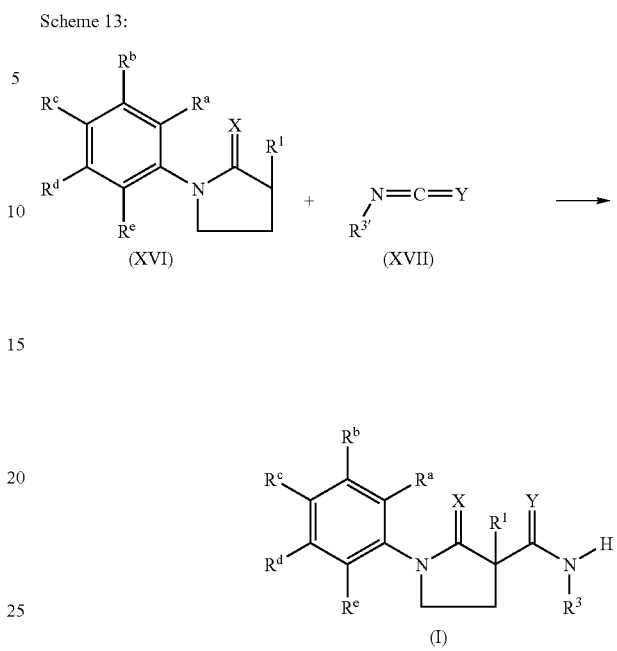

In Scheme 13, the variables $R^a$, $R^b$, $R^c$, $R^d$, $R^d$, $R^e$, X, Y and $R^1$ are as defined above. $R^{3'}$ has the meanings mentioned for $R^3$ which are different from hydrogen. To prepare compounds I where $R^3$=H, preference is given to using the salt of an isocyanate or isothiocyanate, for example sodium iso(thio)cyanate or potassium iso(thio)cyanate.

Suitable bases include alkali metal hydrides, such as sodium hydride or potassium hydride, organolithium compounds, such as lithium diisopropylamide. In general, the reaction is carried out in a solvent. Suitable solvents include ethers, such as diethyl ether, methyl tert-butyl ether, tetrahydrofuran, 1,4-dioxane, anisole, glycol ethers, such as dimethyl glycol ether, hydrocarbons, such as hexane, petroleum ether or mixtures of these.

The compounds I and their agriculturally useful salts are suitable—both as isomer mixtures and in the form of the pure isomers—as herbicides. The herbicidal compositions comprising I permit very good control of plant growth on uncultivated areas. In crops such as wheat, rice, corn, soybean and cotton, they are effective against broad-leaved weeds and harmful grasses without significantly damaging the crops. This effect occurs in particular at low application rates.

Depending on the particular application method, the compounds I or the herbicidal compositions comprising them may be used in a further number of crops for eliminating unwanted plants. Suitable are, for example, the following crops:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium*

*herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

The compounds I may also be used in crops which are tolerant to the action of herbicides as a result of breeding, including the use of genetic engineering methods.

The compounds I or the herbicidal compositions comprising them can be used, for example, in the form of directly sprayable aqueous solutions, powders, suspensions, including highly concentrated aqueous, oily or other suspensions or dispersions, emulsions, oil dispersions, pastes, dusting agents, broadcasting agents or granules, by spraying, nebulizing, dusting, broadcasting or pouring, or for seed dressing or mixing with the seed. The application forms depend on the intended uses; they should in any case ensure very fine distribution of the active ingredients according to the invention.

The herbicidal compositions comprise a herbicidally effective amount of at least one active compound of the formula I and auxiliaries which are usually used in formulating crop protection agents.

Suitable inert auxiliaries are essentially:

mineral oil fractions having a medium to high boiling point, such as kerosine and diesel oil, and coal tar oils and oils of vegetable or animal origin, aliphatic, cyclic and aromatic hydrocarbons, for example paraffins, tetrahydronaphthalene, alkylated naphthalenes and derivatives thereof, alkylated benzenes and derivatives thereof, alcohols, such as methanol, ethanol, propanol, butanol and cyclohexanol, ketones, such as cyclohexanone, and strongly polar solvents, for example amines, such as N-methylpyrrolidone, and water.

Aqueous application forms can be prepared from emulsion concentrates, from suspensions, pastes, wettable powders or water-dispersible granules by adding water. For the preparation of emulsions, pastes or oil dispersions, the 1-phenylpyrrolidin-2-onecarboxamides I, as such or dissolved in an oil or solvent, can be homogenized in water by means of wetting agents, adherents, dispersants or emulsifiers. However, it is also possible to prepare concentrates which consist of active ingredient, wetting agent, adherent, dispersant or emulsifier and possibly solvent or oil, which are suitable for dilution with water.

Suitable surfactants are the alkali metal, alkaline earth metal and ammonium salts of aromatic sulfonic acids, e.g. lignin-, phenol-, naphthalene- and dibutylnaphthalene-sulfonic acid, and of fatty acids, alkylsulfonates and alkylarylsulfonates, alkyl sulfates, lauryl ether sulfates and fatty alcohol sulfates, and salts of sulfated hexa-, hepta- and octadecanols and of fatty alcohol glycol ether; condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The concentrations of the active ingredients I in the ready-to-use formulations may be varied within wide ranges. In general, the formulations comprise from about 0.001 to 98, preferably from 0.01 to 95, % by weight of at least one active ingredient I. The active ingredients are used in a purity of from 90 to 100%, preferably from 95 to 100% (according to the NMR spectrum).

The compounds I according to the invention can be formulated, for example, as follows:

I. 20 parts by weight of a compound I are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which comprises 0.02% by weight of the active ingredient is obtained.

II. 20 parts by weight of a compound I are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which comprises 0.02% by weight of the active ingredient is obtained.

III. 20 parts by weight of a compound I are dissolved in a mixture which consists of 25 parts by weight of cyclohexanone, 65 parts by weight of a mineral oil fraction boiling within the range from 210 to 280° C. and 10 parts by weight of the adduct of 40 mol of ethylene oxide with 1 mol of castor oil. By pouring the solution into 100,000 parts by weight of water and finely distributing it therein, an aqueous dispersion which comprises 0.02% by weight of the active ingredient is obtained.

IV. 20 parts by weight of a compound I are thoroughly mixed with 3 parts by weight of the sodium salt of diisobutyl-naphthalene-α-sulfonic acid, 17 parts by weight of the sodium salt of a lignosulfonic acid obtained from a sulfite waste liquor and 60 parts by weight of silica gel powder, and the mixture is milled in a hammer mill. By finely distributing the mixture in 20,000 parts by weight of water, a spray liquor which comprises 0.1% by weight of the active ingredient is obtained.

V. 3 parts by weight of a compound I are mixed with 97 parts by weight of finely divided kaolin. A dusting agent which comprises 3% by weight of the active ingredient is obtained in this manner.

VI. 20 parts by weight of a compound I are thoroughly mixed with 2 parts by weight of the calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

VII. 1 part by weight of a compound I is dissolved in a mixture which consists of 70 parts by height of cyclohexanone, 20 parts by weight of ethoxylated isooctylphenol and 10 parts by weight of ethoxylated castor oil. A stable emulsion concentrate is obtained.

VIII. 1 part by weight of a compound I is dissolved in a mixture which consists of 80 parts by weight of cyclohexanone and 20 parts by weight of Wettol® EM31 (=nonionic emulsifier based on ethoxylated castor oil; BASF AG). A stable emulsion concentrate is obtained.

The active compounds I or the herbicidal compositions can be applied by the preemergence or postemergence method. The herbicidal compositions or active compounds can also be applied by sowing crop seed which has been pretreated with the herbicidal compositions or active compounds. If the active ingredients are less well tolerated by certain crops, it is possible to use application methods in which the herbicidal compositions are sprayed with the aid of the sprayers in such a way that the leaves of the sensitive crops are as far as possible not affected, while the active compounds reach the leaves of undesirable plants growing underneath or the uncovered soil surface (post-directed, lay-by).

The application rates of active compound I are from 0.001 to 3.0, preferably from 0.01 to 1.0, kg/ha of active ingredient (a.i.), depending on the aim of control, the season, the target plants and the state of growth.

In order to broaden the action spectrum and to achieve synergistic effects, the compounds I according to the invention may be mixed with many members of other groups of herbicidal or growth-regulating active ingredients and applied together with them.

Examples of suitable components of the mixture are 1,2,4-thiadiazoles, 1,3,4-thiadiazoles, amides, aminophosphoric acid and derivatives thereof, aminotriazoles, anilides, aryloxy-/hetaryloxyalkanoic acids and derivatives thereof, benzoic acid and derivatives thereof, benzothiadiazinones, 2-(hetaroyl/aroyl)-1,3-cyclohexanediones, hetarylarylketones, benzylisoxazolidinones, meta-CF$_3$-phenyl derivatives, carbamates, quinolinecarboxylic acid and derivatives thereof, chloroacetanilides, cyclohexane-1,3-dione derivatives, diazines, dichloropropionic acid and derivatives thereof, dihydrobenzofurans, dihydrofuran-3-ones, dinitroanilines, dinitrophenols, diphenyl ethers, dipyridyls, halocarboxylic acids and derivatives thereof, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolcarboxamides and uracils.

It may also be useful to apply the compounds I together, alone or in combination with other herbicides, also as a mixture with further crop-protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates can also be added.

The examples below are intended to illustrate the invention without limiting it.

PREPARATION EXAMPLES

The products were characterized by HPLC/MS (high performance liquid chromatography/mass spectrometry), by $^1$H-NMR spectroscopy or by their melting point.

HPLC column: RP-18 column (Chromolith Speed ROD from Merck KgaA, Germany).

Mobile phase: acetonitrile +0.1% trifluoroacetic acid (TFA)/water +0.1% TFA in a gradient from 5:95 to 95:5 over 5 minutes, at 40° C.

MS: quadrupole electrospray ionization, 80 V (positive mode)

Example 1

1-(3-trifluoromethyl)phenyl-3-(N-methyl)carboxamido-2-pyrrolidinone

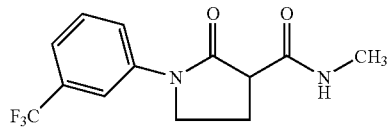

1.1: 1-(3-trifluoromethyl)phenyl-2-pyrrolidinone 54 g (0.34 mol) of 3-trifluoromethylaniline, 110 ml of butyrolactone and 5 ml of concentrated hydrochloric acid were heated at reflux for 13 hours. Excess butyrolactone was then removed under reduced pressure. The resulting crystalline residue was washed initially with an aqueous sodium bicarbonate solution and then with water and subsequently with pentane. Drying gave 65.5 g (85% of theory) of 1-(3-trifluoromethyl)phenyl-2-pyrrolidinone.

$^1$H-NMR (270 MHz, CDCl$_3$) δ (ppm): 7.85 (m, 2H), 7.45 (t, 1H), 7.4 (d, 1H), 3.85 (t, 2H), 2.6 (t, 2H), 2.2 (qu, 2H).

1.2: 2-oxo-1-(3-trifluoromethyl)phenyl-3-pyrrolidinecarboxylic acid

Under nitrogen, 50 ml of absolute tetrahydrofuran were added to 13.6 g (0.06 mol) of 1-(3-trifluoromethyl)phenyl-2-pyrrolidinone from 1.1, the mixture was cooled to 0° C. and 60 ml of 2M (0.12 mol) lithium diisoproylamide in a solvent mixture of heptane, tetrahydrofuran and ethylbenzene were added. The reaction mixture was stirred at 0° C. for 45 minutes. 5.4 g (0.06 mol) of dimethyl carbonate in 10 ml of absolute tetrahydrofuran were then added. After the addition had ended, the reaction mixture was allowed to warm to 20° C. and stirred for another 72 hours. The solvent was evaporated under reduced pressure and methyl tert-butyl ether and water were then added to the resulting residue, the phases were separated and the organic phase was extracted twice with water. The aqueous phase was acidified with hydrochloric acid (10% by weight) to pH=1. The mixture was extracted twice with in each case 100 ml of ethyl acetate and the combined organic phase was dried and concentrated under reduced pressure. This gave 5.61 g (34% of theory) of 2-oxo-1-(3-trifluoromethyl)phenyl-3-pyrrolidinecarboxylic acid of melting point 121° C.

$^1$H-NMR (400 MHz, CDCl$_3$) δ (ppm): 7.9 (s, 1H), 7.8 (d, 1H), 7.5 (t, 1H), 7.45 (d, 1H), 4.1-3.9 (m, 2H), 3.7 (t, 1H), 2.55 (m, 2H).

1.3: 1-(3-trifluoromethyl)phenyl-3-(N-methyl)carboxamido-2-pyrrolidinone 0.14 g (1.8 mmol) of a 40% strength aqueous methylamine solution was added to 0.5 g (1.8 mmol) of 2-oxo-1-(3-trifluoromethyl) phenyl-3-pyrrolidinecarboxylic acid from 1.2 in 50 ml of dichloromethane and 0.35 g (2 mmol) of 1,1'-carbonyldiimidazole. The reaction mixture was stirred at room temperature for 18 hours. The reaction mixture was extracted with saturated aqueous ammonium chloride solution and the organic phase was then extracted with water. The organic phase was dried over anhydrous sodium sulfate, the solvent was removed under reduced pressure and the residue that remained was then titrated with methyl tert-butyl ether. The insoluble fraction was then separated off, and the residue was washed with methyl tert-butyl ether. This gave 0.166 g (32% of theory) of the title compound of melting point 128° C.

$^1$H-NMR (400 MHz, CDCl$_3$) δ (ppm): 7.9 (s, 1H), 7.75 (d, 1H), 7.5 (t, 1H), 7.4 (d, 1H), 7.3-7.2 (br, 1H), 4.0-3.8 (m, 2H), 3.5 (t, 1H), 2.9 (d, 3H), 2.75-2.6 (m, 1H), 2.55-2.45 (m, 1H).

Example 2

1-(3-trifluoromethoxy)phenyl-3-acetyloxy-3-(N-phenyl)carboxamido-2-pyrrolidinone

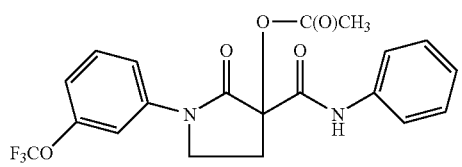

0.34 g (0.93 mmol) of 1-(3-trifluoromethoxy)phenyl-3-(N-phenyl)-carboxamido-2-pyrrolidinone, prepared analogously to Example 1 using the starting material 3-trifluoromethoxyaniline, was initially charged in 3 ml of dry dimethylformamide (DMF), and 0.04 g (0.093 mmol) of sodium hydride (60% in mineral oil) was added at 20° C. The mixture was then stirred at 20° C. for 30 min, 0.07 g (0.093 mmol) of acetyl chloride was then added and the mixture was stirred at 20° C. for another 18 h. Water was added and the mixture was extracted repeatedly with dichloromethane. The combined organic phases were washed with water, the solvent was removed and the residue was chromatographed. This gave 0.27 g of the title compound of melting point 140° C.

The compounds of Examples 3 to 191 were prepared in an analogous manner:

TABLE 2

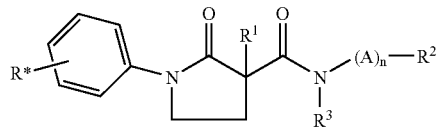

| Example | (A)$_n$ | R* | R$^1$ | R$^2$ | R$^3$ | m.p. [° C.] or RT (HPLC/MS) |
|---|---|---|---|---|---|---|
| 1 | — | 3-CF$_3$ | H | methyl | H | 128 |
| 2 | — | 3-OCF$_3$ | OC(O)CH$_3$ | phenyl | H | 140 |
| 3 | — | 3-CF$_3$ | H | ethyl | H | 122 |
| 4 | — | 3-CF$_3$ | H | n-propyl | H | 112 |
| 5 | — | 3-CF$_3$ | H | n-butyl | H | 111 |
| 6 | — | 3-CF$_3$ | H | tert-butyl | H | oil |
| 7 | — | 3-CF$_3$ | H | cyclopentyl | H | oil |
| 8 | — | 3-CF$_3$ | H | ethyl | ethyl | oil |
| 9 | — | 3-CF$_3$ | H | methyl | n-butyl | oil |
| 10 | — | 3-CF$_3$ | H | phenyl | H | oil |
| 11 | — | 3-CF$_3$ | H | CH(CH$_3$)$_2$ | H | 136 |
| 12 | — | 3-CF$_3$ | H | cyclohexyl | H | 141 |
| 13 | — | 3-CF$_3$ | H | CH$_2$-cyclopropyl | H | 108 |
| 14 | — | 3-CF$_3$ | H | cyclopropyl | H | oil |
| 15 | — | 3-CF$_3$ | H | methyl | methyl | oil |
| 16 | — | 3-CF$_3$ | H | cyclopropyl | methyl | oil |
| 17 | O | 3-CF$_3$ | H | t-butyl | H | 122 |
| 18 | — | 3-OCF$_3$ | H | methyl | H | 103 |
| 19 | — | 3-OCF$_3$ | H | ethyl | H | 111 |
| 20 | — | 3-OCF$_3$ | H | n-propyl | H | 110 |
| 21 | — | 3-OCF$_3$ | H | tert-butyl | H | 89 |
| 22 | — | 3-OCF$_3$ | H | cyclopentyl | H | 140 |
| 23 | — | 3-OCF$_3$ | H | methyl | n-butyl | oil |
| 24 | — | 3-OCF$_3$ | H | phenyl | H | 108 |
| 25 | — | 3-OCF$_3$ | H | CH(CH$_3$)$_2$ | H | 134 |
| 26 | — | 3-OCF$_3$ | H | cyclopropyl | H | 134 |

TABLE 2-continued

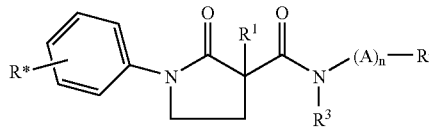

| Example | (A)$_n$ | R* | R$^1$ | R$^2$ | R$^3$ | m.p. [° C.] or RT (HPLC/MS) |
|---|---|---|---|---|---|---|
| 27 | — | 3-OCF$_3$ | H | methyl | methyl | oil |
| 28 | — | 3-OCF$_3$ | H | H | H | 106 |
| 29 | O | 3-OCF$_3$ | H | H | H | 124 |
| 30 | — | 3-OCF$_3$ | OC(O)CH$_3$ | cyclopentyl | H | oil |
| 31 | O | 3-OCF$_3$ | H | methyl | H | 98 |
| 32 | — | 3-OCF$_3$ | CH$_3$ | tert-butyl | H | 40 |
| 33 | O | 3-OCF$_3$ | H | CH$_2$-phenyl | H | 108 |
| 34 | O | 3-OCF$_3$ | H | methyl | methyl | oil |
| 35 | O | 3-OCF$_3$ | H | CH(CH$_3$)$_2$ | H | 123 |
| 36 | O | 3-OCF$_3$ | H | CH$_2$CH=CH$_2$ | H | 75 |
| 37 | O | 3-OCF$_3$ | H | CH$_2$C(Cl)=CH$_2$ | H | 68 |
| 38 | O | 3-OCF$_3$ | H | CH$_2$CH$_2$CH$_3$ | | 29 |
| 39 | O | 3-OCF$_3$ | H | CH$_2$CH=CHCH$_3$ | H | 87 |
| 40 | O | 3-OCF$_3$ | H | CH$_2$CH=CHCl | H | 62 |
| 41 | O | 3-OCF$_3$ | H | CH$_2$CH$_3$ | H | 100 |
| 42 | O | 3-OCF$_3$ | H | CH$_2$CH$_2$OCH$_3$ | H | 85 |
| 43 | O | 3-OCF$_3$ | H | cylohexyl | H | 152 |
| 44 | O | 3-OCF$_3$ | H | CH$_2$-cylohexyl | H | 135 |
| 45 | — | 3-CH(CH$_3$)$_2$ | H | tert-butyl | H | 51 |
| 46 | — | 3-CH(CH$_3$)$_2$ | CH$_3$ | tert-butyl | H | 78 |
| 47 | O | 3-CF$_3$ | H | tert-butyl | H | oil |
| 48 | O | 3-OCF$_3$ | H | tert-butyl | H | 112 |
| 49 | — | 2-Cl | H | tert-butyl | H | 76 |
| 50 | — | 3-Cl | H | tert-butyl | H | 118 |
| 51 | — | 3-Cl; 5-Cl | H | tert-butyl | H | 130 |
| 52 | — | 2-Cl; 4-Cl | H | tert-butyl | H | 93 |
| 53 | — | 2-F | H | tert-butyl | H | 113 |
| 54 | — | 2-CF$_3$ | H | tert-butyl | H | 90 |
| 55 | — | 4-CF$_3$ | H | tert-butyl | H | 155 |
| 56 | — | 2-CH$_3$ | H | tert-butyl | H | 93 |
| 57 | — | 3-CH$_3$ | H | tert-butyl | H | 88 |
| 58 | — | 4-CH$_3$ | H | tert-butyl | H | 135 |
| 59 | — | 2-CH(CH$_3$)$_2$ | H | tert-butyl | H | 104 |
| 60 | — | 3-OCH$_3$ | H | tert-butyl | H | 43 |
| 61 | — | 4-OCH$_3$ | H | tert-butyl | H | 132 |
| 62 | — | 2-OCH$_3$ | H | tert-butyl | H | oil |
| 63 | — | 2-Cl; 6-Cl | H | tert-butyl | H | oil |
| 64 | — | 2-Cl; 3-Cl | H | tert-butyl | H | oil |
| 65 | — | 4-Cl | H | tert-butyl | H | 155 |
| 66 | — | 3-OCH$_3$ | H | ![structure] | H | 110-112 |
| 67 | — | 3-OCF$_3$ | H | ![structure] | H | 3.78 min, m/z = 405 [M + H]$^+$ |
| 68 | — | 3-OCF$_3$ | H | ![structure] | H | 4.09 min, m/z = 399 [M + H]$^+$ |
| 69 | — | 3-OCF$_3$ | H | ![structure] | H | 3.62 min, m/z = 391 [M + H]$^+$ |
| 70 | — | 3-OCF$_3$ | H | ![structure] | H | 3.89 min, m/z = 397 [M + H]$^+$ |

TABLE 2-continued

| Example | (A)ₙ | R* | R¹ | R² | R³ | m.p. [° C.] or RT (HPLC/MS) |
|---|---|---|---|---|---|---|
| 71 | — | 3-OCF₃ | H | 2-chlorophenyl-CH₂CH₂-C(CH₃)₂- | H | 4.30 min, m/z = 469 [M + H]⁺ |
| 72 | — | 3-OCF₃ | H | 3-chlorophenyl-CH₂CH₂-C(CH₃)₂- | H | 4.03 min, m/z = 469 [M + H]⁺ |
| 73 | — | 3-OCF₃ | H | 4-methylphenyl-C(CH₃)₂- | H | 3.95 min, m/z = 443 [M + Na]⁺ |
| 74 | — | 3-OCF₃ | H | 3-methylphenyl-C(CH₃)₂- | H | 3.93 min, m/z = 443 [M + Na]⁺ |
| 75 | — | 3-OCF₃ | H | 3,4-dimethoxybenzyl-C(CH₃)(CO₂Me)- | H | 3.61 min, m/z = 525 [M + H]⁺ |
| 76 | — | 3-OCF₃ | H | 3-methoxyphenyl-C(CH₃)₂- | H | 3.75 min, m/z = 459 [M + Na]⁺ |
| 77 | — | 3-OCF₃ | H | 3,4-dimethoxyphenyl-C(CH₃)₂- | H | 3.55 min, m/z = 489 [M + Na]⁺ |
| 78 | — | 3-OCF₃ | H | 3-ethylpentan-3-yl | H | 3.84 min, m/z = 373 [M + H]⁺ |
| 79 | — | 3-OCF₃ | H | 3,4-dichlorophenyl-C(CH₃)₂- | H | 4.11 min, m/z = 498 [M + Na]⁺ |

TABLE 2-continued
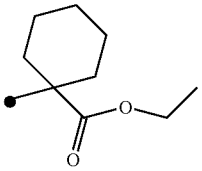
| Example | (A)$_n$ | R* | R$^1$ | R$^2$ | R$^3$ | m.p. [° C.] or RT (HPLC/MS) |
|---|---|---|---|---|---|---|
| 80 | — | 3-OCF$_3$ | H |  | H | 3.79 min, m/z = 443 [M + H]$^+$ |
| 81 | — | 3-OCF$_3$ | H |  | H | 3.88 min, m/z = 373 [M + H]$^+$ |
| 82 | — | 3-OCF$_3$ | H | 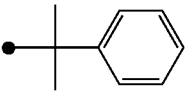 | H | 3.60 min, m/z = 387 [M + H]$^+$ |
| 83 | — | 3-OCF$_3$ | H | 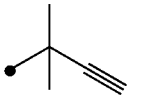 | H | 3.80 min, m/z = 429 [M + Na]$^+$ |
| 84 | — | 3-OCF$_3$ | H | 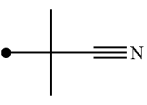 | H | 3.37 min, m/z = 355 [M + H]$^+$ |
| 85 | — | 3-OCF$_3$ | H | 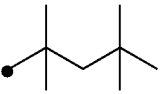 | H | 3.17 min, m/z = 356 [M + H]$^+$ |
| 86 | — | 3-OCF$_3$ | H | 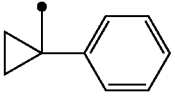 | H | 4.20 min, m/z = 401 [M + H]$^+$ |
| 87 | — | 3-OCF$_3$ | H | 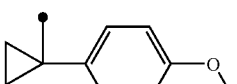 | H | 3.33 min, m/z = 405 [M + H]$^+$ |
| 88 | — | 3-OCF$_3$ | H | 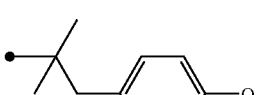 | H | 3.52 min, m/z = 435 [M + H]$^+$ |
| 89 | — | 3-OCF$_3$ | H | 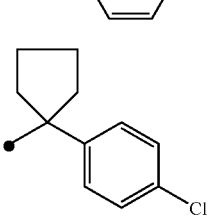 | H | 3.91 min, m/z = 451 [M + H]$^+$ |
| 90 | — | 3-OCF$_3$ | H |  | H | 4.20 min, m/z = 491 [M + Na]$^+$ |

TABLE 2-continued
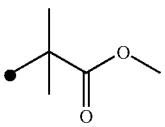
| Example | (A)ₙ | R* | R¹ | R² | R³ | m.p. [° C.] or RT (HPLC/MS) |
|---|---|---|---|---|---|---|
| 91 | — | 3-OCF₃ | H | 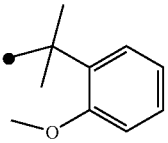 | H | 3.18 min, m/z = 389 [M + H]⁺ |
| 92 | — | 3-OCF₃ | H | 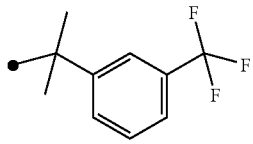 | H | 3.85 min, m/z = 460 [M + Na]⁺ |
| 93 | — | 3-OCF₃ | H | 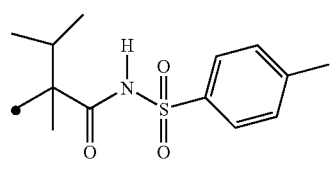 | H | 4.03 min, m/z = 475 [M + H]⁺ |
| 94 | — | 3-OCF₃ | H | 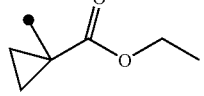 | H | 3.82 min, m/z = 579 [M + Na]⁺ |
| 95 | — | 3-OCF₃ | H | 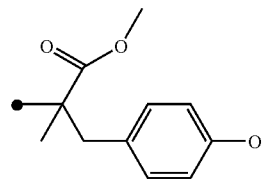 | H | 3.19 min, m/z = 401 [M + H]⁺ |
| 96 | — | 3-OCF₃ | H | 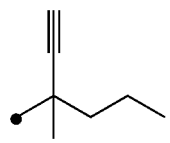 | H | 3.32 min, m/z = 481 [M + H]⁺ |
| 97 | — | 3-OCF₃ | H | 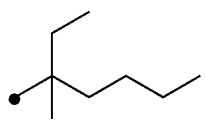 | H | 3.75 min, m/z = 383 [M + H]⁺ |
| 98 | — | 3-OCF₃ | H |  | H | 4.26 min, m/z = 401 [M + H]⁺ |

TABLE 2-continued

| Example | (A)ₙ | R* | R¹ | R² | R³ | m.p. [° C.] or RT (HPLC/MS) |
|---|---|---|---|---|---|---|
| 99 | — | 3-OCF₃ | H | (structure) | H | 4.06 min, m/z = 411 [M + H]⁺ |
| 100 | — | 3-OCF₃ | H | (structure) | H | 3.54 min, m/z = 415 [M + H]⁺ |
| 101 | — | 3-OCF₃ | H | (structure) | H | 3.79 min, m/z = 429 [M + H]⁺ |
| 102 | — | 3-OCF₃ | H | (structure) | H | 3.77 min, m/z = 429 [M + H]⁺ |
| 103 | — | 3-OCF₃ | H | (structure) | H | 4.09 min, m/z = 435 [M + H]⁺ |
| 104 | — | 3-OCF₃ | H | (structure) | H | 3.98 min, m/z = 439 [M + H]⁺ |
| 105 | — | 3-OCF₃ | H | (structure) | H | 3.75 min, m/z = 383 [M + H]⁺ |
| 106 | — | 3-OCF₃ | H | (structure) | H | 2.93 min, m/z = 421 [M + H]⁺ |
| 107 | — | 3-OCF₃ | H | (structure) | H | 3.63 min, m/z = 504 [M + H]⁺ |
| 108 | — | 3-OCHF₂ | H | phenyl | H | 104 |

TABLE 2-continued
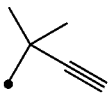
| Example | (A)$_n$ | R* | R$^1$ | R$^2$ | R$^3$ | m.p. [° C.] or RT (HPLC/MS) |
|---|---|---|---|---|---|---|
| 109 | — | 3-OCHF$_2$ | H | 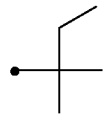 | H | 80 |
| 110 | — | 3-OCHF$_2$ | H | tert-butyl | H | 64 |
| 111 | — | 3-OCHF$_2$ | H | 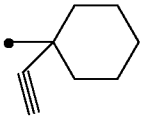 | H | oil |
| 112 | — | 3-OCHF$_2$ | H | 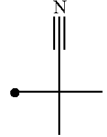 | H | 153 |
| 113 | — | 3-OCHF$_2$ | H | 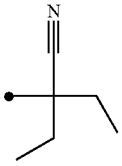 | H | oil |
| 114 | — | 3-OCHF$_2$ | H | 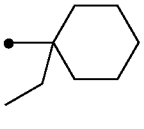 | H | oil |
| 115 | — | 3-OCHF$_2$ | H | 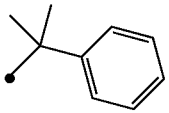 | H | 48 |
| 116 | — | 3-OCHF$_2$ | H | 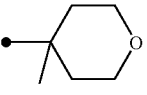 | H | oil |
| 117 | — | 3-OCHF$_2$ | H | 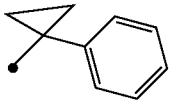 | H | 82 |
| 118 | — | 3-OCHF$_2$ | H |  | H | oil |
| 119 | — | 3-OCHF$_2$ | H | CH$_3$ | H | 74 |
| 120 | — | 3-OCHF$_2$ | H | ethyl | H | 70 |
| 121 | — | 3-OCHF$_2$ | H | isopropyl | H | 126 |
| 122 | — | 3-OCHF$_2$ | H | cylopropyl | H | 130 |
| 123 | — | 4-CH=C(Cl)$_2$ | H | tert-butyl | H | 166-167 |
| 124 | — | 3-CF$_3$; 5-CF$_3$ | H | tert-butyl | H | 135-136 |

TABLE 2-continued

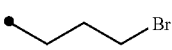

| Example | (A)ₙ | R* | R¹ | R² | R³ | m.p. [° C.] or RT (HPLC/MS) |
|---|---|---|---|---|---|---|
| 125 | — | 4-SCH₃ | H | tert-butyl | H | 166-167 |
| 126 | — | 4-CH(CH₃)₂ | H | tert-butyl | H | 130-131 |
| 127 | — | 4-OCHF₂ | H | tert-butyl | H | 152-153 |
| 128 | — | 3-Cl; 4-Cl; 5-Cl | H | tert-butyl | H | 160-163 |
| 129 | — | 3-Br; 5-Br | H | tert-butyl | H | 140-141 |
| 130 | — | 4-NO₂; 5-Cl | H | tert-butyl | H | 152-153 |
| 131 | — | 4-OCF₂CF₃ | H | tert-butyl | H | 66-67 |
| 132 | — | 3-OCF₃ | H | 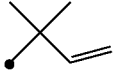 | H | oil |
| 133 | — | 3-OCF₃ | H |  | H | 3.51 min, m/z = 357 [M + H]⁺ |
| 134 | — | 3-OCF₃ | H | 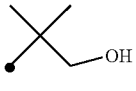 | H | 3.67 min, m/z = 359 [M + H]⁺ |
| 135 | — | 3-OCF₃ | H | 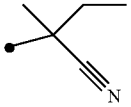 | H | 2.92 min, m/z = 361 [M + H]⁺ |
| 136 | — | 3-OCF₃ | H | 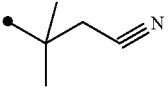 | H | 3.31 min, m/z = 370 [M + H]⁺ |
| 137 | — | 3-OCF₃ | H |  | H | 3.23 min, m/z = 370 [M + H]⁺ |
| 138 | — | 3-CF₃; 4-Cl | H | tert-butyl | H | 3.65 min m/z = 363 [M + H]⁺ |
| 139 | — | 3-OCH₃; 5-OCH₃ | H | tert-butyl | H | 2.87 min m/z = 321 [M + H]⁺ |
| 140 | — | 3-SCH₃ | H | tert-butyl | H | 3.14 min m/z = 307 [M + H]⁺ |
| 141 | — | 3-tert-butyl | H | tert-butyl | H | 3.62 min m/z = 317 [M + H]⁺ |
| 142 | — | O—CH(CH₃)₂ | H | tert-butyl | H | 3.24 min m/z = 319 [M + H]⁺ |
| 143 | — | 3-F; 4-F | H | tert-butyl | H | 3.07 min m/z = 297 [M + H]⁺ |
| 144 | — | 3-OCH₃; 4-OCH₃; 5-OCH₃ | H | tert-butyl | H | 2.64 min m/z = 351 [M + H]⁺ |
| 145 | — | 4-propyl | H | tert-butyl | H | 3.53 min m/z = 303 [M + H]⁺ |
| 146 | — | 4-O-tert-butyl | H | tert-butyl | H | 3.36 min m/z = 333 [M + H]⁺ |

TABLE 2-continued

| Example | (A)ₙ | R* | R¹ | R² | R³ | m.p. [° C.] or RT (HPLC/MS) |
|---|---|---|---|---|---|---|
| 147 | — | 3-Cl; 4-F | H | tert-butyl | H | 3.26 min m/z = 313 [M + H]⁺ |
| 148 | — | 4-O-propyl | H | tert-butyl | H | 3.67 min m/z = 319 [M + H]⁺ |
| 149 | — | 4-Br | H | tert-butyl | H | 3.19 min m/z = 339 [M + H]⁺ |
| 150 | — | 4-SCH₂CH₃ | H | tert-butyl | H | 3.32 min m/z = 321 [M + H]⁺ |
| 151 | — | 3-Br; 4-OCH₃; 5-Cl | H | tert-butyl | H | 3.49 min m/z = 405 [M + H]⁺ |
| 152 | — | 3-Cl; 4-O-propyl | H | tert-butyl | H | 3.58 min m/z = 353 [M + H]⁺ |
| 153 | — | 3-F; 4-NO₂ | H | tert-butyl | H | 2.97 min m/z = 324 [M + H]⁺ |
| 154 | — | 3-Br; 5-Br; 4-Cl | H | tert-butyl | H | 3.86 min m/z = 452 [M + H]⁺ |
| 155 | — | 3-ethyl; 5-CH₃ | H | tert-butyl | H | 3.47 min m/z = 303 [M]⁺ |
| 156 | — | 3-CH₂; 5-CH₃ | H | tert-butyl | H | 3.22 min m/z = 289 [M + H]⁺ |
| 157 | — | 3-Br | H | tert-butyl | H | 3.21 min m/z = 341 [M + H]⁺ |
| 158 | — | 3-ethyl | H | tert-butyl | H | 3.23 min m/z = 289 [M + H]⁺ |
| 159 | — | 3-iso-propyl; 4-OCH₃ | H | tert-butyl | H | 3.46 min m/z = 333 [M + H]⁺ |
| 160 | — | 3,4-OCH₂CH₂O— | H | tert-butyl | H | 2.66 min m/z = 319 [M + H]⁺ |
| 161 | — | 4-CN | H | tert-butyl | H | 2.74 min m/z = 286 [M + H]⁺ |
| 162 | — | 3-CN; 4-OCH₃ | H | tert-butyl | H | 2.74 min m/z = 316 [M + H]⁺ |
| 163 | — | 3-CN; 4-F | H | tert-butyl | H | 2.79 min m/z = 304 [M + H]⁺ |
| 164 | — | 3-F; 4-CH₃ | H | tert-butyl | H | 3.22 min m/z = 293 [M + H]⁺ |
| 165 | — | 3-CN; 4-Cl | H | tert-butyl | H | 3.09 min m/z = 320 [M + H]⁺ |
| 166 | — | 3-Cl; 4-Cl | H | tert-butyl | H | 3.53 min m/z = 329 [M]⁺ |
| 167 | — | 3-CH₃; 4-F | H | tert-butyl | H | 3.11 min m/z = 293 [M + H]⁺ |
| 168 | — | 3-Cl; 4-OCH₃ | H | tert-butyl | H | 3.06 min m/z = 325 [M + H]⁺ |

TABLE 2-continued

| Example | (A)n | R* | R¹ | R² | R³ | m.p. [° C.] or RT (HPLC/MS) |
|---|---|---|---|---|---|---|
| 169 | — | 4-heptyl | H | tert-butyl | H | 4.50 min m/z = 359 [M + H]⁺ |
| 170 | — | 4-tert-butyl | H | tert-butyl | H | 3.73 min m/z = 317 [M + H]⁺ |
| 171 | — | 4-ethyl | H | tert-butyl | H | 3.32 min m/z = 289 [M + H]⁺ |
| 172 | — | 3-Cl; 4-iso-propyl | H | tert-butyl | H | 3.82 min m/z = 337 [M + H]⁺ |
| 173 | — | 3-Cl; 4-CH₃ | H | tert-butyl | H | 3.45 min m/z = 309 [M]⁺ |
| 174 | — | 3-F | H | tert-butyl | H | 3.96 min m/z = 279 [M + H]⁺ |
| 175 | — | 3-CH₃; 5-propyl | H | tert-butyl | H | 94-96 |
| 176 | — | 3-ethyl; 5-ethyl | H | tert-butyl | H | 120-122 |
| 177 | — | 3-O-ethyl | H | tert-butyl | H | 86-88 |
| 178 | — | 3-OCH₃; 4-Br | H | tert-butyl | H | 150-152 |
| 179 | — | 3-OCH₃; 4-Cl | H | tert-butyl | H | 137-139 |
| 180 | — | 3-Cl; 4-SCF₃ | H | tert-butyl | H | 3.86 min m/z = 395 [M + H]⁺ |
| 181 | — | 4-F | H | tert-butyl | H | 2.77 min m/z = 278 [M + H]⁺ |
| 182 | — | 3-OCF₃ | H | 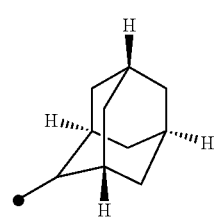 | H | 4.16 min m/z = 423 [M + H]⁺ |
| 183 | — | 3-OCF₃ | H | 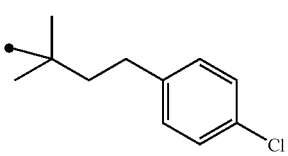 | H | 4.31 min m/z = 469 [M + H]⁺ |
| 184 | — | 3-OCF₃ | H | 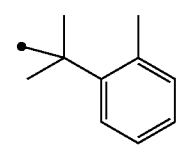 | H | 3.87 min m/z = 443 [M + H]⁺ |
| 185 | — | 3-OCF₃ | H | 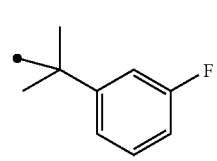 | H | 3.76 min m/z = 447 [M + Na]⁺ |

TABLE 2-continued

| Example | (A)ₙ | R* | R¹ | R² | R³ | m.p. [° C.] or RT (HPLC/MS) |
|---|---|---|---|---|---|---|
| 186 | — | 3-OCF₃ | H | (2,3-dimethyl-butanamide group) | H | 3.00 min m/z = 402 [M + H]⁺ |
| 187 | — | 3-OCF₃ | H | (tert-butyl 2,2-dimethylpropanoate group) | H | 3.75 min m/z = 453 [M + Na]⁺ |
| 188 | — | 3-OCF₃ | H | (2-(3-chlorophenyl)propan-2-yl group) | H | 3.94 min m/z = 463 [M + Na]⁺ |
| 189 | — | 3-OCF₃ | H | (trityl group) | H | 4.42 min m/z = 553 [M + Na]⁺ |
| 190 | — | 3-OCF₃ | H | (2,3,3-trimethylbutyl group) | H | 3.85 min m/z = 473 [M + Na]⁺ |
| 191 | — | 3-OCF₃ | H | (bis(2-ethylhexyl) hexahydropyrimidine group) | H | 4.49 min m/z = 611 [M + Na]⁺ |

*The number in front of the substituent denotes the position of the substituent on the phenyl ring.
● Attachment site
RT = retention time, HPLC/MS
m.p. = melting point
phenyl = C₆H₅

Example 192

1-(3-trifluoromethoxy)phenyl-3-(N-(1,1-dimethylethyl))carboxamido-2-pyrrolidinethione and 1-(3-trifluoromethoxy)phenyl-3-(N-(1,1-dimethylethyl))thiocarboxamido-2-pyrrolidinone

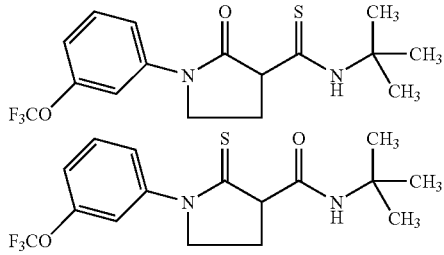

0.26 g (0.7 mmol) of 1-(3-trifluoromethoxy)phenyl-3-(N-(1,1-di-methylethyl))carboxamido-2-pyrrolidinone was initially charged in 3 ml of dry toluene, and 0.17 g (0.42 mmol) of 2,4-bis(4-methoxy-phenyl)-1,3-dithia-2,4-diphosphetane-2,4-dithione (Lawesson's reagent) was added at 20° C., and the mixture was heated at 70° C. for 7 h. The reaction mixture was then washed twice with water. The solvent was removed and the residue was chromatographed on silica gel using a mixture of cyclohexane/ethyl acetate as mobile phase. A first fraction gave 0.06 g (22%) of 1-(3-trifluoromethoxy)phenyl-3-(N-(1,1-dimethyl-ethyl))thiocarboxamido-2-pyrrolidinone of melting point 65° C. and 0.08 g (29%) of 1-(3-trifluoromethoxy)phenyl-3-(N-(1,1-dimethylethyl))carboxamido-2-pyrrolidinethione of melting point 116° C.

Use Examples

The herbicidal activity of the 1-phenylpyrrolidon-2-one-3-carboxamides of the formula I was demonstrated by the following greenhouse experiments:

The cultivation containers used were plastic flowerpots containing loamy sand with approximately 3.0% of humus as the substrate. The seeds of the test plants were sown separately for each species.

For the preemergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted. This cover causes uniform germination of the test plants, unless this was adversely affected by the active compounds.

For the postemergence treatment, the test plants were first grown to a height of 3-15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to the treatment. The application rate for the pre- and postemergence treatment was 3.0 kg of a.i./ha.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Bayer code | Common name |
| --- | --- |
| ABUTH | Velvetleaf |
| AVEFA | wild Oat |
| LOLMU | italien Ryegrass |
| SETIT | Millet |
| SINAL | velvetleaf |

At application rates of 3 kg/ha, the compound from Example 3, applied by the post-emergence method, shows very good herbicidal activity against AVEFA and SINAL.

At application rates of 3 kg/ha, the compound from Example 18, applied by the post-emergence method, shows very good herbicidal activity against ABUTH, SETIT and SINAL.

At application rates of 3 kg/ha, the compound from Example 18, applied by the pre-emergence method, shows very good herbicidal activity against ABUTH, SETIT and SINAL.

At application rates of 3 kg/ha, the compound from Example 19, applied by the pre-emergence method, shows very good herbicidal activity against ABUTH and SINAL.

At application rates of 3 kg/ha, the compound from Example 26, applied by the post-emergence method, shows very good herbicidal activity against AVEFA and SINAL.

At application rates of 3 kg/ha, the compound from Example 26, applied by the pre-emergence method, shows very good herbicidal activity against ABUTH, LOLMU and SINAL.

We claim:

1. A compound which is a 1-phenylpyrrolidin-2-one-3-carboxamide of the formula I

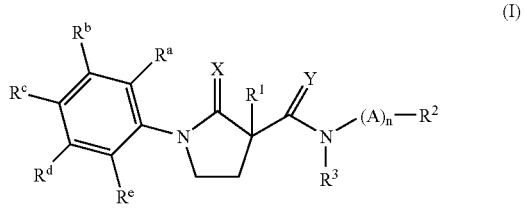

where the variables $R^1$, $R^2$, $R^3$, X, Y, A, n, $R^a$, $R^b$, $R^c$, $R^d$ and $R^e$ are as defined below:

$R^1$ is hydrogen, OH, Cl, Br, $C_1$-$C_6$-alkyl, $C_3$-$C_6$-cycloalkyl, $C_3$-$C_6$-alkenyl, $C_3$-$C_6$-alkynyl, $C(O)R^4$ or $OC(O)R^4$;

$R^2$ is $C_1$-$C_{10}$-alkyl, $C_3$-$C_8$-cycloalkyl, $C_3$-$C_8$-alkenyl, $C_3$-$C_8$-alkynyl, $C_5$-$C_8$-cycloalkenyl or $C_3$-$C_8$-cycloalkyl-$C_1$-$C_4$-alkyl, wherein $C_1$-$C_{10}$-alkyl and $C_3$-$C_8$-cycloalkyl may be partially or fully halogenated and/or may carry one or two radicals selected from the group consisting of $C_1$-$C_6$-alkoxy, $C_1$-$C_4$-haloalkoxy, $C_1$-$C_6$-alkylthio, $C_1$-$C_4$-haloalkylthio, unsubstituted or substituted phenyl group, $COOR^5$, $NR^6R^7$ and $C(O)NR^8R^9$, and wherein said phenyl group may be unsubstituted or substituted by 1, 2 or 3 substituents selected from the group consisting of halogen, nitro, OH, CN, $C_1$-$C_6$-alkyl, $C_1$-$C_6$-alkoxy, $C_1$-$C_4$-haloalkoxy, $C_1$-$C_6$- alkylthio, $C_1$-$C_4$-haloalkylthio, unsubstituted or substituted phenyl, $COOR^5$, $NR^6R^7$ and $C(O)NR^8R^9$; is hydrogen, $C_1$-$C_{10}$-alkyl, $C_3$-$C_{10}$-cycloalkyl, $C_{07}$-$C_{10}$-polycycloalkyl, $C_3$-$C_8$-alkenyl, $C_3$-$C_{10}$-alkynyl, $C_5$-$C_{10}$-cycloalkenyl, $C_3$-$C_8$-cycloalkyl-$C_1$-$C_4$-alkyl, phenyl or 3- to 7-membered heterocyclyl, where the 9 last-mentioned groups may be unsubstituted, partially or fully halogenated and/or substituted by 1, 2 or 3 radicals selected from the group consisting of OH, CN, $NO_2$, COOH, $C_1$-$C_6$-alkyl, $C_1$-$C_6$-haloalkyl, $C_1$-$C_6$-alkoxy, $C_1$-$C_4$-haloalkoxy, $C_2$-$C_6$-alkenyl, $C_2$-$C_6$-alkynyl, $C_1$-$C_6$-alkylthio, $C_1$-$C_4$-haloalkylthio, unsubstituted or substituted phenyl, $COOR^5$, $NR^6R^7$, $C(O)NR^8SO2R^{13}$, $C(O)NR^8R^9$ and 3- to 7-membered heterocyclyl, wherein each heterocyclyl may contain 1, 2 or 3 heteroatoms selected from the group consisting of oxygen, nitrogen, sulfur, a group $NR^{10}$ and a group $SO_2$, and, if appropriate, 1, 2 or 3 carbonyl groups and/or thiocarbonyl groups as ring members; and/or may contain a ring-fused phenyl ring which is unsubstituted or substituted; or $R^2$ and $R^3$, together with the group N-(A)n to which they are attached, form a saturated 3-to 7-membered heterocycle which, in addition to the nitrogen atom, may contain 1, 2 or a further 3 heteroatoms selected from the group consisting of oxygen, nitrogen, sulfur and a group $NR^{10}$ and, if appropriate, 1, 2 or 3 carbonyl groups and/or thiocarbonyl groups as ring members;

$R^a$, $R^b$, $R^c$, $R^d$ and $R^e$ independently of one another are hydrogen, OH, CN, $NO_2$, halogen, $C_1$-$C_{10}$-alkyl, $C_3$-$C_6$-cycloalkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-alkoxy, $C_1$-$C_4$-haloalkoxy, $C_1$-$C_6$-alkylthio, $C_1$-$C_4$-haloalkylthio, $C(O)R^4$, $COOR^5$, $NR^6R^7$, $C(O)NR^8R^9$, $S(O)_2NR^8R^9$, $S(O)R^{11}$, $S(O)_2R^{11}$ or $C_1$-$C_4$-alkoxy-$C_1$-$C_6$-alkyl; or two adjacent radicals $R^a$ to $R^e$, together with the atoms to which they are attached, form a 5-, 6- or 7-membered saturated or unsaturated ring which may contain one or two heteroatoms selected from the group consisting of nitrogen, oxygen, sulfur and a group $NR^{10}$ as ring-forming atom and/or may carry one, two, three or four radicals selected from the group consisting of halogen and $C_1$-$C_4$-alkyl; X, Y independently of one another are oxygen or sulfur;

n is 0 or 1;

A is 0, $S(O)_k$ or $NR^{12}$, where k is 0, 1 or 2;

$R^4$, $R^8$, $R^9$ independently of one another are hydrogen or $C_1$-$C_4$-alkyl;

$R^5$, $R^{11}$ are $C_1$-$C_4$-alkyl;

$R^6$, $R^7$ independently of one another are hydrogen, $C_1$-$C_6$-alkyl, $C_3$-$C_6$-alkenyl, $C_3$-$C_6$-alkynyl, $C(O)R^4$, $COOR^5$ or $S(O)_2R^{11}$;

$R^{10}$, $R^{12}$ independently of one another are hydrogen, $C_1$-$C_6$-alkyl, $C_3$-$C_6$-alkenyl or $C_3$-$C_6$-alkynyl; and $R^{13}$ is phenyl which is unsubstituted or carries 1, 2, 3 or 4 substituents, where the substituents are selected from the group consisting of halogen, nitro, cyano, OH, alkyl, alkoxy, haloalkyl, haloalkoxy, $COOR^5$, $NR^6R^7$ and $C(O)NR^8R^9$; or an agriculturally useful salt thereof.

2. A compound as claimed in claim 1 wherein $R^3$ is hydrogen, $C_1$-$C_{10}$-alkyl, $C_3$-$C_{10}$-cycloalkyl, $C_3$-$C_8$-alkenyl, $C_3$-$C_8$-alkynyl, $C_5$-$C_{10}$-cycloalkenyl, $C_3$-$C_8$-cycloalkyl-$C_1$-$C_4$-alkyl, phenyl or 3-to 7-membered heterocyclyl, where the 8 last-mentioned groups may be unsubstituted, partially or fully halogenated and/or substituted by 1, 2 or 3 radicals selected from the group consisting of OH, CN, $NO_2$, COOH, $C_1$-$C_6$-alkyl, $C_1$-C6-haloalkyl, $C_1$-$C_6$-alkoxy, $C_1$-$C_4$-haloalkoxy, $C_2$-$C_6$-alkenyl, $C_2$-$C_6$-alkynyl, $C_1$-$C_6$-alkylthio, $C_1$-$C_4$-haloalkylthio, unsubstituted or substituted phenyl, $COOR^5$, $NR^6R^7$, and $C(O)NR^8R^9$, wherein each heterocyclyl may contain 1, 2 or 3 heteroatoms selected from the group consisting of oxygen, nitrogen, sulfur and a group $NR^{10}$ and, if appropriate, 1, 2 or 3 carbonyl groups and/or thiocarbonyl groups as ring members; or $R^2$ and $R^3$, together with the group N-(A)n to which they are attached, form a saturated 3- to 7-membered heterocycle which, in addition to the nitrogen atom, may contain 1, 2 or a further 3 heteroatoms selected from the group consisting of oxygen, nitrogen, sulfur and a group $NR^{10}$ and, if appropriate, 1, 2 or 3 carbonyl groups and/or thiocarbonyl groups as ring members.

3. A compound as claimed in claim 1 wherein $R^1$ is hydrogen.

4. A compound as claimed in claim 1 wherein $R^3$ is hydrogen or $C_1$-$C_4$-alkyl.

5. A compound as claimed in claim 1 wherein $R^2$ is $C_1$-$C_6$-alkyl, $C_3$-$C_6$-cycloalkyl, $C_3$-$C_6$-alkenyl, $C_3$-$C_6$-alkynyl, $C_5$-$C_6$-cycloalkenyl, substituted or unsubstituted phenyl, $C_3$-$C_6$-cycloalkyl-$C_1$-$C_4$-alkyl, where $C_1$-$C_6$-alkyl and $C_3$-$C_6$ cycloalkyl may be partially or fully halogenated and/or may contain at least one radical selected from the group consisting of $C_1$-$C_6$-alkoxy, $C_1$-$C_4$-haloalkoxy, $C_1$-$C_6$-alkylthio, $C_1$-$C_4$-haloalkylthio, unsubstituted or substituted phenyl, $COOR^5$, $NR^6R^7$ and $C(O)NR^8R^9$.

6. A compound as claimed in claim 1 wherein X and Y represent oxygen.

7. A compound as claimed in claim 1 wherein n=0.

8. A compound as claimed in claim 1 wherein the radicals $R^a$, $R^b$, $R^o$, $R^d$ and $R^e$ are selected from the group consisting of hydrogen, halogen, CN, $C_1$-$C_4$-alkyl, $OCH_3$, $CF_3$, $CHF_2$, $OCF_3$ and $OCHF_2$.

9. A compound as claimed in claim 1 wherein not more than 3 of the radicals $R^a$, $R^b$, $R^c$, $R^d$ and $R^e$ are different from hydrogen.

10. A compound as claimed in claim 1 wherein 2 or 3 of the radicals $R^a$, $R^b$, $R^c$, $R^d$ and $R^e$ are different from hydrogen.

11. A compound as claimed in claim 9 wherein the radicals $R^a$ and $R^e$ represent hydrogen.

12. A composition, comprising a herbicidally effective amount of at least one compound as claimed in claim 1, and at least one inert liquid and/or solid carrier, and, if desired, at least one surfactant.

13. A method for controlling unwanted vegetation, which comprises allowing a herbicidally effective amount of at least one compound as claimed in claim 1 to act on plants, their habitat or on a seed.

14. A method for controlling unwanted vegetation, comprising applying to plants, their habitat or to their seed a herbicidally effective amount of at least one compound of claim 1.

15. The method of claim 14, wherein said compound is applied at an application rate of from 0,001 to 3,0 kg/ha.

16. The method of claim 15, wherein the application rate of said compound is 0,01 to 1,0 kg/ha.

17. A compound of claim 1, wherein n is 1 and A, is oxygen, a group N-$R^{12}$, where $R^{12}$= hydrogen or alkyl, or a group $SO_2$.

18. A compound of claim 1, wherein $R^a$, $R^b$, $R^c$, $R_d$, $R^e$ are independently hydrogen, halogen, CN, $C_1$-$C_4$-alkyl, $C_1$-$C_4$-haloalkyl, $C_1$-$C_4$-alkoxy or $C_1$-$C_4$-haloalkoxy.

19. A compound of claim 1, wherein $R^1$ is hydrogen, OH, Cl, Br, $C_1$-$C_6$-alkyl or $OC(O)R^4$.

20. A compound of formula (Ia)

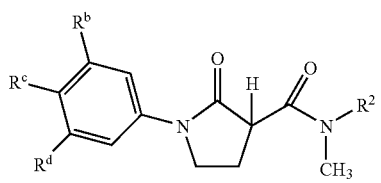

(Ia)

wherein

R$^b$, R$^c$, R$^d$ independently of one another are hydrogen, OH, CN, NO$_2$, halogen, C$_1$-C$_{10}$-alkyl, C$_3$-C$_6$-cycloalkyl, C$_2$-C$_6$-alkenyl, C$_2$-C$_6$-alkynyl, C$_1$-C$_6$-haloalkyl, C$_2$-C$_6$-haloalkenyl, C$_1$-C$_6$-alkoxy, C$_1$-C$_4$-haloalkoxy, C$_1$-C$_6$-alkylthio, C$_1$-C$_4$-haloalkylthio, C(O)R$^4$, COOR$^5$, NR$^6$R$^7$, C(O)NR$^8$R$^9$, S(O)$_2$NR$^8$R$^9$, S(O)R$^{11}$, S(O)$_2$R$^{11}$ or C$_1$-C$_4$-alkoxy-C$_1$-C$_6$-alkyl; and R$^2$ is C$_1$-C$_{10}$-alkyl, C$_3$-C$_8$-cycloalkyl, C$_3$-C$_8$-alkenyl, C$_3$-C$_8$-alkynyl, C$_5$-C$_8$-cycloalkenyl or C$_3$-C$_8$-cycloalkyl-C$_1$-C$_4$-alkyl, wherein C$_1$-C$_{10}$-alkyl and C$_3$-C$_8$-cycloalkyl may be partially or fully halogenated and/or may carry one or two radicals selected from the group consisting of C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl group, COOR$^5$, NR$^6$R$^7$ and C(O)NR$^8$R$^9$, and wherein said phenyl group may be unsubstituted or substituted by 1, 2 or 3 substituents selected from the group consisting of halogen, nitro, OH, CN, C$_1$-C$_6$-alkyl, C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl, COOR$^5$, NR$^6$R$^7$ and C(O)NR$^8$R$^9$.

21. A compound as claimed in claim 1,
wherein R$^2$ is C$_1$-C$_6$-alkyl, C$_3$-C$_6$-cycloalkyl, C$_3$-C$_6$-alkenyl, C$_3$-C$_6$-alkynyl, C$_5$-C$_6$-cycloalkenyl, substituted or unsubstituted phenyl, C$_3$-C$_6$-cycloalkyl-C$_1$-C$_4$-alkyl, where C$_1$-C$_6$-alkyl and C$_3$-C$_6$ cycloalkyl may be partially or fully halogenated and/or may contain at least one radical selected from the group consisting of C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl, COOR$^5$, NR$^6$R$^7$ and C(O)NR$^8$R$^9$;
wherein R$^3$ is hydrogen or C$_1$-C$_4$-alkyl; and
wherein X and Y represent oxygen.

22. A compound as claimed in claim 1,
wherein R$^2$ is C$_1$-C$_6$-alkyl, C$_3$-C$_6$-cycloalkyl, C$_3$-C$_6$-alkenyl, C$_3$-C$_6$-alkynyl, C$_5$-C$_6$-cycloalkenyl, substituted or unsubstituted phenyl, C$_3$-C$_6$-cycloalkyl-C$_1$-C$_4$-alkyl, where C$_1$-C$_6$-alkyl and C$_3$-C$_6$ cycloalkyl may be partially or fully halogenated and/or may contain at least one radical selected from the group consisting of C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl, COOR$^5$, NR$^6$R$^7$ and C(O)NR$^8$R$^9$;
wherein R$^3$ is hydrogen or C$_1$-C$_4$-alkyl;
wherein X and Y represent oxygen; and
wherein n is 0.

23. A compound as claimed in claim 1,
wherein R$^1$ is hydrogen;
wherein R$^2$ is C$_1$-C$_6$-alkyl, C$_3$-C$_6$-cycloalkyl, C$_3$-C$_6$-alkenyl, C$_3$-C$_6$-alkynyl, C$_5$-C$_6$-cycloalkenyl, substituted or unsubstituted phenyl, C$_3$-C$_6$-cycloalkyl-C$_1$-C$_4$-alkyl, where C$_1$-C$_6$-alkyl and C$_3$-C$_6$ cycloalkyl may be partially or fully halogenated and/or may contain at least one radical selected from the group consisting of C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl, COOR$^5$, NR$^6$R$^7$ and C(O)NR$^8$R$^9$;
wherein R$^3$ is hydrogen or C$_1$-C$_4$-alkyl; and
wherein X and Y represent oxygen.

24. A compound as claimed in claim 1,
wherein R$^1$ is hydrogen;
wherein R$^2$ is C$_1$-C$_6$-alkyl, C$_3$-C$_6$-cycloalkyl, C$_3$-C$_6$-alkenyl, C$_3$-C$_6$-alkynyl, C$_5$-C$_6$-cycloalkenyl, substituted or unsubstituted phenyl, C$_3$-C$_6$-cycloalkyl-C$_1$-C$_4$-alkyl, where C$_1$-C$_6$-alkyl and C$_3$-C$_6$ cycloalkyl may be partially or fully halogenated and/or may contain at least one radical selected from the group consisting of C$_1$-C$_6$-alkoxy, C$_1$-C$_4$-haloalkoxy, C$_1$-C$_6$-alkylthio, C$_1$-C$_4$-haloalkylthio, unsubstituted or substituted phenyl, COOR$^5$, NR$^6$R$^7$ and C(O)NR$^8$R$^9$;
wherein R$^3$ is hydrogen or C$_1$-C$_4$-alkyl;
wherein X and Y represent oxygen; and
wherein n is 0.

* * * * *